US012100121B2

(12) United States Patent
Guo et al.

(10) Patent No.: US 12,100,121 B2
(45) Date of Patent: *Sep. 24, 2024

(54) SYSTEM, METHOD AND COMPUTER-ACCESSIBLE MEDIUM FOR DETECTING STRUCTURAL DISORDER(S) USING MAGNETIC RESONANCE IMAGING

(71) Applicant: THE TRUSTEES OF COLUMBIA UNIVERSITY IN THE CITY OF NEW YORK, New York, NY (US)

(72) Inventors: Jia Guo, Fort Lee, NJ (US); Scott A. Small, Millerton, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/347,948

(22) Filed: Jun. 15, 2021

(65) Prior Publication Data

US 2021/0383507 A1    Dec. 9, 2021

Related U.S. Application Data

(63) Continuation of application No. 17/000,904, filed on Aug. 24, 2020.

(Continued)

(51) Int. Cl.
    *G06T 5/00*       (2024.01)
    *G06T 5/50*       (2006.01)
    (Continued)

(52) U.S. Cl.
    CPC .............. *G06T 5/00* (2013.01); *G06T 5/50* (2013.01); *G16H 30/20* (2018.01); *G16H 30/40* (2018.01);
    (Continued)

(58) Field of Classification Search
    CPC . G06T 5/001; G06T 5/50; G06T 2207/10096; G06T 2207/20081;
    (Continued)

(56) References Cited

U.S. PATENT DOCUMENTS

2010/0215239 A1* 8/2010 Assaf .................. A61B 5/055
                                                  600/410
2017/0039714 A1* 2/2017 Small ..................... G06T 5/50
(Continued)

OTHER PUBLICATIONS

Ronneberger et al. "U-Net: Convolutional Networks for Biomedical Image Segmentation." Medical Image Computing and Computer-Assisted Intervention—MICCAI 2015. MICCAI 2015. Lecture Notes in Computer Science(), vol. 9351. Springer, Cham. https://doi.org/10.1007/978-3-319-24574-4_28 (Year: 2015).*

(Continued)

*Primary Examiner* — Qian Yang
(74) *Attorney, Agent, or Firm* — Hunton Andrews Kurth LLP

(57) ABSTRACT

An exemplary system, method, and computer-accessible medium for detection of structural disorder(s) of patient(s) can be provided which can include, for example, receiving magnetic resonance imaging (MRI) information of the portion(s), generating gadolinium ("Gd") enhanced map(s) based on the MRI information using a machine learning procedure(s), and detecting the structural disorder(s) of the patient(s) based on a GD contrast of the Gd enhanced map(s). The Gd enhanced map(s) can be a full dosage Gd enhanced map. The machine learning procedure can be a convolutional neural network. The MRI information can include (i) a low-dosage Gd MRI scan(s), or (ii) a Gd-free MRI scan(s). The Gd contrast can be generated in the Gd enhanced map(s) using a T2-weighted MRI image of the portion(s). Structural disorder(s) can include Stroke, tumor, (Continued)

trauma, infection, Multiple sclerosis and/or other inflammatory disease.

22 Claims, 35 Drawing Sheets

Related U.S. Application Data

(60) Provisional application No. 63/048,937, filed on Jul. 7, 2020, provisional application No. 62/977,018, filed on Feb. 14, 2020, provisional application No. 62/890,868, filed on Aug. 23, 2019.

(51) Int. Cl.
     *G16H 30/20*     (2018.01)
     *G16H 30/40*     (2018.01)
     *G16H 50/20*     (2018.01)
     *G16H 50/50*     (2018.01)

(52) U.S. Cl.
     CPC ............ *G16H 50/20* (2018.01); *G16H 50/50* (2018.01); *G06T 2207/10096* (2013.01); *G06T 2207/20081* (2013.01); *G06T 2207/20084* (2013.01); *G06T 2207/30016* (2013.01)

(58) Field of Classification Search
     CPC . G06T 2207/20084; G06T 2207/30016; G06T 5/00; G06T 5/60; G06T 5/92; G06T 2207/10088; G16H 50/50; G16H 50/20; G16H 30/20; G16H 30/40; G16H 50/70
     See application file for complete search history.

(56) References Cited

U.S. PATENT DOCUMENTS

| | | | | |
|---|---|---|---|---|
| 2019/0122348 | A1* | 4/2019 | Jensen | G06T 11/00 |
| 2020/0311914 | A1* | 10/2020 | Zaharchuk | G06V 10/454 |
| 2021/0030301 | A1* | 2/2021 | Wang | G01R 33/5601 |
| 2021/0052233 | A1* | 2/2021 | Kaplan | G06N 3/0454 |
| 2021/0241458 | A1* | 8/2021 | Zaharchuk | G06T 5/002 |
| 2021/0313046 | A1* | 10/2021 | Xing | G06N 3/08 |
| 2021/0383538 | A1* | 12/2021 | Deasy | G06T 7/11 |
| 2022/0130033 | A1* | 4/2022 | Rashidi | G06T 7/0008 |

OTHER PUBLICATIONS

Christen et al., "Predicting Contrast Agent Enhancement with Deep Convolution Networks", Proc. Intl. Soc. Mag. Reson. Med. 26 (2018) (Year: 2018).*
Abujudeh, Kaewlai et al. Nephrogenic Systemic Fibrosis after Gadopentetate Dimeglumine Exposure: Case Series of 36 Patients Radiology, vol. 253, No. 1, pp. 81-89, Oct. 2009.
Lu, Hanzhang et al. Functional Magnetic Resonance Imaging Based on Changes in Vascular Space Occupancy, Magnetic Resonance in Medicine, vol. 50, pp. 263-274, 2003.
S. A. Small et al., "A pathophysiological framework of hippocampal dysfunction in ageing and disease", Nat Rev Neurosci, vol. 12, No. 10, pp. 585-601, 2011.
U. A. Khan et al., "Molecular drivers and cortical spread of lateral entorhinal cortex dysfunction in preclinical Alzheimer's disease", Nat Neurosci, vol. 17, No. 2, pp. 304-311, 2014.
S. A. Schobel et al., "Imaging patients with psychosis and a mouse model establishes a spreading pattern of hippocampal dysfunction and implicates glutamate as a driver", Neuron, vol. 78, n. 1, pp. 81-93, 2013.
A. M. Brickman et al., "Enhancing dentate gyrus function with dietary flavanols improves cognition in older adults,", Nat Neurosci, vol. 17, No. 12, pp. 1798-1803, 2014.

E. Gong et al., "Deep learning enables reduced gadolinium dose for contrast-enhanced brain MRI" Journal of Magnetic Resonance Imaging, vol. 48, No. 2, pp. 330-340.
Y. Dubey et al., "FCM Clustering Algorithms for Segmentation of Brain MR Images" Advances in Fuzzy Systems, vol. 2016, pp. 1-14, 2016.
K. He et al., "Deep Residual Learning for Image Recognition" in 2016 IEEE Conference on Computer Vision and Pattern Recognition (CVPR), Jun. 27-30, 2016 2016, pp. 770-778.
O. Oktay et al., "Attention U-Net: Learning Where to Look for the Pancreas" 1st Conference on Medical Imaging with Deep learning, Amsterdam, The Netherlands, pp. 1-10, 2018.
A. Hore et al., "Image Quality Metrics: PSNR vs. SSIM" in 2010 20th International Conference on Pattern Recognition, pp. 2366-2369, Aug. 2010.
J. Lohrke et al., "25 Years of Contrast-Enhanced MRI: Developments, Current Challenges and Future Perspectives" Advances in Therapy, vol. 33, No. 1, pp. 1-28, 2016.
W. Jagust, "Vulnerable neural systems and the borderland of brain aging and neurodegeneration", Neuron, vol. 77, No. 2, pp. 219-234, 2013.
J. Uh et al., "Cerebral blood volume in Alzheimer's disease and correlation with tissue structural integrity", Neurobiol Aging, vol. 31, No. 12, pp. 2038-2046, 2010.
D. J Covarrubias et al., "Dynamic Magnetic Resonance Perfusion Imaging of Brain Tumors" The oncologist, vol. 9, pp. 528-537, 2004.
M. Neska-Matuszewska et al."Differentiation of glioblastoma multiforme, metastases and primary central nervous system lymphomas using multiparametric perfusion and diffusion MR imaging of a tumor core and a peritumoral zone—Searching for a practical approach", PLoS One, vol. 13, No. 1, pp. e0191341-e0191341, 2018.
J. Zhang et al., "Clinical Applications of Contrast-Enhanced Perfusion MRI Techniques in Gliomas: Recent Advances and Current Challenges", Contrast Media Mol Imaging, vol. 2017, pp. 7064120-7064120, 2017.
A. Simko et al., A Generalized Network for MRI Intensity Normalization. Proceedings of Machine learning Research, Under Review 1-4, 2019.
B. Fischl. FreeSurfer. Neuroimage, vol. 62, No. 2, pp. 774-781, 2012.
X. Feng et al., Temporal lobe epilepsy lateralization using retrospective cerebral blood volume MRI. NeuroImage: Clinical, val. 19, pp. 911-917, 2018.
J. L. Price et al., Neuron number in the entorhinal cortex and CA1 in preclinical Alzheimer disease. Archives of neurology, val. 58, No. 9, pp. 1395-1402, 2001.
Dillman, J. R. et al., Gadolinium retention—5 years later . . . Pediatr. Radiol. vol. 50, pp. 166-167, 2020.
Provenzano, F. A. et al. Hippocampal Pathology in Clinical High-Risk Patients and the Onset of Schizophrenia. Biol. Psychiatry, vol. 87, pp. 234-242, 2020.
Pavlopoulos, E. et al. Molecular mechanism for age-related memory loss: the histone-binding protein RbAp48. Sci. Transl. Med. vol. 5, pp. 1-28, 2013.
Lei, L. et al. Glioblastoma Models Reveal the Connection between Adult Glial Progenitors and the Proneural Phenotype. PLOS ONE, vol. 6, Issue 5, pp. 1-15, 2011.
Ledig, C. et al. Robust whole-brain segmentation: Application to traumatic brain injury. Med. Image Anal. 21, pp. 40-58 2015.
Petersen, R. C. et al. Alzheimer's Disease Neuroimaging Initiative (ADNI). Neurology, vol. 74, 201-209, 2010.
Menze, B. H. et al. The Multimodal Brain Tumor Image Segmentation Benchmark (BRATS). IEEE Trans. Med. Imaging 34, 1993-2024, 2015.
Chou, N. et al., Robust Automatic Rodent Brain Extraction Using 3-D Pulse-Coupled Neural Networks (PCNN). IEEE Trans. Image Process. vol. 20, pp. 2554-2564, 2011.
Bezdek, J. C. et al., FCM: The fuzzy c-means clustering algorithm. Comput. Geosci. 10, 191-203 (1984).
Cox, I. J., et al., Dynamic histogram warping of image pairs for constant image brightness. in Proceedings., International Conference on Image Processing vol. 2, 366-369 vol. 2 (1995).

(56) References Cited

OTHER PUBLICATIONS

Wagenknecht, G., et al., Dynamic programming algorithm for contrast correction in medical images. in Nonlinear Image Processing XI vol. 3961, 216-226 (International Society for Optics and Photonics, 2000).
Bakas, S. et al. Advancing The Cancer Genome Atlas glioma MRI collections with expert segmentation labels and radiomic features. Sci. Data 4, 170117 (2017).
Clark, K. et al. The Cancer Imaging Archive (TCIA): Maintaining and Operating a Public Information Repository. J. Digit. Imaging 26, 1045-1057 (2013).
Ronneberger, O., et al., T. U-Net: Convolutional Networks for Biomedical Image Segmentation. ArXiv150504597 Cs (2015).
He, Kaiming et al., Deep Residual Learning for Image Recognition. pp. 1-12, ArXiv151203385 Cs, (2015).
Vaswani, A. et al. Attention Is All You Need. 31st Conference on Neural Information Processing Systems, pp. 1-15, (2017).
Oktay, O. et al. Attention U-Net: Learning Where to Look for the Pancreas. 1st Conference on Medical Imaging with Deep Learning, pp. 1-10, (2018).
Barron, J. T. A General and Adaptive Robust Loss Function. in pp. 4331-4339 (2019).
Otsu, N. A Threshold Selection Method from Gray-Level Histograms. IEEE Trans. Syst. Man Cybern. vol. 9, pp. 62-66 (1979).
Pedregosa, F. et al. Scikit-learn: Machine Learning in Python. Mach. Learn. Python, Journal of Machine Learning Research, vol. 12, pp. 2825-2830, 2011.
Avants, B. B. et al., Advanced Normalization Tools (ANTS). pp. 1-41, Jul. 10, 2014.
Fonov, V. et al. Unbiased average age-appropriate atlases for pediatric studies. NeuroImage 54(1), 313-327 (2011).
Fonov, V. et al., Unbiased nonlinear average age-appropriate brain templates from birth to adulthood. NeuroImage 47, S102 (2009).
Collins, D. L. et al., Animal+Insect: Improved Cortical Structure Segmentation. in Information Processing in Medical Imaging (eds. Kuba, A., Šáamal, M. & Todd-Pokropek, A.) pp. 210-223, Springer, 1999.
Cox, R. W. AFNI: software for analysis and visualization of functional magnetic resonance neuroimages. Comput. Biomed. Res. Int. J. 29, 162-173 (1996).
Forman, S. D. et al. Improved assessment of significant activation in functional magnetic resonance imaging (fMRI): use of a cluster-size threshold. Magn. Reson. Med. 33, 636-647 (1995).
Cox, R. W. et al., FMRI Clustering in AFNI: False-Positive Rates Redux. Brain Connect. 7, 152-171 (2017).
Fedorov, A. et al. 3D Slicer as an Image Computing Platform for the Quantitative Imaging Network. Magn. Reson. Imaging 30, 1323-1341 (2012).
Lohrke, Frenzel et al. "25 Years of Contrast-Enhanced MRI: Developments, Current Challenges and Future Perspectives" Arlv Ther (2016) 11: 1-2R, 2016.
Frenzel, Lengsfeld et al. "Stability of Gadolinium-Based Magnetic Resonance Imaging Contrast Agents in Human Serum at 37° C" Investigative Radiology • vol. 43, No. 12, Dec. 2008.
Marino, Helbich et al. "Multiparametric MRI of the Breast: A Review" International Society for Magnetic Resonance in Medicine 30, 2018.
Bakshi, Thompson et al. "MRI in multiple sclerosis: current status and future prospects" Lancet Neurol. Jul. 2008 ; 7 (7): 615-625.
Brickman, Khan et al. "Enhancing dentate gyrus function with dietary flavanols improves cognition in older adults" Nat Neurosci. Dec. 2014 ; 17(12): 1798-1803.
Khan, Liu et al. "Molecular drivers and cortical spread of lateral entorhinal cortex dysfunction in preclinical Alzheimer's disease" Nat Neurosci. Feb. 2014 ; 17(2): 304-311.
Neska-Matuszewska, Bladowska et al. "The role of diffusion and perfusion magnetic resonance imaging in differentiation of haemangioblastomas and pilocytic astrocytomas" Pol J Radiol 2018; 83: e197-e203.
Saade, Bou-Fakhredin et al. "Gadolinium and Multiple Sclerosis: Vessels, Barriers of the Brain, and Glymphatics" AJNR Am J Neuroradiol, 2018.
Shan, Padole et al. "Competitive performance of a modularized deep neural network compared to commercial algorithms for low-dose CT image reconstruction" Nat Mach Intell. Jun. 2019 ; 1(6): 269-276.
Dubey and Mushrif "Segmentation of brain MR images using rough set based intuitionistic fuzzy clustering" biocybern etics and biomedical engineering 36 (2016 ) 413-426.
Myronenko "Robust Semantic Segmentation of Brain Tumor Regions from 3D MRIs" 2019.
Rockafellar and J-B Wets "Variational Analysis" 1997, 2nd printing 2004, 3rd printing 2009.
Feng, Hamberger et al. "Temporal lobe epilepsy lateralization using retrospective cerebral blood volume MRI" NeuroImage: Clinical 19 (2018) 911-917.
Raichle :The Pathophysiology of Brain Ischemia, Neurological Progress, Ann Neurol 13:2-10, 1983.
Belliveau, Kennedy et al. "Functional Mapping of the Human Visual Cortex by Magnetic Resonance Imaging" Science, New Series, vol. 254, No. 5032 (Nov. 1, 1991), 716-719.
William Jagust "Vulnerable Neural Systems and the Borderland of Brain Aging and Neurodegeneration" Neuron. Jan. 23, 2013; 77(2): 219-234.
J Covarrubias, Rosen et al. "Dynamic Magnetic Resonance Perfusion Imaging of Brain Tumors" The Oncologist 2004, 9:528-537.
Takano, Yamashita et al. "Molecular Therapeutic Targets for Glioma Angiogenesis" Hindawi Publishing Corporation Journal of Oncology, vol. 2010, Article ID 351908, 11 pages, 2010.
Noell, Ritz et al. "An Allograft Glioma Model Reveals the Dependence of Aquaporin-4 Expression on the Brain Microenvironment" PLoS ONE, May 2012 | vol. 7 | Issue 5 | e36555.
Neska-Matuszewska, Bladowska et al. "Differentiation of glioblastoma multiforme, metastases and primary central nervous system lymphomas using multiparametric perfusion and diffusion MR imaging of a tumor core and a peritumoral zone—Searching for a practical approach" PLOS ONE, Jan. 17, 2018.
Voulodimos, Doulamis et al. "Deep Learning for Computer Vision: A Brief Review" Computational Intelligence and Neuroscience, vol. 2018, Article ID 7068349, 13 pages.
Sørensen "A Method of Establishing Groups of Equal Amplitude in Plant Sociology Based on Similarity of Species Content and Its Application to Analyses of the Vegetation on Danish Commons" Det Kongelige Danske Videnskabernes Selskab, Biologiske Skrifter, Bind V, Nr. 4, 1948.
Schobel, Chaudhury et al. "Imaging patients with psychosis and a mouse model establishes a spreading pattern of hippocampal dysfunction and implicates glutamate as a pathogenic driver" Neuron. Apr. 10, 2013; 78(1): 81-93.
Desikan et al., "An automated labeling system for subdividing the human cerebral cortex on MRI scans into gyral based regions of interest" NeuroImage 31 (2006) 968-980.
B. Fischl et al., "Automatically Parcellating the Human Cerebral Cortex" Cerebral Cortex Jan. 2004;14:11-22.
Iglesias et al., "Multi-Atlas Segmentation of Biomedical Images: A Survey" Med Image Anal. Aug. 2015 ; 24(1): 205-219.
S. A. Small, et al. "A pathophysiological framework of hippocampal dysfunction in ageing and disease" Nat Rev Neurosci. ; 12(10): 585-601.
T. E. Smith, et al. "Gadolinium Deposition in Neurology Clinical Practice", Ochsner J, vol. 19, No. 1, pp. 17-25, Spring 2019.
FDA. "FDA Drug Safety Communication: FDA warns that gadolinium-based contrast agents (GBCAs) are retained in the body; requires new class warnings.".
L. Lei et al., "Glioblastoma models reveal the connection between adult glial progenitors and the proneural phenotype", PLoS One, vol. 6, No. 5, pp. e20041-e20041, 2011.
H. Moreno, F. Hua, T. Brown, and S. Small, "Longitudinal mapping of mouse cerebral blood volume with MRI" NMR in Biomedicine, vol. 19, No. 5, pp. 535-543, 2006.
O. Ronneberger, P. Fischer, and T. Brox, "U-Net: Convolutional Networks for Biomedical Image Segmentation" in Medical Image

(56) References Cited

OTHER PUBLICATIONS

Computing and Computer-Assisted Intervention—MICCAI 2015, Cham, N. Navab, J. Hornegger, W. M. Wells, and A. F. Frangi, Eds., 2015// 2015: Springer International Publishing.
O. Oktay et al., "Attention U-Net: Learning Where to Look for the Pancreas" arXiv e-prints, Apr. 2018.
A. Hore and D. Ziou, "Image Quality Metrics: PSNR vs. SSIM" in 2010 20th International Conference on Pattern Recognition, Aug. 23-26, 2010 2010, pp. 2366-2369.
M. Law et al., "Comparison of Cerebral Blood Volume and Vascular Permeability from Dynamic Susceptibility Contrast-Enhanced Perfusion MR Imaging with Glioma Grade" American Journal of Neuroradiology, vol. 25, No. 5, p. 746, 2004.
M. Law et al., "Glioma Grading: Sensitivity, Specificity, and Predictive Values of Perfusion MR Imaging and Proton MR Spectroscopic Imaging Compared with Conventional MR Imaging" American Journal of Neuroradiology, vol. 24, No. 10, p. 1989, 2003.
J. Kleesiek et al. Can Virtual Contrast Enhancement in Brain MRI Replace Gadolinium ?: A Feasibility Study. Investigative Radiology, val. 54, No. 10, pp. 653-660, 2019.
A.M. Brickman, et al., Enhancing dentate gyrus function with dietary flavanols improves cognition in older adults. Nature Neuroscience, val. 17, No. 12, pp. 1798, 2014.
U. A. Khan, et al. Molecular drivers and cortical spread of lateral entorhinal cortex dysfunction in preclinical Alzheimer's disease. Nature neuroscience, val. 17, No. 2, pp. 304, 2014.
F. A. Provenzano, J et al. Hippocampal Pathology in Clinical High-Risk Patients and the Onset of Schizophrenia. Biological Psychiatry. 2019.
X. Feng, et al. Temporal lobe epilepsy lateralization using retrospective cerebral blood volume MRI. NeuroImage: Clinical, val. 19, pp. 911-917, 2018.
S.M. McGinnis, M. Brickhouse, B. Pascual, and B. C. Dickerson. Age-Related Changes in the Thickness of Cortical Zones in Humans. Brain topography, vol. 24, No. 3-4, pp. 279, 2011.
A. Bakkour, et al. The effects of aging and Alzheimer's disease on cerebral cortical anatomy: specificity and differential relationships with cognition. Neuroimage, val. 76, pp. 332-344, 2013.
Borges, A. R., et al. How They Compare with Human Disease, Reflect Tumor Biology, and Play a Role in Preclinical Trials. Am. J. Neuroradiol. 33, 24-36 (2012).
Shen, Q. & Duong, T. Magnetic resonance imaging of cerebral blood flow in animal stroke models. Brain Circ. Mumbai 2, (2016).
Lewandowski, N. M. et al. Regional vulnerability in Huntington's disease: fMRI-guided molecular analysis in patients and a mouse model of disease. Neurobiol. Dis. 52, 84-93 (2013).
Ramalho, M., Ramalho, J., Burke, L. M. & Semelka, R. C. Gadolinium Retention and Toxicity—An Update. Adv. Chronic Kidney Dis. 24, 138-146 (2017).
Guo, B. J., Yang, Z. L. & Zhang, L. J. Gadolinium Deposition in Brain: Current Scientific Evidence and Future Perspectives. Front. Mol. Neurosci. 11, (2018).
Gong, E., Pauly, J. M., Wintermark, M. & Zaharchuk, G. Deep learning enables reduced gadolinium dose for contrast-enhanced brain MRI. J. Magn. Reson. Imaging 48, 330-340 (2018).
Kleesiek, J. et al. Can Virtual Contrast Enhancement in Brain MRI Replace Gadolinium?: A Feasibility Study. Invest. Radiol. 54, 653-660 (2019).
(ISMRM 2019) Contrast-free MRI Contrast Enhancement with Deep Attention Generative Adversarial Network. http://archive.ismrm.org/2019/1091.html.
Small, S. A., Schobel, S. A., Buxton, R. B., Witter, M. P. & Barnes, C. A. A pathophysiological framework of hippocampal dysfunction in ageing and disease. Nat. Rev. Neurosci. 12, 585-601 (2011).
Brickman, A. M. et al. Enhancing dentate gyrus function with dietary flavanols improves cognition in older adults. Nat. Neurosci. 17, 1798-1803 (2014).
Fischl, B. FreeSurfer. NeuroImage 62, 774-781 (2012).
Bakas, S. et al. Segmentation Labels for the Pre-operative Scans of the TCGA-GBM colleciton. (2017).
SPM—Statistical Parametric Mapping. https://www.fil.ion.ucl.ac.uk/spm/.
Non Final Office Action dated Sep. 28, 2022 for U.S. Appl. No. 17/347,917.
Non Final Office Action for corresponding U.S. Appl. No. 17/000,904 dated Dec. 29, 2022.
Non Final Office Action for corresponding U.S. Appl. No. 17/347,917 dated Jan. 9, 2023.
Final Office Action mailed on Apr. 11, 2023 for U.S. Appl. No. 17/000,904.
Final Office Action mailed on Apr. 12, 2023 for U.S. Appl. No. 17/347,917.

\* cited by examiner

Figure 6A
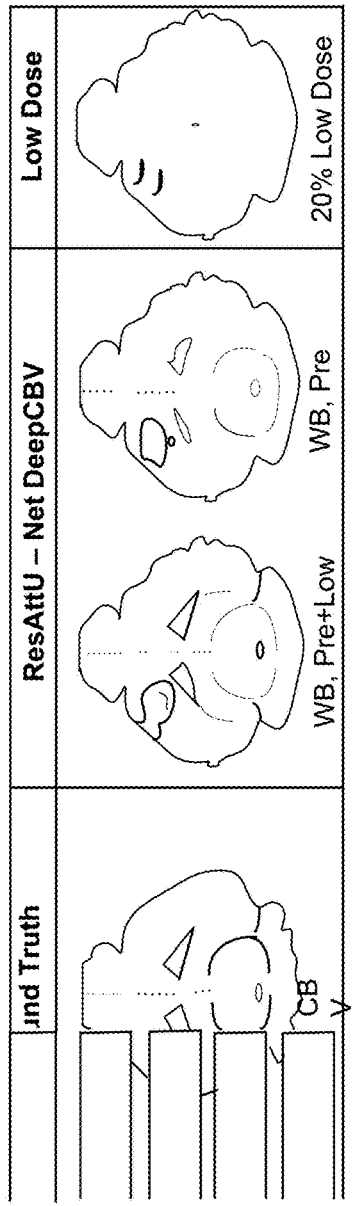
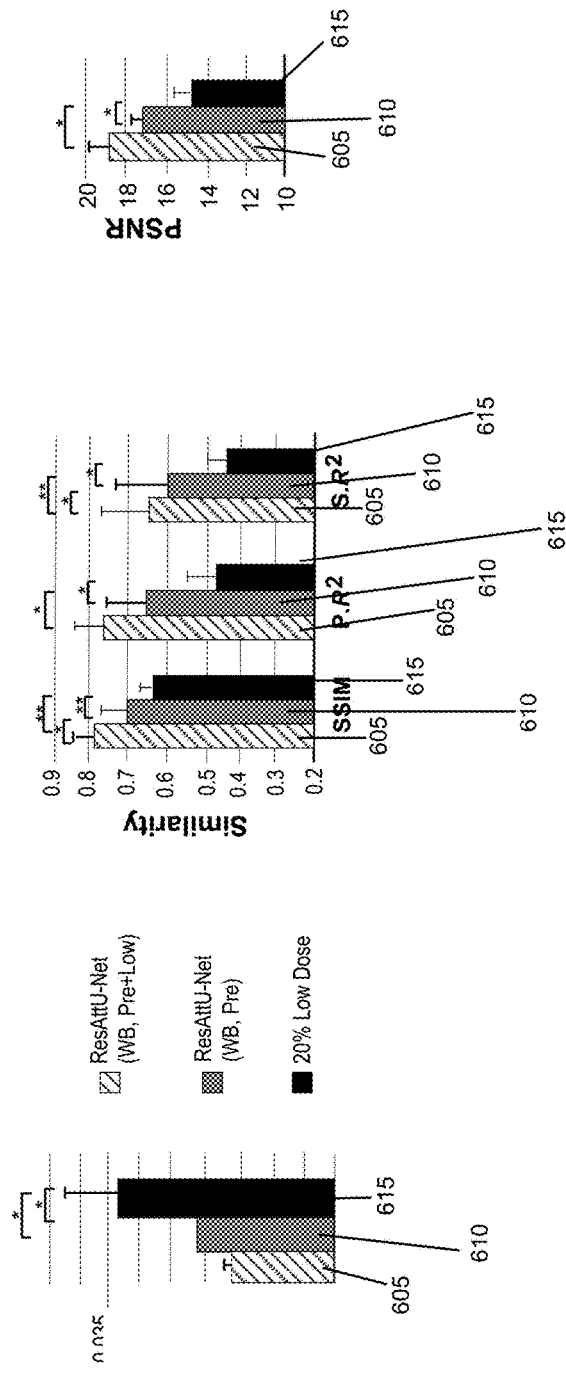
Figure 6B

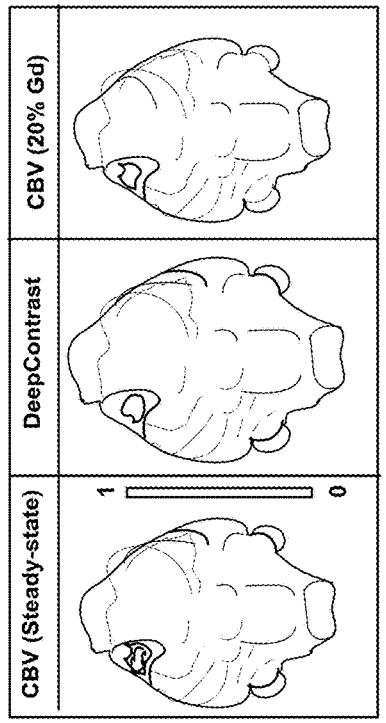
Figure 14A
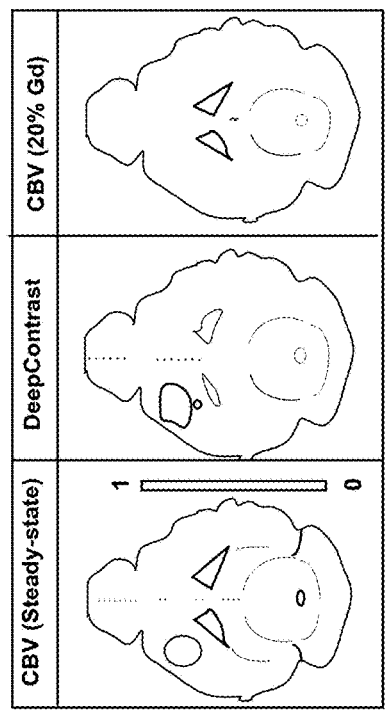
Figure 14B
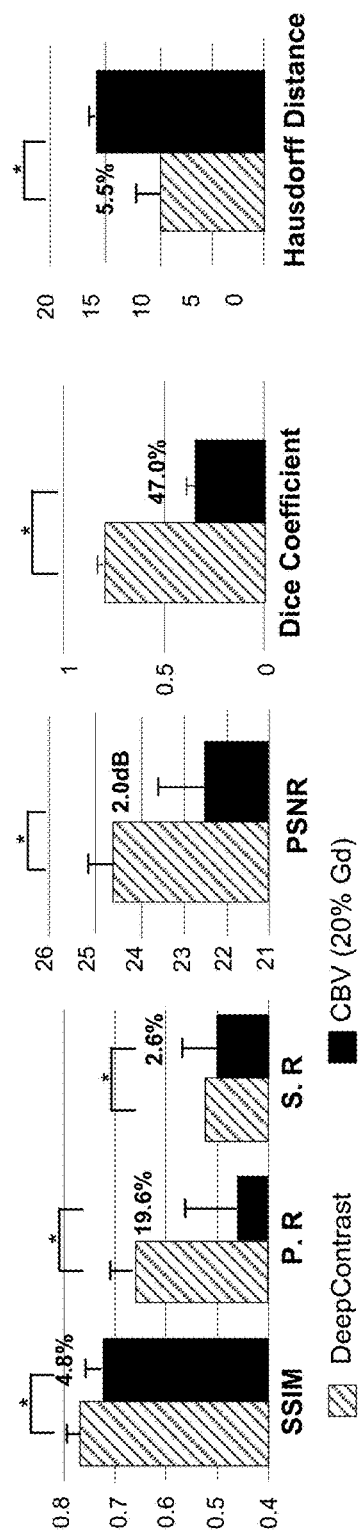
Figure 14C
Figure 14D

Figure 21A
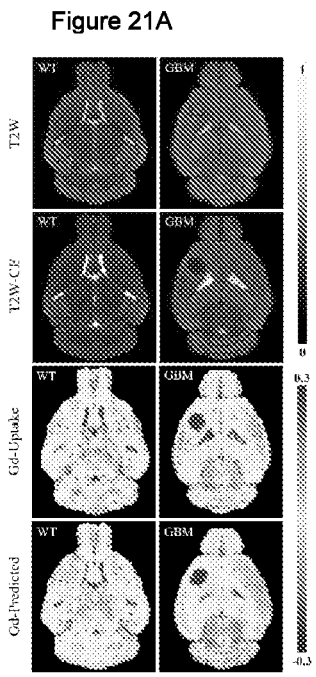
Figure 21B
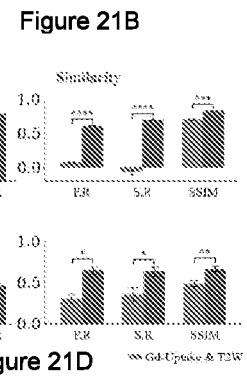
Figure 21C
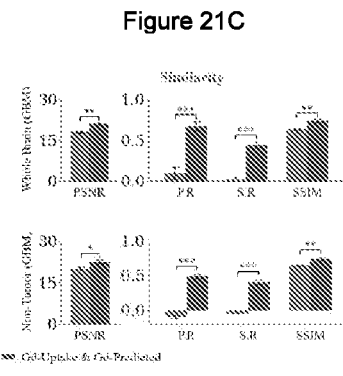
Figure 21D
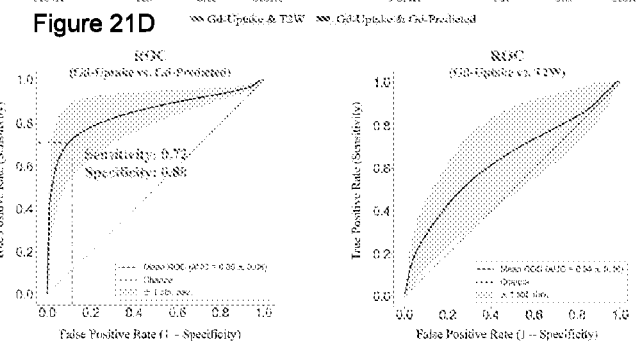
Figure 21E
Figure 21F Figure 23A
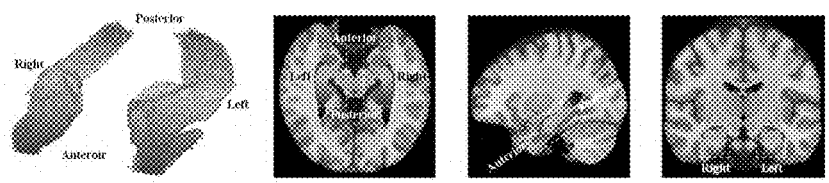
Figure 23B
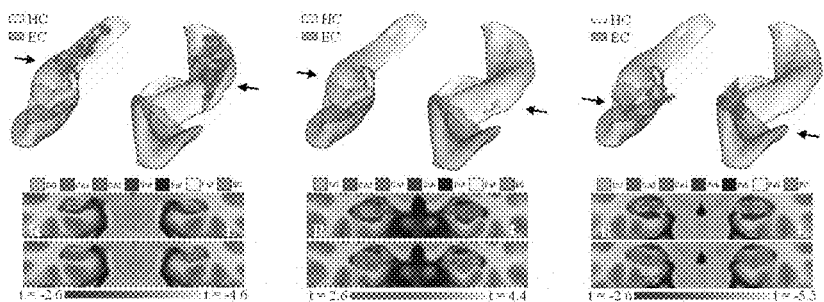
Figure 23D
Figure 23C
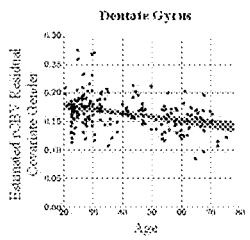
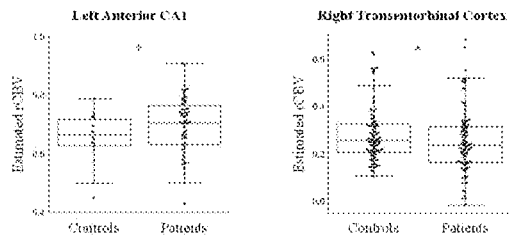
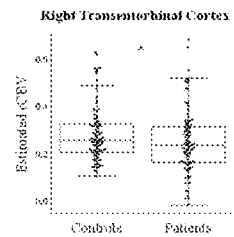
Figure 23E
Figure 23G
Figure 23F

| Model | Evaluation | Region | Data | PSNR | P.R | S.R | SSIM |
|---|---|---|---|---|---|---|---|
| Healthy Mouse Brain | Similarity (WT) | Whole Brain | Gd-Uptake & T2W | 22.16±0.59 | -0.072±0.032 | 0.074±0.013 | 0.707±0.007 |
| | | | Gd-Uptake & Gd-Predicted | 24.59±0.60 | 0.695±0.008 | 0.606±0.008 | 0.831±0.008 |
| Tumor Mouse Brain | Similarity (GBM) | Whole Brain | Gd-Uptake & T2W | 18.00±0.44 | 0.092±0.076 | 0.017±0.026 | 0.629±0.009 |
| | | | Gd-Uptake & Gd-Predicted | 21.07±0.43 | 0.670±0.060 | 0.442±0.035 | 0.737±0.019 |
| | | Tumor | Gd-Uptake & T2W | 10.15±1.27 | 0.301±0.053 | 0.357±0.085 | 0.484±0.035 |
| | | | Gd-Uptake & Gd-Predicted | 13.80±0.83 | 0.642±0.051 | 0.629±0.054 | 0.663±0.036 |
| | | Non-Tumor | Gd-Uptake & T2W | 19.92±0.68 | -0.098±0.023 | -0.043±0.004 | 0.641±0.008 |
| | | | Gd-Uptake & Gd-Predicted | 22.48±0.66 | 0.487±0.029 | 0.400±0.035 | 0.736±0.018 |
| Healthy Human Brain | Similarity (CN) | Whole Brain | Gd-Uptake & T1W | 15.40±0.09 | -0.194±0.003 | -0.323±0.005 | 0.446±0.002 |
| | | | Gd-Uptake & Gd-Predicted | 29.64±0.07 | 0.822±0.002 | 0.625±0.003 | 0.879±0.002 |
| | | White Matter | Gd-Uptake & T1W | 10.42±0.07 | 0.029±0.002 | 0.033±0.003 | 0.457±0.001 |
| | | | Gd-Uptake & Gd-Predicted | 35.15±0.09 | 0.633±0.006 | 0.437±0.002 | 0.969±0.001 |
| | | Gray Matter | Gd-Uptake & T1W | 14.72±0.06 | -0.029±0.002 | -0.039±0.003 | 0.462±0.001 |
| | | | Gd-Uptake & Gd-Predicted | 30.18±0.07 | 0.807±0.004 | 0.510±0.003 | 0.946±0.001 |
| | | CSF | Gd-Uptake & T1W | 20.65±0.07 | 0.124±0.003 | 0.120±0.004 | 0.802±0.003 |
| | | | Gd-Uptake & Gd-Predicted | 25.47±0.08 | 0.728±0.004 | 0.604±0.003 | 0.936±0.001 |
| | Test-Retest Reliability (CN) | Whole Brain | Gd-Uptake of two consecutive acquisitions | 27.70±0.24 | 0.815±0.007 | 0.415±0.017 | 0.832±0.007 |
| | | | Gd-Predicted of two consecutive acquisitions | 30.11±0.44 | 0.919±0.005 | 0.722±0.010 | 0.948±0.002 |
| | | White Matter | Gd-Uptake of two consecutive acquisitions | 31.18±0.18 | 0.713±0.015 | 0.129±0.008 | 0.943±0.003 |
| | | | Gd-Predicted of two consecutive acquisitions | 35.14±0.40 | 0.899±0.006 | 0.368±0.014 | 0.988±0.000 |
| | | Gray Matter | Gd-Uptake of two consecutive acquisitions | 27.89±0.32 | 0.844±0.008 | 0.327±0.021 | 0.915±0.003 |
| | | | Gd-Predicted of two consecutive acquisitions | 30.42±0.44 | 0.937±0.004 | 0.596±0.013 | 0.978±0.001 |
| | | CSF | Gd-Uptake of two consecutive acquisitions | 24.04±0.27 | 0.762±0.014 | 0.585±0.019 | 0.911±0.003 |
| | | | Gd-Predicted of two consecutive acquisitions | 26.33±0.48 | 0.882±0.009 | 0.800±0.008 | 0.968±0.001 |
| Tumor Human Brain | Similarity (Brain Tumor) | Whole Brain | Gd-Uptake & T1W | 17.17±0.25 | 0.127±0.047 | 0.207±0.058 | 0.546±0.010 |
| | | | Gd-Uptake & Gd-Predicted | 26.65±0.26 | 0.656±0.016 | 0.439±0.028 | 0.802±0.004 |
| | | Tumor | Gd-Uptake & T1W | 11.96±0.59 | 0.013±0.060 | 0.033±0.058 | 0.503±0.035 |
| | | | Gd-Uptake & Gd-Predicted | 24.16±0.41 | 0.544±0.035 | 0.372±0.031 | 0.843±0.014 |
| | | Non-Tumor | Gd-Uptake & T1W | 17.22±0.24 | 0.131±0.047 | 0.214±0.059 | 0.566±0.012 |
| | | | Gd-Uptake & Gd-Predicted | 26.59±0.25 | 0.660±0.017 | 0.445±0.030 | 0.813±0.005 |
| Tumor Human Breast | Similarity (Breast Cancer) | Whole Breast | Gd-Uptakc & T1W | 20.12±0.52 | 0.165±0.055 | 0.051±0.036 | 0.056±0.035 |
| | | | Gd-Uptake & Gd-Predicted | 26.51±0.49 | 0.613±0.028 | 0.571±0.017 | 0.761±0.017 |
| | | Tumor | Gd-Uptake & T1W | 0±0 | 0±0 | 0±0 | 0±0 |
| | | | Gd-Uptake & Gd-Predicted | 0±0 | 0±0 | 0±0 | 0±0 |
| | | Non-Tumor | Gd-Uptake & T1W | 0±0 | 0±0 | 0±0 | 0±0 |
| | | | Gd-Uptake & Gd-Predicted | 0±0 | 0±0 | 0±0 | 0±0 |

Figure 25

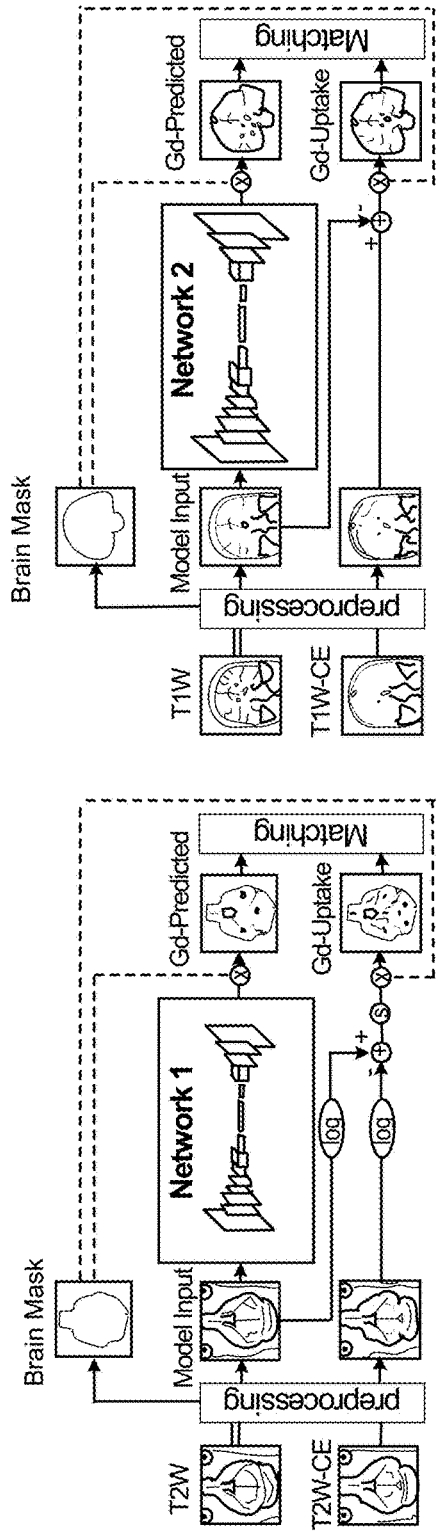
Figure 26A
Figure 26B
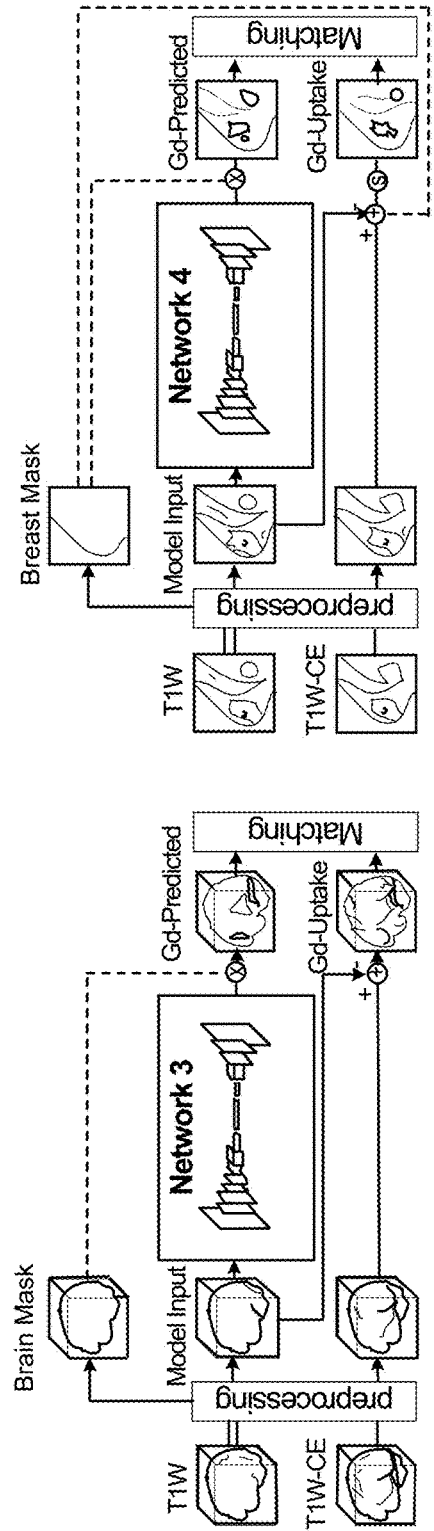
Figure 26C
Figure 26D

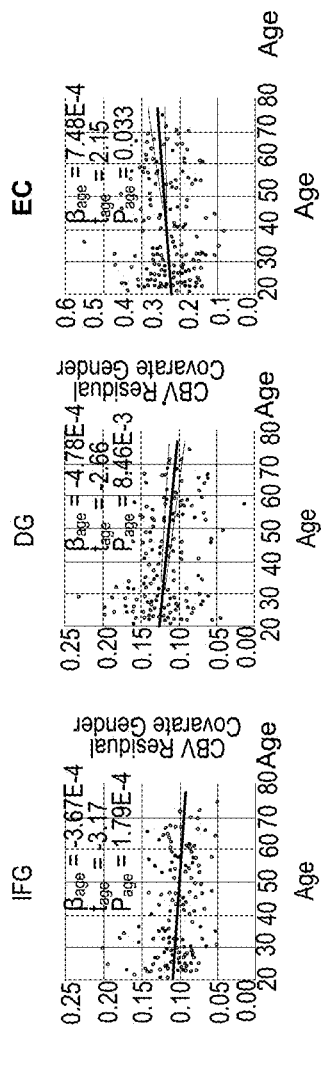
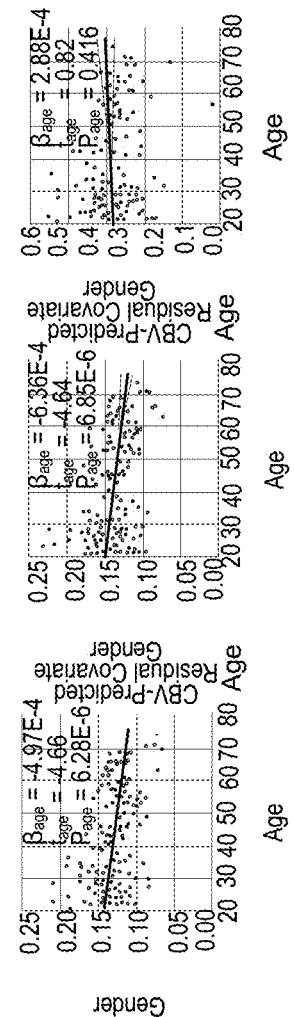
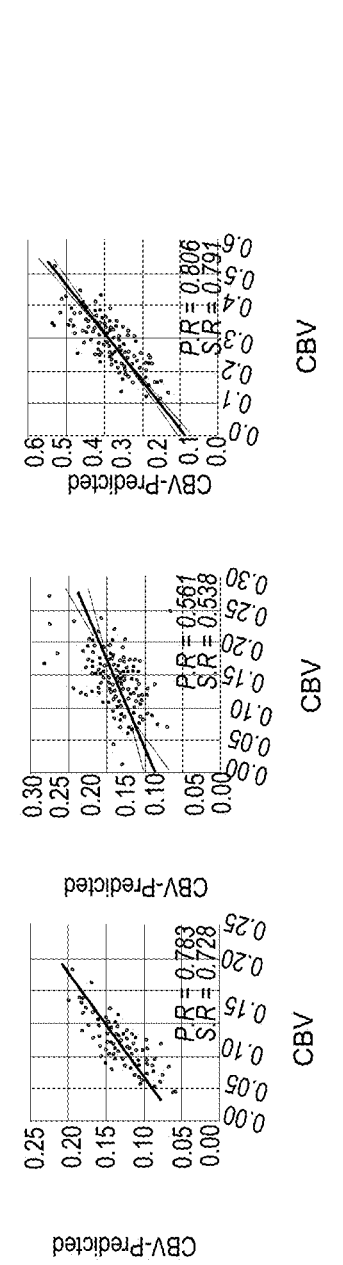
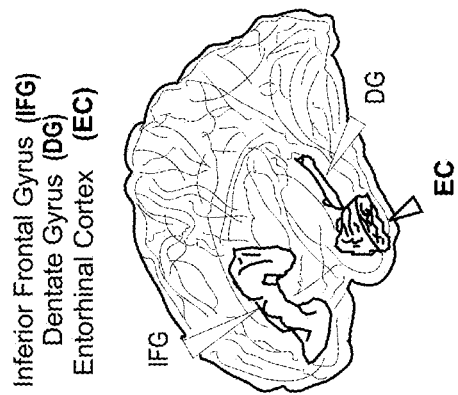
Figure 32A
Figure 32B
Figure 32C
Figure 32D

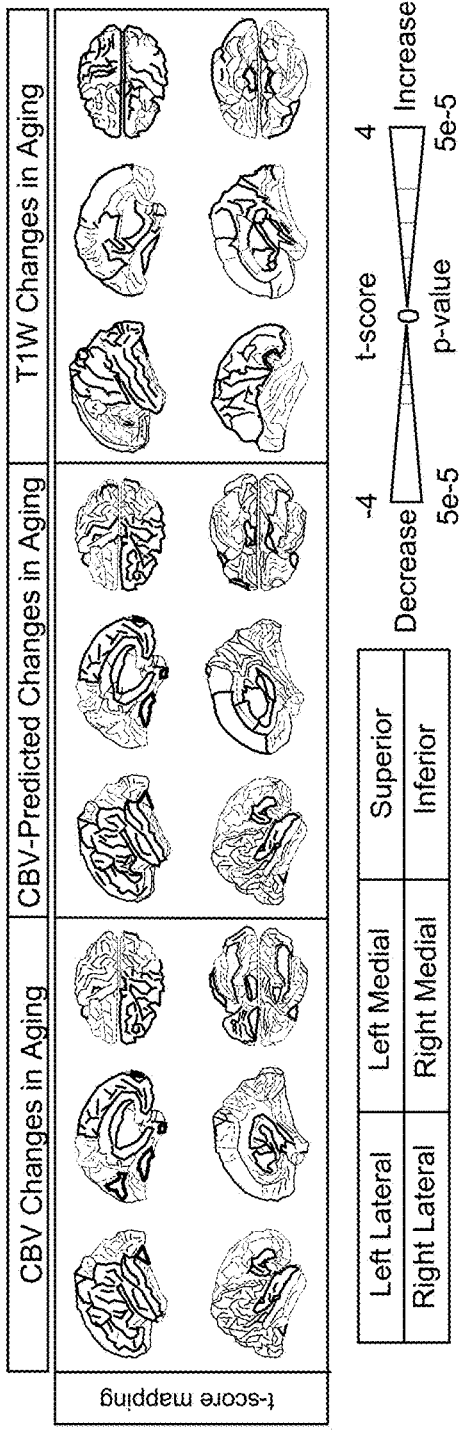
Figure 33A
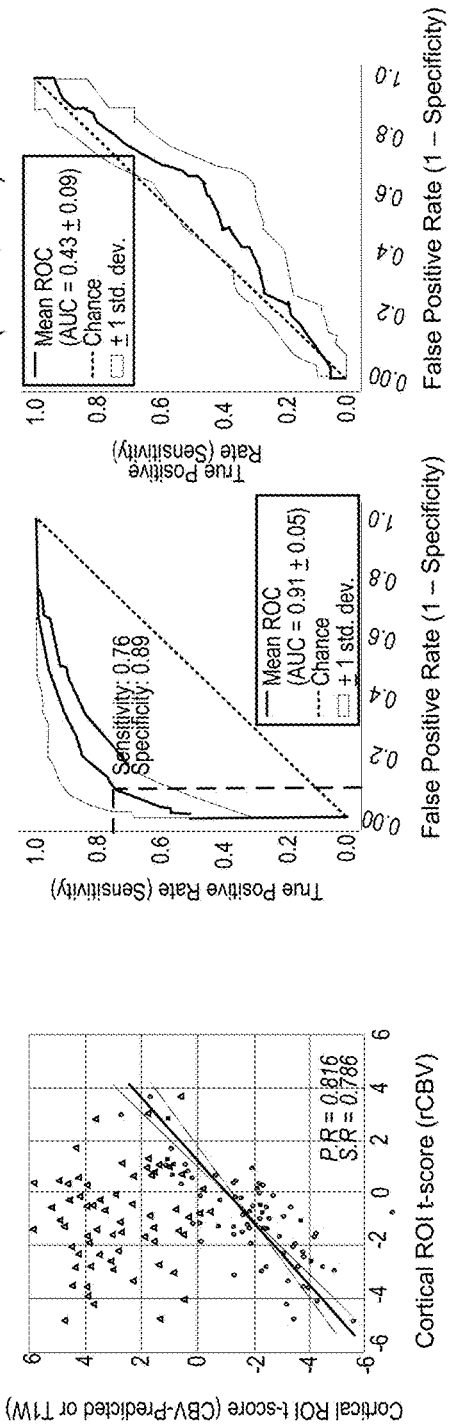
Figure 33C
Figure 33B

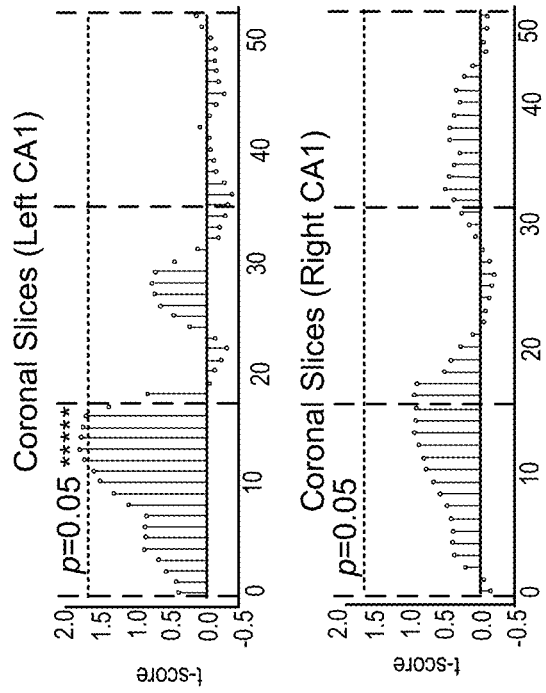
Figure 34B
Figure 34C
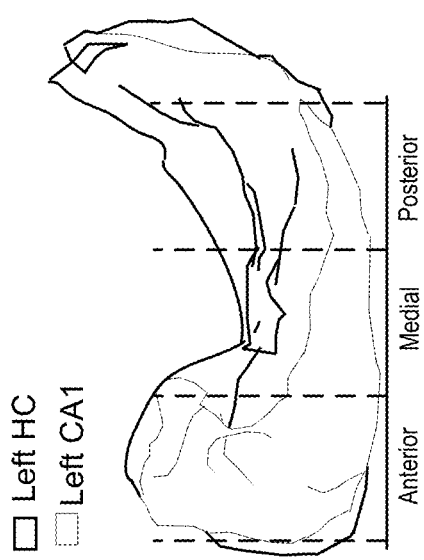
Figure 34A

| Dataset | Full Project Name | Disease/Category | Source |
|---|---|---|---|
| 4RTNI | 4-Repeat Tauopathy Neuroimaging Initiative | Tauopathic individuals | https://nerad.tu.edu/resource_4rtni.html |
| ABCD | Adolescent Brain Cognitive Development | long-term study of brain development and child health | https://nda.nih.gov/abcd |
| ABIDE | The Autism Brain Imaging Data Exchange | Autism spectrum disorder (ASD) | http://fcon_1000.projects.nitrc.org/indi/abide/ |
| ADNI | Alzheimer's Disease Neuroimaging Initiative | Alzheimer's disease | http://adni.loni.use.edu/ |
| Age ility | Age ility | Study structural and functional organization of brain networks | https://www.nitrc.org/projects/age_ility |
| AIBL | The Australian Imaging Biomarkers & Lifestyle Flagship Study of Ageing | Normal aging | https://aibl.csiro.au/research/neuroimaging/ |
| ATAG | Atlasing of the Basal Ganglia | 7T structural MRI scans | https://www.nitrc.org/projects/atag_mri_scans/ |
| ATLAS | Anatomical Tracings of Lesions After Stroke | Stroke | http://fcon_1000.projects.nitrc.org/indi/retro/atlas.html |
| BGST | Brain Genomics Superstruct Project | relationship between brain and behavior | https://www.neuroinfo.org/gsp |
| BND | Bipolar Disorder Neuroimaging Database | Bipolar disorder | https://sites.google.com/site/bipolardatabase/ |
| Brain Correlates of Math Development | Brain Correlates of Math Development | Brain correlates of math development | https://openneuro.org/datasets/ds001486/versions/1.2.1 |
| BraTS | Brain Tumor Segmentation | Glioblastoma | https://www.med.upenn.edu/cbica/brats2020/ |
| Cam-CAN | Cambridge Centre for Ageing and Neuroscience | How individuals can best retain cognitive abilities into old age | https://www.cam.can.org/index.php?content- |
| CoRR | Consortium for Reliability and Reproducibility | Test-retest reliability and reproducibility for functional and structural connectomics | http://fcon_1000.projects.nitrc.org/indi/CoRR/html/ |
| DLBS | Dallas Life-span Brain Study | Understand the antecedents of preservation and decline of cognitive function at different stages | http://fcon_1000.projects.nitrc.org/ikncid/retro/dlbs.html |
| IXI | Information eXtraction from Images | Healthy normal subjects | https://brain-development.org/ixi-dataset/ |
| MaND | Major Depressive Disorder Neuroimaging Database | Major depressive disorder | https://sites.google.com/site/depressiondatabase/ |
| NEUROCON | N/A | Parkinson's disease | https://fcon_1000.projects.nitrc.org/indi/retro/parkinsons.html |
| NIFD/FTLDNI | Frontotemporal Lobar Degeneration Neuroimaging Initiative | Frontotemporal lobar degeneration | https://ida.loni.usc.edu/collaboration/access/appLicense.jsp |
| OASIS | Open Access Series of Imaging Studies | Alzheimer's disease | https://www.oasis-brains.org/ |
| PAIN | Pain and Interoception Imaging Network | Persistent, pain disorders | https://www.painrepository.org/repositories/ |
| PPMI | Parkinson's Progression Markers Initiative | Parkinson's Disease | https://www.ppmi-info.org/access-data-specimens/download-data/ |
| SALD | Southwest University Adult life-span Dataset | Normal aging | http://fcon_1000.projects.nitrc.org/indi/retro/sald.html |
| SchizConnect | Large-Scale Schizophrenia Neuroimaging Data Mediation & Federation | Schizophrenia and bipolar disorder | http://schizconnect.org |
| SLIM | Southwest University Longitudinal Imaging Multimodal Brain Data Repository | Young healthy adults | http://fcon_1000.projects.nitrc.org/indi/retro/southwestuni_qiu_index.html |
| TanWn | Functional Connectivity of Cortical Motor Areas in the Resting State in Parkinson's Disease | Parkinson's disease | http://fcon_1000.projects.nitrc.org/indi/retro/parkinsons.html |
| QIN-BRAIN-DSC-MRI | N/A | Low and high grade glial brain lesions | https://wiki.cancerimagingarchive.net/display/public/QIN_BRAIN_DSC_MRI |
| RIDER NEURO MRI | N/A | Recurrent glioblastoma | https://wiki.cancerimagingarchive.net/display/public/RIDER|NEURO|MR| |

Figure 35

SYSTEM, METHOD AND COMPUTER-ACCESSIBLE MEDIUM FOR DETECTING STRUCTURAL DISORDER(S) USING MAGNETIC RESONANCE IMAGING

CROSS-REFERENCE TO RELATED APPLICATION(S)

This application is a continuation application of U.S. patent application Ser. No. 17/000,904 filed on Aug. 24, 2020, and also relates to and claims priority from U.S. Patent Application No. 62/890,868, filed on Aug. 23, 2019, U.S. Patent Application No. 62/977,018, filed on Feb. 14, 2020, and U.S. Patent Application No. 63/048,937, filed on Jul. 7, 2020, the entire disclosures of all of which are incorporated herein by reference.

FIELD OF THE DISCLOSURE

The present disclosure relates generally to magnetic resonance imaging ("MRI"), and more specifically, to exemplary embodiments of an exemplary system, method and computer-accessible medium for the reduction of the dosage of Gd-based contrast agent in MRI.

BACKGROUND INFORMATION

MRI is a tool used in clinical practice for the care of patients. The utility of this diagnostic imaging modality has expanded due to the addition of gadolinium ("Gd") based contrast agent, which has expanded its utilization. The role of Gd based contrast for MRI imaging can be largely divided into four major categories: (i) morphologic imaging; (ii) steady-state imaging; (iii) perfusion imaging and (iv) contrast-enhanced MR angiography, which can be used in the brain and other parts of the body. (See, e.g., Reference 1). Specifically, Gd-enhanced MRI can be routinely used to better visualize nearly all neurological disease—including strokes, tumors, infections, and neuroinflammation. Moreover, since Gd-enhanced MRI can generate high resolution maps of cerebral blood volume ("CBV") and cerebral blood flow ("CBF"), both tightly coupled to brain metabolism, Gd-enhanced MRI can be used as a fMRI tool. (See, e.g., Reference 28). In fact, the use of Gd-enhancement was the first fMRI study published. (See, e.g., Reference 40). More recently, because it can be used to generate CBV maps that are both quantitative and has submillimeter resolution, this CBV-fMRI approach has been used to detect the earliest stages of Alzheimer's disease (see, e.g., Reference 11), schizophrenia (see, e.g., Reference 41), and to map the effects of normal aging has on the exemplary brains. (See, e.g., Reference 10).

Despite its significant advantages, Gd-enhanced MRI requires an intravenous ("IV") injection. Recently, reports of gadolinium retention in the brain and body after previous exposure to gadolinium based contrast agents ("GBCAs") has brought serious safety concerns in the clinical community. (See, e.g., Reference 2). It is known that GBCAs cannot be administered to certain patients, such as patients with renal insufficiency that cannot filter the gadolinium from their body. (See, e.g., Reference 3). Studies have also shown that GBCAs deposition can be independent of renal function (see, e.g., Reference 4) and higher dosage GBCAs can link to diseases, such as nephrogenic systemic fibrosis ("NSF") development. (See, e.g., Reference 5). Particularly, patients who need repeated contrast administration (e.g., multiple sclerosis and breast cancer screening) are at the highest risk.

Further, in 2017, the Medical Imaging Drugs Advisory Committee ("MIDAC") of the FDA recommended adding a warning to labels about gadolinium retention in various organs and issued a safety announcement requiring a new class warning and other safety measures for all GBCAs used for MRI.

Since then the acceptance of GBCA-free procedures has increased in clinical MRI. (See, e.g., Reference 1). A number of methods focusing on GBCA-free perfusion and angiography for brain MRI have been developed, including time-of-fly ("TOF") angiography, black blood imaging, arterial spin labeling ("ASL") and vascular-space-occupancy ("VASO"), which magnetically 'label' protons in the patient's inflowing blood, thereby removing the need for injection of an exogenous contrast agent. (See, e.g., Reference 6). Multiparametric MRI is another alternative to GBCAs, and some multiparametric MRI methods are already widely used in clinical practice. (See, e.g., Reference 7).

Alternatively, there are specific MRI procedures that cannot be performed with GBCA-free procedures. (See, e.g., References 8-13). These include MRI imaging to assess neurometabolism, microvascular flow and integrity, and leakiness. Thus, there is an urgent need to develop alternative imaging techniques that reduce the dose of Gd to prevent Gd retention and preserve useful Gd-enhanced contrast information.

Thus, it may be beneficial to provide an exemplary system, method, and computer-accessible medium for the reduction of the dosage of Gd-based contrast agent in MRI, which can overcome at least some of the deficiencies described herein above.

SUMMARY OF EXEMPLARY EMBODIMENTS

An exemplary system, method, and computer-accessible medium for generating a gadolinium ("Gd") enhanced map(s) of a portion(s) of a patient(s), can include, for example, receiving magnetic resonance imaging (MRI) information of the portion(s), and generating the Gd enhanced map(s) based on the MRI information using a machine learning procedure(s). The Gd enhanced map(s) can be a full dosage Gd enhanced map. The full dosage Gd enhanced map(s) can be a full dosage Gd enhanced cerebral blood volume map(s). The machine learning procedure can be a convolutional neural network. The MRI information can include (i) a low-dosage Gd MRI scan(s), or (ii) a Gd-free MRI scan(s). A Gd contrast can be generated in the Gd enhanced map(s) using a T2-weighted MRI image of the portion(s).

In some exemplary embodiments of the present disclosure, the machine learning procedure(s) can include an attention unit(s) and a residual unit(s). The machine learning procedure(s) can include at least five layers. The machine learning procedure(s) can include a contraction path(s) configured to encode a high resolution image(s) into a low resolution representation(s). The machine learning procedure(s) can include an expansion path(s) configured to decode the low resolution representation(s) into a further high-resolution image(s). The machine learning procedure(s) can include at least five encoding layers and at least five decoding layers. Each of the at least five encoding layers and each of the at least five decoding layers can include a residual connection.

In certain exemplary embodiments of the present disclosure, Each of the at least five encoding layers and each of the at least five decoding layers can include two series of 3×3 two-dimensional convolutions. Each of the at least five encoding layers can be followed by a 2×2 max-pooling layer, and (ii) each of the at least five decoding layers can be followed by at least one 2×2 upsampling layers. The machine learning procedure(s) can include max-pooling and upsampling, and the max-pooling and the upsampling can each be performed using a factor of 2. The machine learning procedure(s) can include a batch normalization layer(s) and a rectified linear unit layer(s). The portion(s) can be a section(s) of a brain of the patient(s).

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIG. 6A is a set of exemplary images illustrating Ground truth and DeepCBV predictions and 20% low-dosage CBV map of one slice under the same threshold according to an exemplary embodiment of the present disclosure;

FIG. 6B is a set of exemplary graphs illustrating quantitative comparisons for MSE, SSIM, P.R$^2$, S.R$^2$, and PSNR between the two input's DeepCBV results and the 20% low-dosage result according to an exemplary embodiment of the present disclosure;

FIG. 14A is a set of exemplary steady-state CBV maps according to an exemplary embodiment of the present disclosure;

FIG. 14B is a set of exemplary charts illustrating a comparison between the exemplary DeepContrast ad a 20% low-dose CBV according to an exemplary embodiment of the present disclosure;

FIG. 14C is a set of exemplary images of tumor regions according to an exemplary embodiment of the present disclosure;

FIG. 14D is a set of exemplary charts illustrating comparisons between the exemplary DeepContrast results and a 20% low-dose CBV according to an exemplary embodiment of the present disclosure;

FIG. 21A is a set of exemplary images of the exemplary DeepContrast prediction according to an exemplary embodiment of the present disclosure;

FIGS. 21B-21E are exemplary graphs illustrating a comparison between the exemplary Deep Contrast prediction and the ground truth according to an exemplary embodiment of the present disclosure;

FIG. 21F is a set of exemplary graphs illustrating a tumor segmentation receiver operating characteristic curve according to an exemplary embodiment of the present disclosure;

FIG. 23A is an exemplary three-dimensional rendering and a set of images of the of the bilateral hippocampal formation according to an exemplary embodiment of the present disclosure;

FIGS. 23B-23D are sets of CBV-predicted maps and coronal slices on which the hippocampal formation mask was applied according to an exemplary embodiment of the present disclosure;

FIG. 23E is an exemplary scatter plot illustrating the association between age and mean CBV-Predicted values from the dentate gyrus according to an exemplary embodiment of the present disclosure;

FIG. 23F is an exemplary box plot illustrating individual-subject mean CBV-Predicted values in the left anterior CA1 according to an exemplary embodiment of the present disclosure;

FIG. 23G is an exemplary box plot illustrating individual-subject mean CBV-Predicted values in the right transentorhinal cortex according to an exemplary embodiment of the present disclosure;

FIG. 25 is an exemplary table providing quantitative evaluations of the exemplary Deep Contrast models according to an exemplary embodiment of the present disclosure;

FIGS. 26A-26D are exemplary diagrams illustrating various exemplary trainings of the exemplary DeepContrast models according to an exemplary embodiment of the present disclosure;

FIG. 32A is an exemplary three-dimensional rendering of the inferior frontal gyrus, dentate gyrus, and entorhinal cortex overlaid on a group-wise T1-weighted MRI template according to an exemplary embodiment of the present disclosure;

FIGS. 32B and 32C are sets of exemplary age-related regressions of cerebral blood volume maps according to an exemplary embodiment of the present disclosure;

FIG. 32D is a set of scatter plots of the region of interest-mean CBV vs. CBV-Predicted values according to an exemplary embodiment of the present disclosure;

FIG. 33A is a set of exemplary three-dimensional volume renderings of the age-related t-score maps according to an exemplary embodiment of the present disclosure;

FIG. 33B is an exemplary scatter plot of the age-related t-score according to an exemplary embodiment of the present disclosure;

FIG. 33C is a set of exemplary graphs illustrating an analysis of the concordance to CBV t-scores according to an exemplary embodiment of the present disclosure;

FIG. 34A is an exemplary three-dimensional rendering of the left CA1 overlaid on the left hippocampus, built from a group-wise T1-weighted MRI template according to an exemplary embodiment of the present disclosure;

FIGS. 34B and 34C are exemplary slice-based two-sample t-test results for each coronal slice along the anterior-posterior axis of the left (see e.g., FIG. 15B) and right (see e.g., FIG. 15C) CA1 according to an exemplary embodiment of the present disclosure;

FIG. 35 is an exemplary table of public brain magnetic resonance imaging databases according to an exemplary embodiment of the present disclosure; and FIG. 36 is an illustration of an exemplary block diagram of an exemplary system in accordance with certain exemplary embodiments of the present disclosure.

Figure 1:
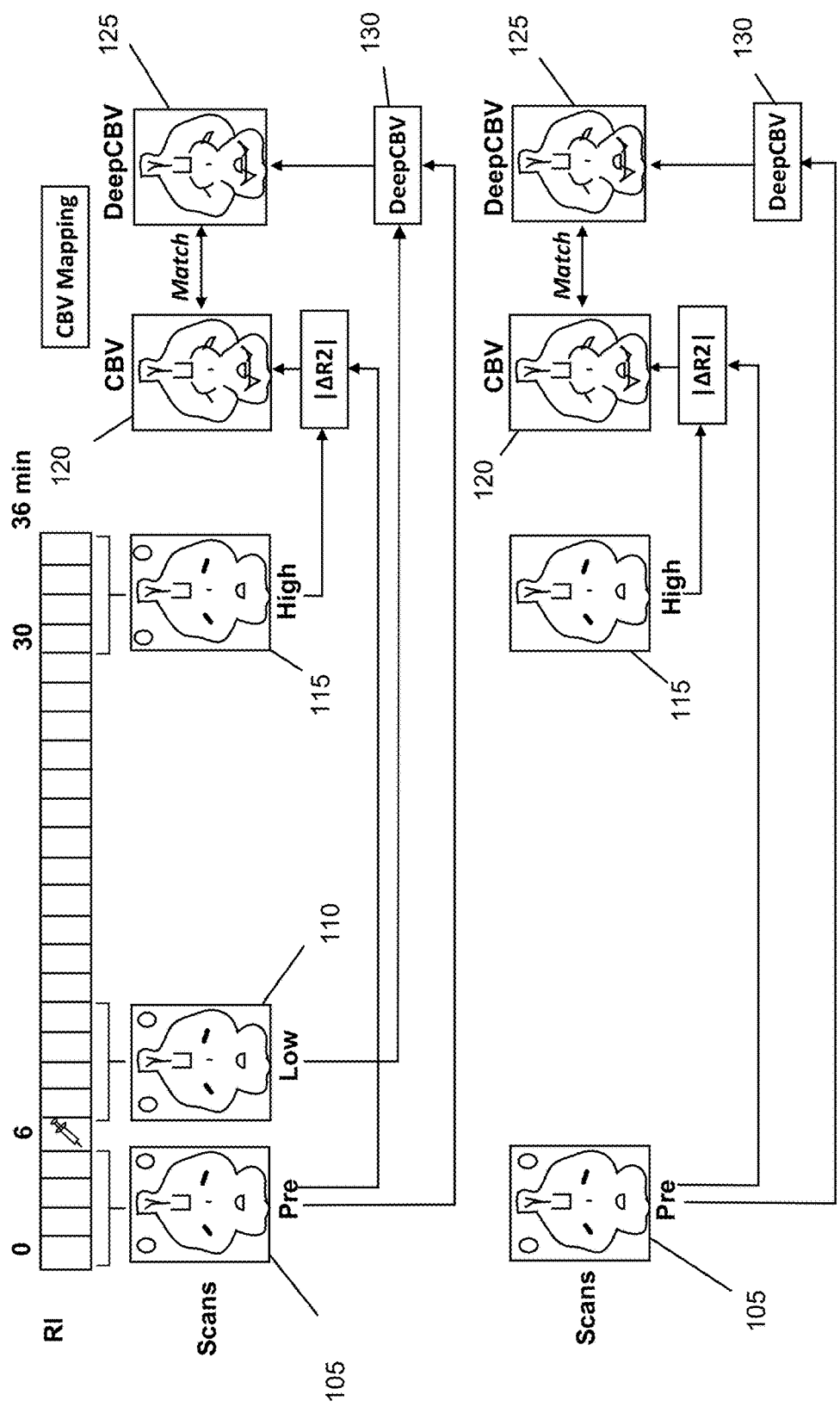
FIG. 1 is an exemplary diagram illustrating a T2 weighted MRI acquisition and the generation of a ΔR2 map according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EXEMPLARY EMBODIMENTS

Procedures that can estimate high-quality Gd contrast directly from the low-dosage or Gd-free scans can be beneficial. Recently, deep learning methods have shown great potential in dosage reductions in medical imaging which can facilitate less radiotracer used in PET (see, e.g., Reference 14), lower X-ray exposure in CT (see, e.g., Reference 15) and lower Gd dosage in MRI for glioma enhancement. (See, e.g., Reference 16). Using artificial intelligence, a full dosage Gd-enhancement can be estimated using reduced Gd. The exemplary system, method and computer-accessible medium, according to an exemplary embodiment of the present disclosure, can utilize a residual attention U-Net architecture to estimate full dosage Gd-enhanced CBV maps from 20% Gd dosage MRI and further to produce Gd contrast directly from T2-weighted ("T2W") MRI while preserving high image quality and contrast information. The exemplary model was tested in both CBV fMRI scans acquired from lab animals (i.e., wild-type C576J/BL ("WT") mice and a Glioblastoma ("GBM") mouse model) and human subjects.

Exemplary Material and Methods

Exemplary Animal Subject: Mice used in the exemplary study included two groups: WT mice and mice with GBM. The WT group contains 51 healthy adult C576J/BL male mice scanned at 12-14 months age range. The GBM group contains 10 adult C576J/BL male mice which were injected with PDGFB(+/+) PTEN(−/−) p53(−/−) GBM cells). Mice GBM cells express molecular markers similarly to human proneural GBM cells. 50,000 cells in 1 μL were stereotactically injected into the brain. MRI scans of GBM mice were obtained 10 days after injection.

Exemplary Human Dataset: MRI scans of human subjects used in the exemplary study included 599 steady-state Gd-enhanced CBV fMRI scans acquired at 3T across multiple sites, vendors, and time points. (See, e.g., References 10, 11, 28 and 41).

Exemplary MRI Acquisition for Animal: For each mouse subject, T2-weighted ("T2W") MRI scans were acquired using a two-dimensional ("2D") T2-weighted Turbo Rapid Acquisition with Refocused Echoes ("RARE") sequence (e.g., TR/TE=3500/45, RARE factor=8, 76 μm in-plane resolution, 450 μm slice thickness) at 9.4T (e.g., Bruker Biospec 94/30 USR equipped with CryoProbe). FIG. 1 shows is an exemplary diagram illustrating a T2 weighed MRI acquisition and the generation of a $\Delta R2$ map 120 according to an exemplary embodiment of the present disclosure. 25 consecutive scans were collected consecutively for 36 minutes, and Intraperitoneal ("IP") injection of Gadodiamide at 10 mmol/kg was administered to the mouse 6 minutes after the initial scan was taken. The first 4 scans were averaged to generate the contrast-free scan ("Pre") 105, while the low-dosage scan ("Low") 110 and full-dosage scan ("High") 115 were generated by averaging the 6th to 9th scans and the 33rd to 36th scans, respectively. The gadolinium uptake by the mouse can reach its steady state maximum, (e.g., full-dosage) at around 30 minutes after IP injection, or in other words, 36 minutes after the initial scan. The uptake can reach approximately 20% of the full-dosage at 4 minutes after IP injection, or 10 minutes after the initial scan.

Exemplary MRI Acquisition for Human Subject: For the CBV-fMRI 125 shown in FIG. 1, a steady-state contrast enhanced CBV procedure 130 was used. (See, e.g., References 10 and 11). MRI scans were acquired with a Philips Achieva 3.0 T MRI scanner using an 8-channel SENSE head coil. In each scan session, a T1-weighted structural scan (TR=6.7 ms, TE=3.1 ms, field of view ("FOV")=240×240× 192 mm$^3$, voxel size=0.9×0.9×0.9 mm$^3$) was first acquired using a Turbo Field Echo ("TFE") gradient echo ("GRE") sequence; a pair of un-scaled T1-weighted images (TR=7 ms, TE=3 ms, FOV=240×240×162 mm$^3$, voxel size=0.68× 0.68×3 mm$^3$) were acquired afterwards with a bolus injection of gadolinium contrast agent in between.

Exemplary Data Preprocessing for Animal: The raw scans from the Bruker scanner were converted to NIfTI format, and for each subject, rigid-body spatial normalization was used to align the Pre scan 105, the Low scan 110, and the High scan 115. After that, brain extraction using brain masks (e.g., binary maps) was completed using PCNN3D. (See, e.g., Reference 17). As shown in FIG. 1, relative CBV ground-truth were generated as the $\Delta R2$ maps using the Pre scan 105 and the High scan 115. (See, e.g., Reference 8)). The low-contrast CBV were also generated as the $\Delta R2$ using Pre and Low scans, which were later used as baselines for comparison. For scans of tumor subjects, ground truth tumor masks were generated in addition to the brain masks using the FCM (e.g., Fuzzy-C-Means) Clustering Based Segmentation. (See, e.g., Reference 18).

Exemplary Data Preprocessing for Human: The T1-weighted structural images were processed using Free-Surfer, generating cortical parcellation (see, e.g., References 42 and 43) and hippocampal subregions segmentation (see, e.g., Reference 44) in the individual space. The primary hippocampal subregions labeled include presubiculum ("PRESUB"), subiculum ("SUB"), CA1, CA3, CA4 (e.g., hilus), granule cell molecular layer of DG ("DG"), molecular layer of subiculum and CA fields ("MLSUBCA"). The list of cortical regions can be found in the parcellation protocol. (See, e.g., Reference 42).

CBV-fMRI processing followed the previous exemplary procedures (see, e.g., References 10 and 11) and included registration of the pre-contrast and the post-contrast T1-weighted scans, subtraction of the co-registered post-contrast and pre-contrast scans, and CBV value normalization with the top 5% mean signal of the whole head regions. The raw CBV values are % CBV measures in a unit voxel.

Individual structural images were registered into template space with affine registration. Individual CBV images were linearly registered into the individual structural image space. The CBV images were registered to the template space with the transformation field composed of the affine transformation matrix. In region-of-interest ("ROI") analyses, mean CBV measures the average amount of cerebral blood volume in an anatomically defined ROI.

Exemplary Deep Learning Model: As shown in FIG. 1, an exemplary deep learning network was used to estimate the ground-truth CBV from the Pre+Low scans and the Pre scan only respectively. The former corresponded to a 5-fold reduction of Gd dosage for CBV map generation and the latter corresponded to completely moving away from Gd. Gd contrast can be produced directly from Gd-free MRI scans and high image quality and contrast information in CBV fMRI can be preserved. In an exemplary mouse study, both wild-type ("WT") mice and mice with Glioblastoma ("GBM") at 9.4T were used. The exemplary DeepCBV procedure was then tested on a human dataset that included 599 steady-state Gd-enhanced CBV fMRI scans acquired at 3T across multiple sites, vendors, and time points. (See, e.g., References 10, 11, 28 and 41).

Figure 2:
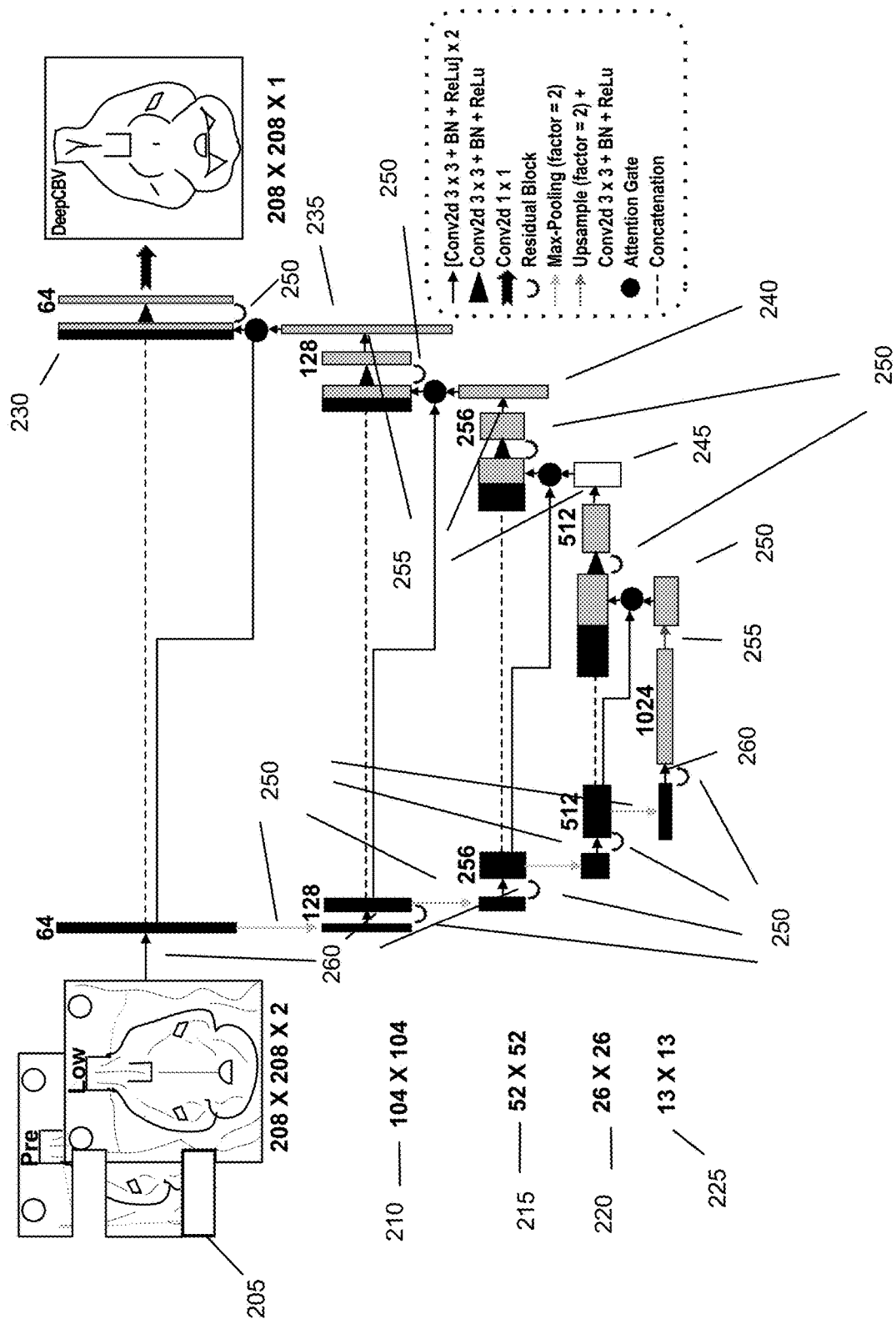
FIG. 2 is an exemplary diagram illustrating the exemplary ResAttU-Net architecture according to an exemplary embodiment of the present disclosure.

The performance of the U-Net with only attention units ("AttU-Net"), U-Net with only residual units ("ResU-Net") and the U-Net with both residual and attention unit ("ResAttU-Net") were analyzed with the input of Pre+Low image. The exemplary deep learning architecture included the out-stand five-layer ResAttU-Net as illustrated in FIG. 2. In particular, FIG. 2 shows an exemplary diagram illustrating the exemplary ResAttU-Net architecture according to an exemplary embodiment of the present disclosure. The exemplary ResAttU-Net architecture includes a contraction path that can encode high resolution data into low resolution representations, and an expansion path that can decode such encoded representations back to high-resolution images. The exemplary ResAttU-Net was applied to further evaluate the necessity of the Low image inputting during to experiment, and to evaluate whether it can be possible that the exemplary deep learning approach can derive the CBV map directly from the Pre image only. The exemplary system, method, and computer-accessible medium can utilize sophisticated tumor data for the clinical application, which is described below.

As shown in FIG. 2, the exemplary architecture of ResAttU-Net can include of 5 encoding layers 205, 210, 215, 220, and 225 and 5 decoding layers 230, 235, 240, 245, and 250. All the layers can include a residual connection 250; the decoding layers 230-250 can be implemented with attention mechanism. Various Max-pooling can be performed (e.g., with a factor of 2) as well as upsampling 255 also with a factor of 2. Additionally, Conv2D+Batch Normalization ("BN")+Rectified Linear Unit ("ReLu") layers 260 can be included. The exemplary network can take both Pre and Low as the two-channel input or only Pre as the single-channel input. Estimated 2D CBV maps with brain extraction can be the output.

The exemplary study included 51 WT mice scans, with a 39-6-6 train-validation-test split. 4 mice with GBM, in addition to the WT mice, were included. 599 human scans were used in the study, with a 326-93-180 train-validation-test split. Randomization was performed at the subject level to prevent the images from the same subject data overlapping across sets.

Exemplary Evaluation and Statistical Analysis: To evaluate the exemplary system, method, and computer-accessible medium, the mean square error ("MSE") and peak signal to noise ratio ("PSNR") were used to assess the estimation error on voxel level, and the structural similarity index ("SSIM"), Pearson correlation coefficient, and Spearman correlation coefficient to evaluate the accuracy of estimation on the structural level. In addition to these quantitative analysis procedures, a Dice similarity coefficient and Hausdorff distance were utilized evaluate the tumor model results. (See, e.g., Reference 19).

Exemplary MSE

Given a reference image f and a test image g, both of size M×N, the MSE (see, e.g., Reference 20) between f and g can be defined by, for example:

$$MSE(f, g) = \frac{1}{MN}\sum_{i=1}^{M}\sum_{i=1}^{N}(f_{ij} - g_{ij})^2$$

Exemplary PSNR

The exemplary PSNR (see, e.g., Reference 20) between f and g can be defined by, for example:

$$PNSR(f, g) = 10\log_{10}\left(\frac{255^2}{MSE(f, g)}\right)$$

Exemplary SSIM

The exemplary SSIM (see, e.g., Reference 20) between f and g can be defined by, for example:

$$SSIM(f, g) = l(f, g)c(f, g)s(f, g) \text{ where } \begin{cases} l(f, g) = \frac{2\mu_f\mu_g + C_1}{\mu_f^2 + \mu_g^2 + C_1} \\ c(f, g) = \frac{2\sigma_f\sigma_g + C_2}{\sigma_f + \sigma_g^2 + C_2} \\ s(f, g) = \frac{\sigma_{fg} + C_3}{\sigma_f\sigma_g + C_3} \end{cases}$$

Exemplary Pearson Correlation Coefficient ("PCC")

The exemplary PCC can be defined by, for example:

$$r_{xy} = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

Exemplary Spearman Correlation Coefficient ("SCC")

The exemplary SCC can be defined by, for example:

$$\rho = 1 - \frac{6\Sigma d_i^2}{n(n^2 - 1)}$$

where ρ can be the Spearman rank correlation; $d_i$ can be the difference between the ranks of corresponding variables; and n can be the number of observations.

Exemplary Dice Similarity Coefficient ("DSC")

The exemplary Dice similarity coefficient can be a simple but powerful method to quantify the spatial overlap. (See, e.g., Reference 39). In the exemplary case, X and Y can be the prediction and the ground truth respectively, and the DSC can be defined by, for example:

$$DSC = \frac{2|X \cap y|}{|X| + |y|}$$

Exemplary Hausdorff Distance ($d_H$)

The exemplary Hausdorff distance can facilitate the determination of the interval between two subsets of a metric space. (See, e.g., Reference 21). Same as DSC, let X and Y be the prediction and the ground truth of the tumor model. Thus, for example:

$$d_H(X,Y) = \max\{\sup_{x \in X} \inf_{y \in Y} d(x,y), \sup_{y \in Y} \inf_{x \in X} d(x,y),\}$$

Application to GBM Mouse Model: A tumor case was used to evaluate the exemplary CBV map. To further probe into the application of the deep learning network, 6 GBM mice scans were randomly added to the training set and the network was tested on other 4 GBM mice scans.

Exemplary Results

Figure 3A:
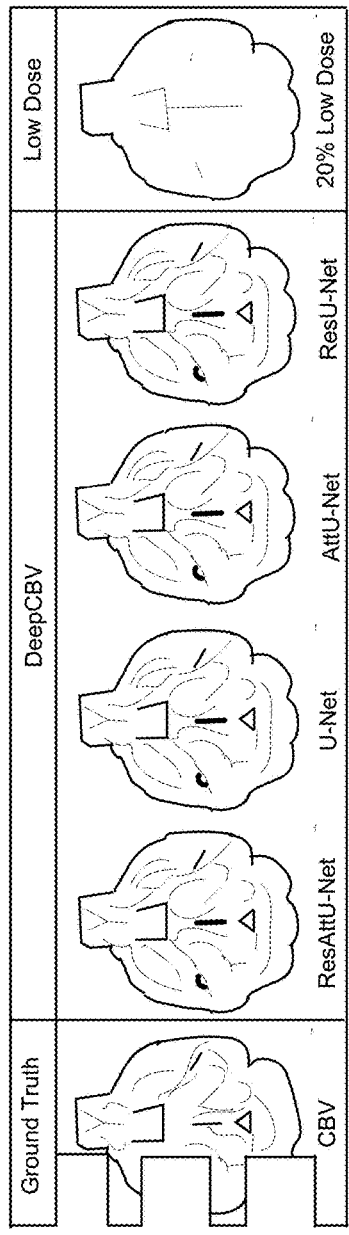
FIG. 3A is a set of exemplary images of Ground truth and DeepCBV predictions of four different U-Net architectures and 20% low-dosage CBV map of one slice under the same threshold according to an exemplary embodiment of the present disclosure.

Exemplary Quantitative Evaluations of Different U-net Architectures: Different U-net architectures' performance in CBV mapping contrast enhancement were analyzed. The results are shown in FIG. 3. In particular, FIG. 3A shows a set of exemplary images of Ground truth and DeepCBV predictions of four different U-Net architectures and 20% low-dosage CBV map of one slice under the same threshold according to an exemplary embodiment of the present disclosure. All four deep learning contrast results show strong enhancement compared to the 20% low-dosage CBV ΔR2. The similarity between predicted and real high contrast can be observed. This can be observed from the fine structure of hippocampus and cortex and the contrast between CSF and tissue.

Figure 3B:
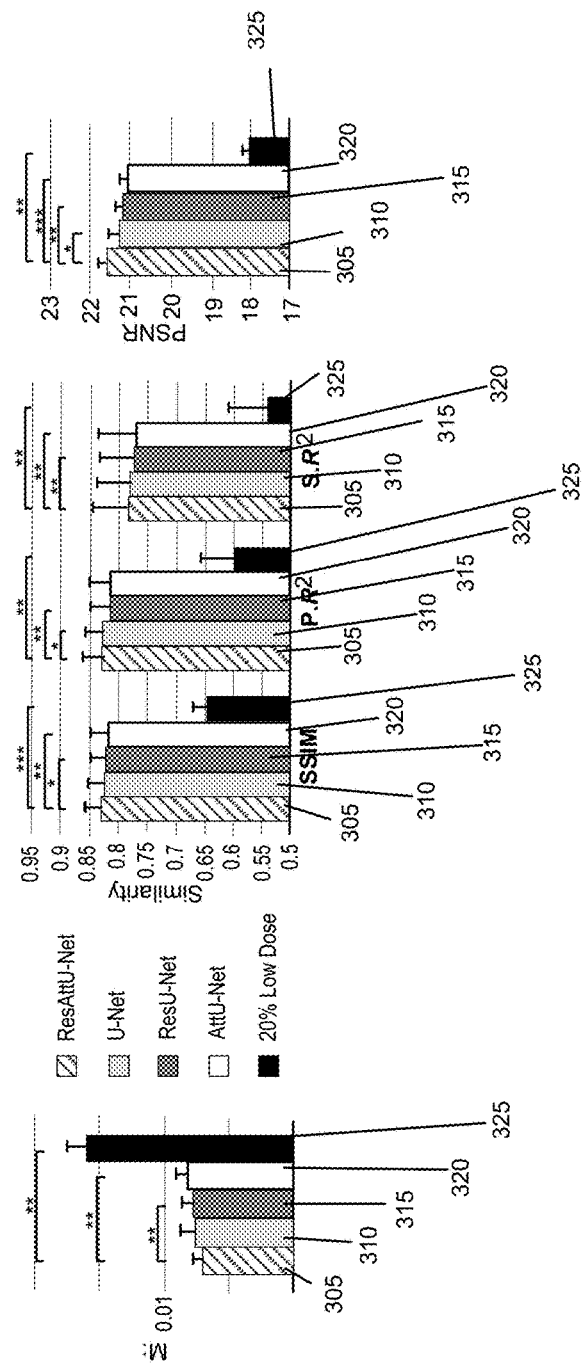
FIG. 3B is a set of exemplary graphs illustrating the comparison of MSE, SSIM, P.R$^2$, S.R$^2$, and PSNR according to an exemplary embodiment of the present disclosure.

FIG. 3B shows the MSE, SSIM, PSNR and Correlation Coefficients comparison between different U-net architectures' CBV estimation and 20% low-dosage CBV (e.g., for ResAttU-Net 305, U-Net 310, ResU-Net 315, AttU-Net 320, and 20% Low Dose 325). ResAttU-Net's 305 result shows the largest SSIM, PSNR, and Correlation Coefficients and the smallest MSE, indicating ResAttU-net's 305 best performance and potential for further objectives. Statistical analyses were performed using paired t-test. Values denote mean S.E.M. *P<0.05, P<0.01, *P<0.001. As shown in FIG. 3B, the exemplary ResAttU-Net outperforms all other architectures in all evaluations.

Figure 4C:
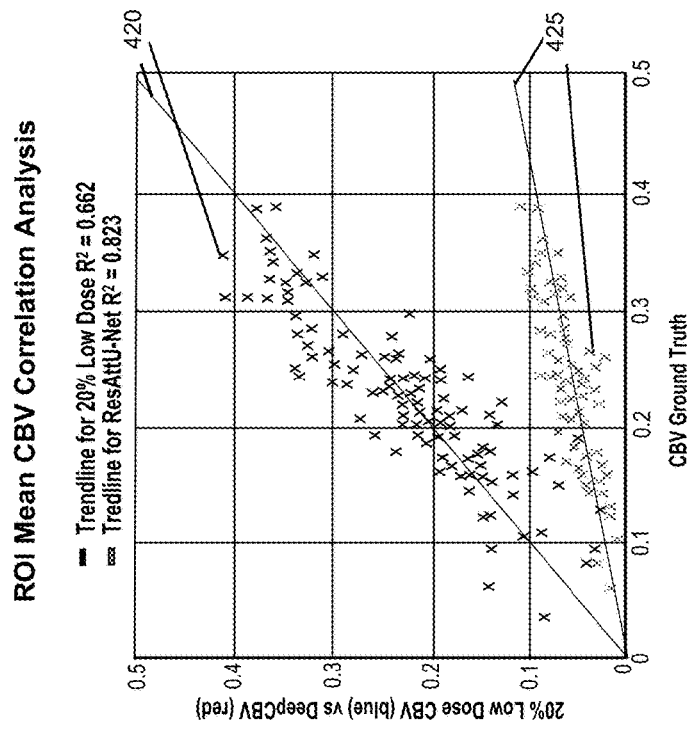
FIG. 4C is an exemplary graph illustrating the correlation analysis between the predicted results and 20% low-dosage CBV mapping according to an exemplary embodiment of the present disclosure.
Figure 4A:
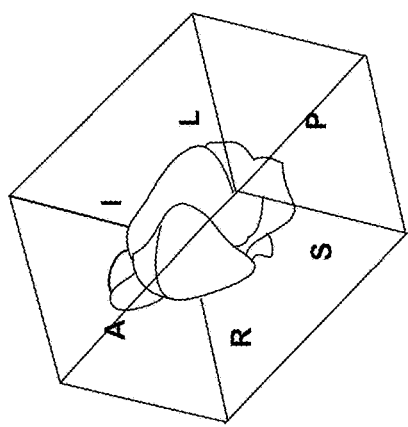
FIG. 4A is an exemplary diagram illustrating the visualization of region of interest segmentation according to an exemplary embodiment of the present disclosure.
Figure 4B:
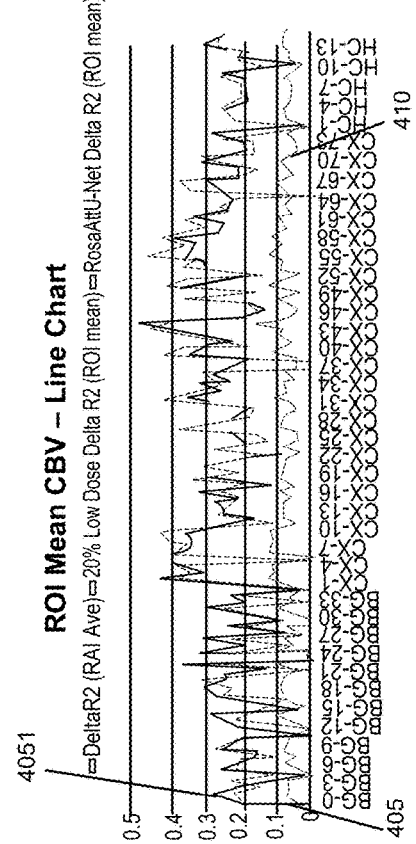
FIG. 4B is an exemplary line chart illustrating the region of interest ΔR2 of ground truth and ResAttU-Net's predictions and the 20% low-dosage CBV image according to an exemplary embodiment of the present disclosure.

In addition, one WT mouse was randomly chosen for the ROI evaluation. The mouse brain atlas, which is shown in the diagram of FIG. 4A, contains 75 ROIs in the cortex, 16 ROIs in the hippocampus, and 35 ROIs in the basal ganglia. FIG. 4B shows an exemplary diagram illustrating the visualization of region of interest segmentation according to an exemplary embodiment of the present disclosure. In particular, FIG. 4B shows the similarity of ROI CBV mean between ResAttU-Net Delta R2 405, the 20% Low Dose Delta 410, and the Delta R2 415. The exemplary ResAttU-Net predicted result matches the ground truth well. FIG. 4C illustrates an exemplary graph illustrating the correlation analysis between the predicted results and 20% low-dosage CBV mapping according to an exemplary embodiment of the present disclosure. In particular, as shown in FIG. 4C, the correlation coefficient of the ResAttU-Net's prediction 420, is better than the 20% low dosage ΔR2 map 425. The exemplary ResAttU-Net map shows much stronger similarity than the 20% low-dosage map compared to the CBV ground truth.

Exemplary Performance Evaluation of DeepCBV in Normal Brian CBV Mapping in Mice

Figure 5A:
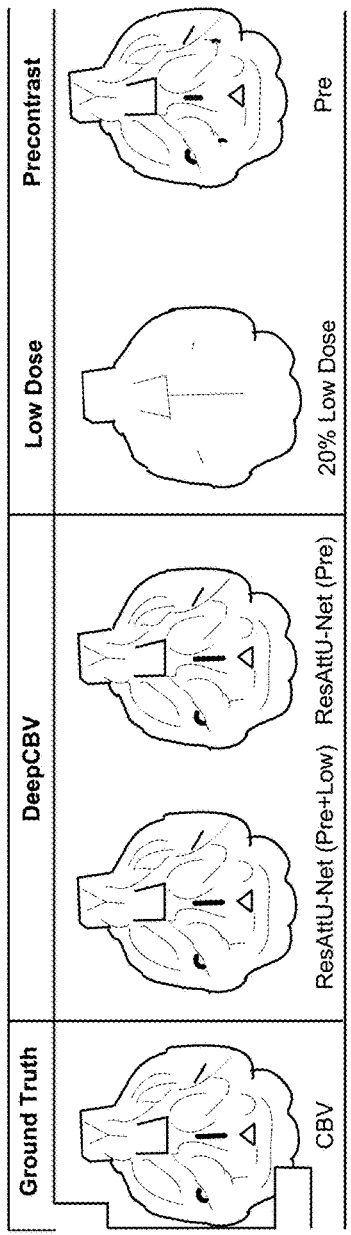
FIG. 5A is a set of exemplary images illustrating Ground truth and DeepCBV predictions and a 20% low-dosage CBV map of one slice under the same threshold according to an exemplary embodiment of the present disclosure.
Figure 5B:
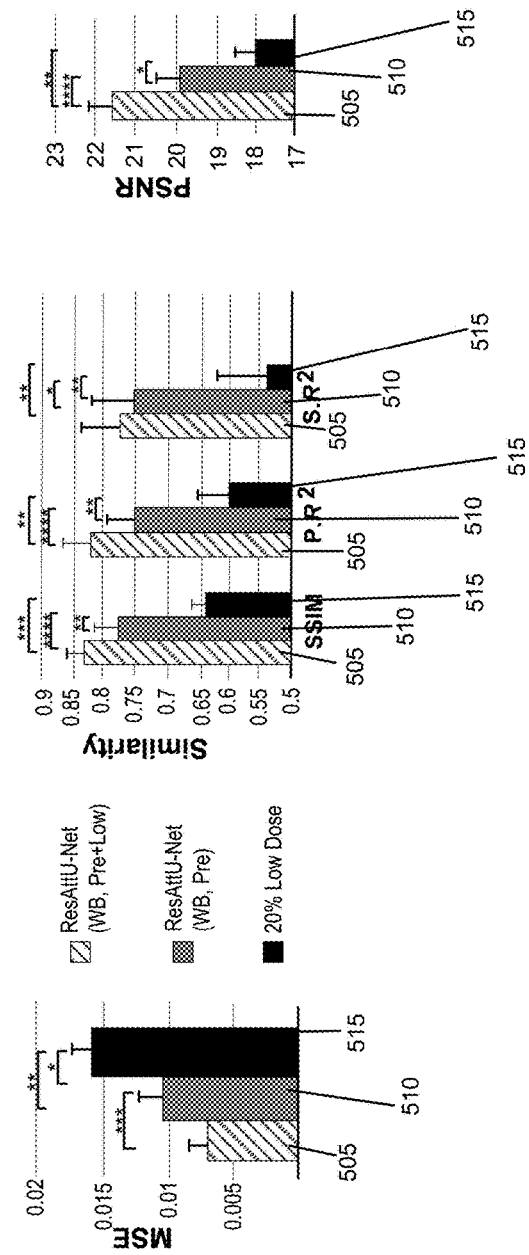
FIG. 5B is a set of exemplary graphs illustrating quantitative comparisons for MSE, SSIM, P.R$^2$, S.R$^2$, and PSNR between the two input's DeepCBV results and the 20% low-dosage result according to an exemplary embodiment of the present disclosure.

The exemplary ResAttU-Net was evaluated with input training data of just Pre image of WH to test whether it can be possible to derive the DeepCBV map without contrast agents. FIGS. 5A and 5B show the predictions and the statistic results of the Pre+Low and Pre compared with the 20% Low dose and Pre-contrast image. In particular, FIG. 5A shows the same slice from a subject. Pre image's deep learning contrast results show strong enhancement compared to the 20% low-dosage CBV ΔR2 and the Pre-contrast image. The similarity between the predictions of the two input conditions can be observed from the contrast enhanced hippocampus and cortex and the difference between CSF and tissue.

FIG. 5B shows the quantitative comparison of the predictions of Pre+Low (e.g., ResAttU-Net 505), Pre (e.g., ResAttU-Net 510), and 20% low-dosage (e.g., 20% Low Dose 515) CBV ΔR2. The results indicate that when the training data contains both Pre and Low image, the results maintain better structure information and data relativity (e.g., high Pearson correlation and Spearman correlation). This can be predictable as the low dose image has information that can contribute to the CBV. Nevertheless, Pre-contrast image alone as input training data can still provide a promising performance of CBV estimation. For all testing cases, DeepCBV derived directly from Pre images show significantly improvement over the 20% low-dosage CBV on all quantitative metrics, showing the potential of developing a GBCA-free CBV estimation algorithm using deep learning. Statistical analyses were using paired t-test; Values denote mean±S.E.M. *P<0.05, P<0.01, *P<0.001. An enhanced CBV map can be obtained with just the Pre image as input.

Exemplary Performance of DeepCBV in GBM CBV Enhancement in Mice

The exemplary ResAttU-Net was applied to the GBM mouse model. FIG. 6A shows the predicted result of one slice of the same tumor subject according to an exemplary embodiment of the present disclosure. Comparing with low dosage CBV, both Pre+Low and Pre image has generated CBV maps, which have similar contrast as the ground truth. The DeepCBV prediction with input of both the Pre+Low and Pre only image shows significant contrast enhancement and tumor region prediction compared to 20% low-dosage result. FIG. 6B shows that DeepCBV significantly outperforms the 20% low-dosage CBV estimation. In particular, FIG. 6B shows quantitative comparisons (e.g., MSE, SSIM, P.R², S.R², and PSNR) between the two input's DeepCBV results (e.g., ResAttU-Net 605 and ResAttU-Net 610) and the 20% low-dosage result (e.g., 20% Low Dose 615). Statistical analyses were using paired t-test; Values denote mean S.E.M. *P<0.05, P<0.01, *P<0.001.

Figure 7A:
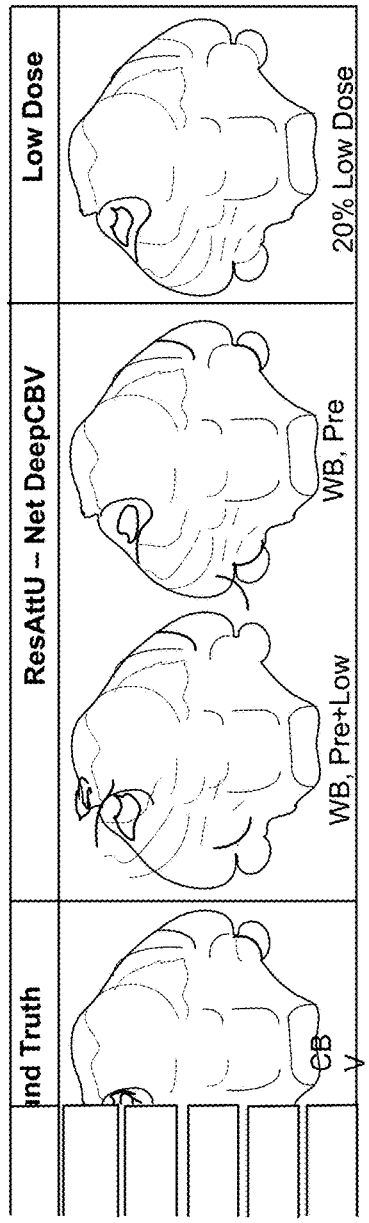
FIG. 7A is a set of exemplary images illustrating three-dimensional tumor regions of Ground truth and DeepCBV predictions and 20% low-dosage CBV map under a same threshold according to an exemplary embodiment of the present disclosure.
Figure 7B:
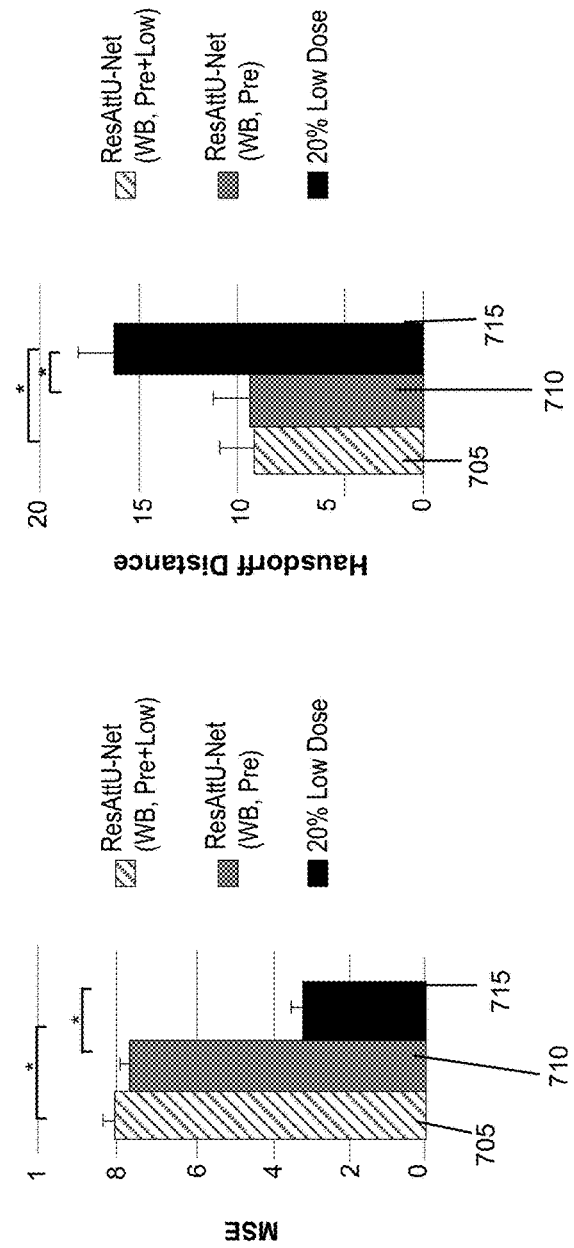
FIG. 7B is a set of exemplary graphs illustrating quantitative comparisons for Dice coefficient and Hausdorff distance between the two input's DeepCBV results and the 20% low-dosage result according to an exemplary embodiment of the present disclosure.

FIG. 7A shows the 3D rendering results of CBV ground truth vs DeepCBV in the FCM segmented tumor region. Compared with low dosage CBV, both the two DeepCBV models derived the tumor region more precisely with a similar contrast level of the ground truth. FIG. 7B shows a set of exemplary graphs illustrating quantitative comparisons for Dice coefficient and Hausdorff distance between the two input's DeepCBV results and the 20% low-dosage result according to an exemplary embodiment of the present disclosure. The exemplary models with the input of both Pre+Low (e.g., ResAttU-Net 705) images and the Pre-only (e.g., ResAttU-Net 710) images outperformed the 20% low-dosage (e.g., 20% Low Dose 715) on both Dice coefficient and Hausdorff distance significantly. Statistical analyses were using paired t-test; Values denote mean S.E.M. *P<0.05, P<0.01, *P<0.001. Both the Pre+Low and the Pre image can predict the tumor region with enhanced contrast and similar space feature by ResAttU-Net.

Exemplary Performance of DeepCBV in Human Studies

Figure 8:
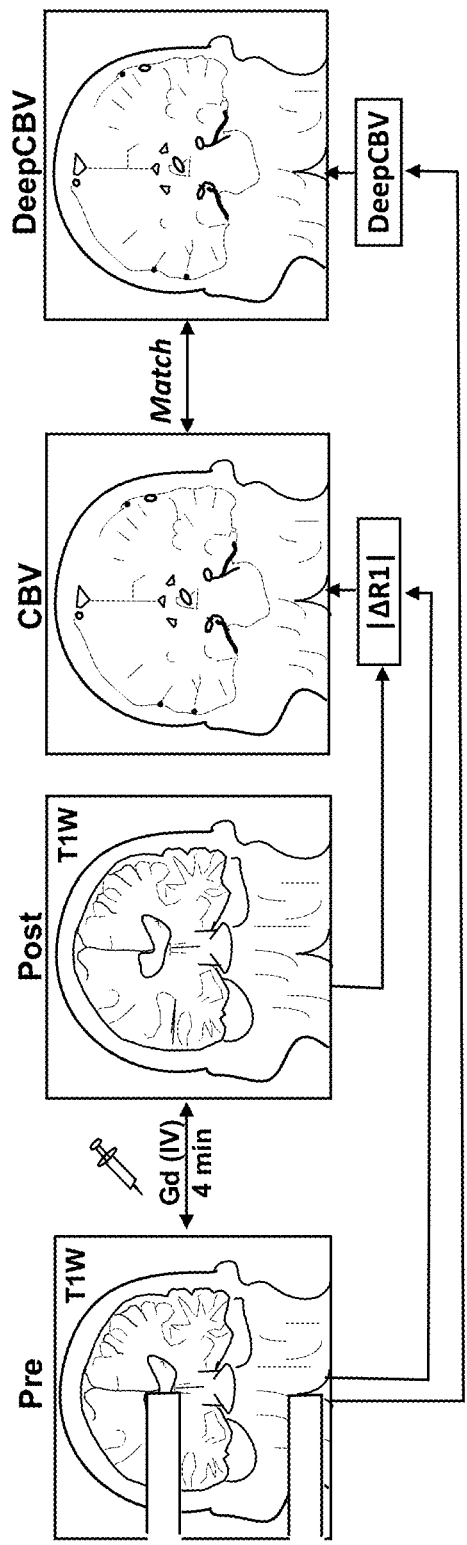
FIG. 8 is a set of exemplary images illustrating human CBV fMRI data acquisition and processing pipeline according to an exemplary embodiment of the present disclosure.

FIG. 8 illustrates a set of exemplary images illustrating human CBV fMRI data acquisition and processing pipeline according to an exemplary embodiment of the present disclosure. T1W structural MRI scans with Gd contrast enhancement are acquired and CBV ground truths were calculated as the normalized gadolinium uptake modeled by the change of the longitudinal T1 relaxation rate ("ΔR1"). The exemplary DeepCBV deep learning model can be used to predict the CBV mappings solely from the Gd-free pre-contrast T1W structural scans. DeepCBV was estimated directly from Gd-free T1W pre-contrast scan using the exemplary ResAttU-Net deep learning procedure as shown in FIG. 2, with T1W pre-contrast scan as the single-channel input.

The exemplary system, method, and computer-accessible medium, according to an exemplary embodiment of the present disclosure, can also be used to generate high-quality human CBV maps directly from the Gd-free T1W scans. (See e.g., FIGS. 9A and 9B). For example, FIG. 9A shows a set of exemplary images of human brain MRI scans for T1W Gd-free pre-contrast scan 905, T1W post-contrast scan with steady-state Gd uptake 910, CBV ground truth generated as the normalized ΔR1 map 915, and DeepCBV estimated directly from the pre-contrast T1W scan using the exemplary deep learning procedure 920.

Figures 9A, 9B, 9C:
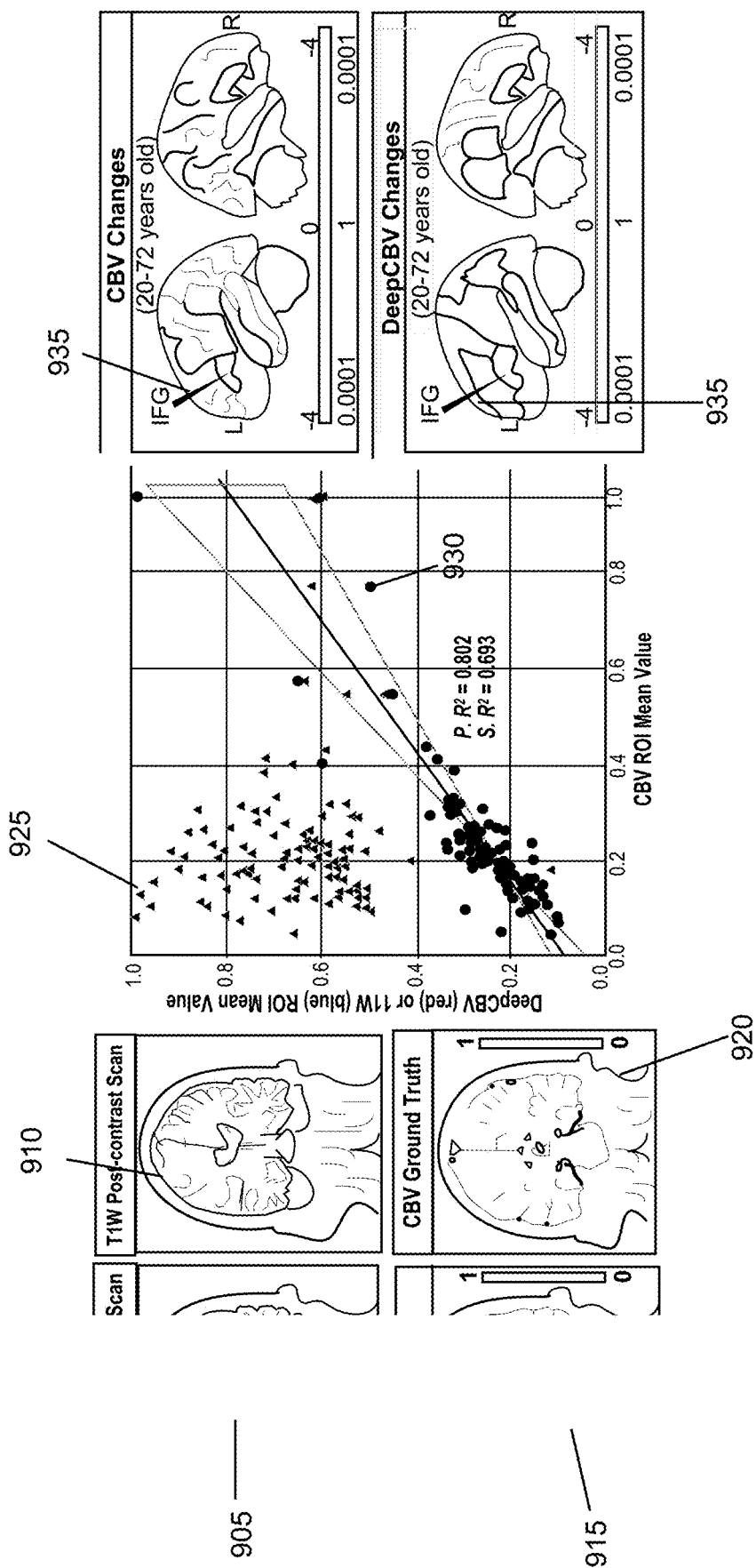
FIG. 9A is a set of exemplary images of human brain MRI scans according to an exemplary embodiment of the present disclosure.
FIG. 9B is a graph illustrating a region-of-interest correlation analysis according to an exemplary embodiment of the present disclosure.
FIG. 9C is a set of exemplary images of three-dimensional renderings of rates of CBV change over time according to an exemplary embodiment of the present disclosure.

FIG. 9B illustrates a graph illustrating a region-of-interest correlation analysis (e.g., for T1W 925 and DeepCBV 930), with significant Pearson correlation coefficient (("P.R")= 0.802) and Spearman correlation coefficient (("S.R")= 0.693), according to an exemplary embodiment of the present disclosure. In addition, the exemplary DeepCBV can be used to map the spatial pattern of normal cognitive aging associated changes of CBV in the human brain. Spatial pattern of changes in CBV in normal aging can be observed based on CBV fMRI over 100 carefully-screened cognitively normal individuals spanning 20-72 years of age. In particular, left-hemisphere inferior frontal gyrus ("IFG") can be mostly affected, and left-hemisphere IFG regional CBV can have the most reliable age-related decrease. (See e.g., FIG. 9A, frame 905). The IFG finding was reproduced using DeepCBV on the same cohort with 178 scans been processed.

Similar spatial patterns of changes in DeepCBV and CBV have been observed for normal aging. (See e.g., FIG. 9C). In particular, FIG. 9C shows a set of exemplary images of three-dimensional renderings of rates of CBV change over time (e.g., with over 100 cognitively normal individuals spanning 20-72 years) demonstrating that there are consistent trends between age-associated changes in DeepCBV and CBV in normal aging. ROI correlation analysis between age-associated rates of change in CBV (ROIs with age regressor related p<0.05) and the corresponding DeepCBV have strong linear and monotonic relationships (e.g., with a significant Pearson correlation coefficient $R^2$=0.599 and Spearman correlation coefficient $R^2$=0.923). Left-hemisphere IFG regional CBV has the most reliable age-related decrease in normal aging (e.g., indicated by arrows 935 in FIG. 9C).

Exemplary Discussion

Gadolinium based MRI imaging can provide a wide variety of knowledge to advance patient care. MRI is often used to investigate a new finding, or repeatedly used to track the evolution of the pathological process. With findings of Gd retention, it can be beneficial to utilize MRI imaging in order to decrease the Gd exposure.

Gd-enhanced steady-state CBV MRI imaging (see, e.g., Reference 22) can be used to produce in vivo nonradioactive high-resolution functional mapping of basal brain metabolism in both mice and humans. (See, e.g., References 10 and 11). CBV can be related to regional metabolism in healthy and diseased brains (see, e.g., References 23 and 24) and can be useful to study cognitive aging (see, e.g., Reference 25), Alzheimer disease ("AD") (see, e.g., Reference 26) and tumor. (See, e.g., Reference 27). For AD, the disease can begin by impairing neuronal function in a specific sub-region of the hippocampal formation. (See, e.g., Reference 11). Of functional imaging procedures sensitive to metabolism, Gd-enhanced CBV MRI can have the highest spatial resolution that can most readily visualize individual hippocampal sub-regions in both mice and humans. (See, e.g., References 8 and 28). Thus, Gd-enhanced CBV can be well-suited to detect AD-related metabolism dysfunctions. (See, e.g., References 11 and 28). For brain tumor studies, for example, GBM is one of the most common and aggressive types of malignant brain tumors. As the most vascularized tumor in humans (see, e.g., Reference 29), its growth is closely associated with the formation of new vessels and signs of blood-brain-barrier ("BBB") leakage. (See, e.g., Reference 30). Studies demonstrated that increased CBV of GBM was driven by hyperactive angiogenesis (see, e.g., Reference 31) and aggressive BBB leakage. (See, e.g., Reference 32). Gd-enhanced CBV is well-suited to detect GBM-related regional hyperactive angiogenesis and BBB leakage and has become a potential imaging biomarker for GBM detection and grading. (See, e.g., References 33-36).

Comparing the quantitative evaluation results, the exemplary Deep Learning methods have significant improvement over the low-dosage (e.g., and the pre-contrast scans). Low MSE, high SSIM and high correlations between the DeepCBV and the CBV ground truth indicate that the exemplary Deep Learning method does not lead to significant quality degradation. High performance of GBM segmentation reflected by high Dice coefficient and low Hausdorff distance between the DeepCBV- and CBV ground truth-derived tumor masks indicate that the estimated DeepCBV can produce similar GBM enhancement as the full-dose scans. Reducing, or even removing, the Gd contrast while retaining diagnostic information could can a large impact on patient well-being and imaging costs.

The exemplary system, method, and computer-accessible medium, according to an exemplary embodiment of the present disclosure, can also train a 3D network, taking upsampled isotropic 3D volumes as its input. Additionally, the exemplary system, method, and computer-accessible medium can be sensitive to scan orientation and anatomy variance; thus, scans can be acquired with the same geometry and orientation. Further, the spatial variance can be further reduced by image co-registration.

For the exemplary GBM mouse model, all MRI scans were acquired 10 days after the cell injection at the right-side stratum. The lack of longitudinal dataset and GBM locations can lead to biased DeepCBV predictions when the GBMs can be in different stages, or the GBM cells were injected at different brain regions. To improve the robustness and accuracy of the DeepCBV for the GBM enhancement, dataset can be enriched by adding mice scans with GBMs at various stages and injection sites.

MSE can be chosen as the cost function to train the exemplary Deep Learning networks. The training strategy can be further improved by adding other loss functions. (See, e.g., Reference 37). In addition, Generative Adversarial Network ("GAN") can be used, which has been shown to have outstanding performance in recovering high-frequency details of image reconstruction. (See, e.g., Reference 38).

The exemplary system, method, and computer-accessible medium, according to an exemplary embodiment of the present disclosure, can apply deep learning to generate contrast-enhanced CBV maps with reduced Gd dosage. The exemplary deep learning procedure can reduce Gd dosage by at least 5-fold while preserving high-quality CBV contrast. In addition, CBV maps of the whole brain can be directly generated from Gd-free T2W anatomical scans, which can provide a significant benefit to human MRI. The exemplary system, method, and computer-accessible medium according to an exemplary embodiment of the present disclosure was tested on a Gd-enhanced human CBV dataset. High-quality CBV maps were generated directly from the Gd-free T1W scans. Thus, the exemplary system, method, and computer-accessible medium, according to an exemplary embodiment of the present disclosure, can be used to generate high quality Gd contrast in brain MRI from widely available exogenous-contrast-free structural MRI while preventing Gd retention.

Figure 10:
FIG. 10 is an exemplary flow diagram of an exemplary method for generating a gadolinium enhanced map of a portion of a patient according to an exemplary embodiment of the present disclosure.

FIG. 10 illustrates an exemplary flow diagram of an exemplary method 1000 for generating a gadolinium enhanced map of a portion of a patient. For example, at procedure 1005, MRI information of the portion can be received. At procedure 1010, the Gd enhanced map can be generated based on the MRI information using a machine learning procedure. At procedure 1015, a Gd contrast can be generated in the Gd enhanced map using a T2-weighted MRI image of the portion.

Exemplary Magnetic Resonance Imaging Using Deepcontrast

Deep learning can produce Gd contrast in brain MRI directly from single non-contrast structural MRI. This was analyzed in mice. The residual attention U-Net architecture was used in the exemplary deep learning model to estimate Gd contrast from non-contrast T2W MRI for CBV mapping. The exemplary procedure was evaluated for both WT mice and mice with GBM at 9.4T.

Exemplary Material and Methods

Figures 15A, 15B:
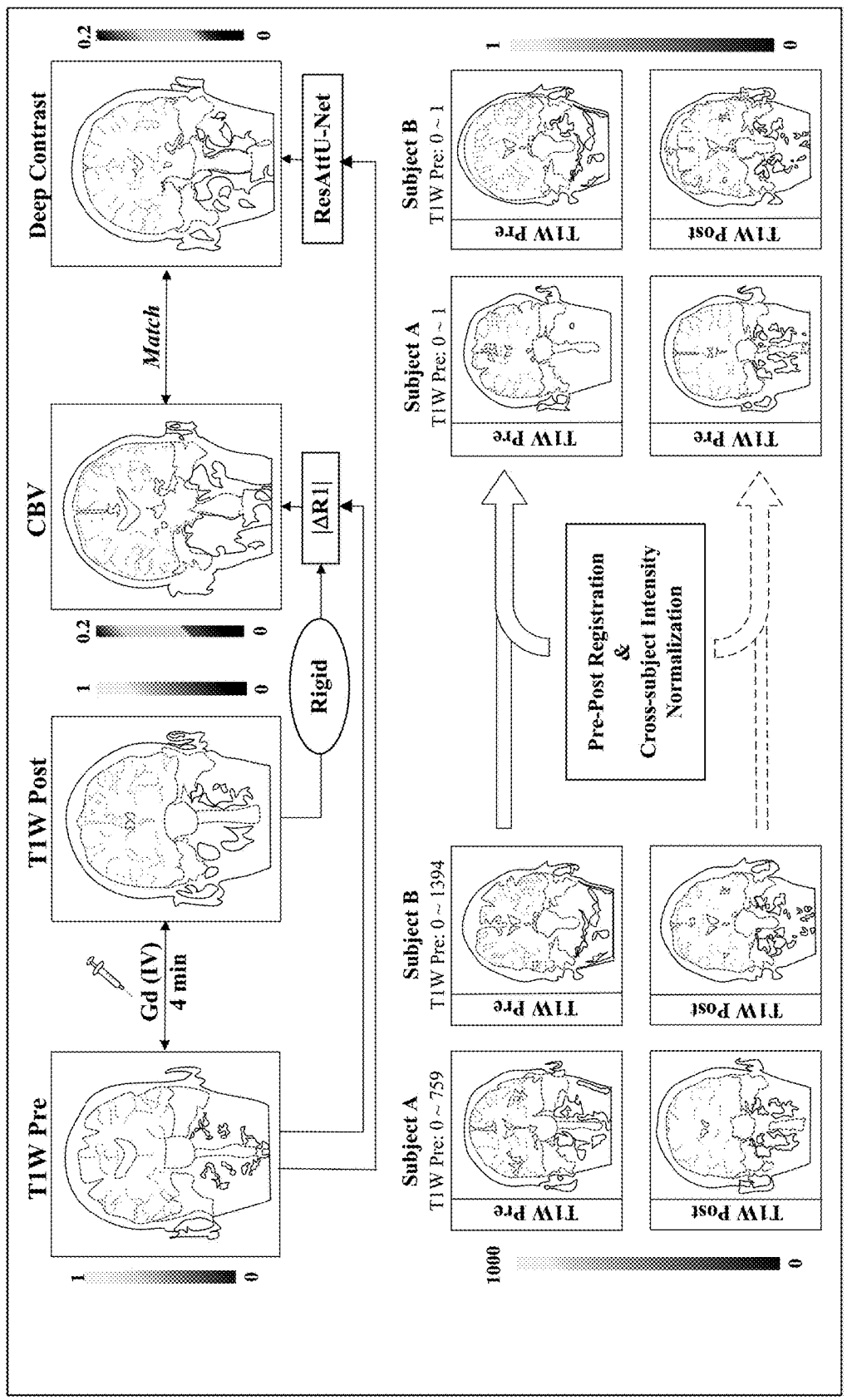
FIG. 15A is a set of T1W MRI scans before and after Gd enhancement according to an exemplary embodiment of the present disclosure.
FIG. 15B is a set of exemplary images illustrating two exemplary pre-processing procedures according to an exemplary embodiment of the present disclosure.
Figure 16:
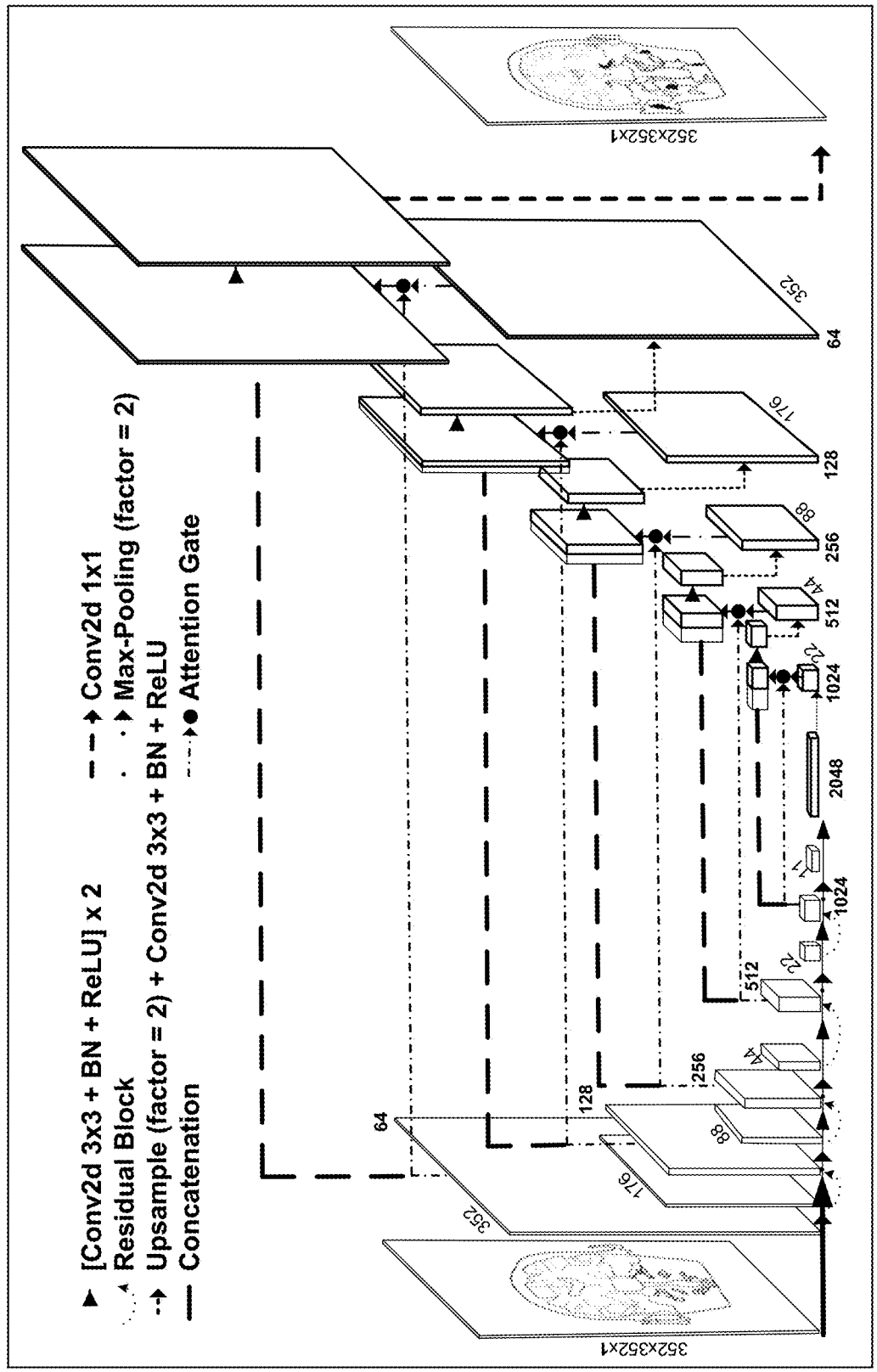
FIG. 16 is an exemplary diagram illustrating the exemplary DeepContrast network architecture according to an exemplary embodiment of the present disclosure.
Figures 18A, 18B:
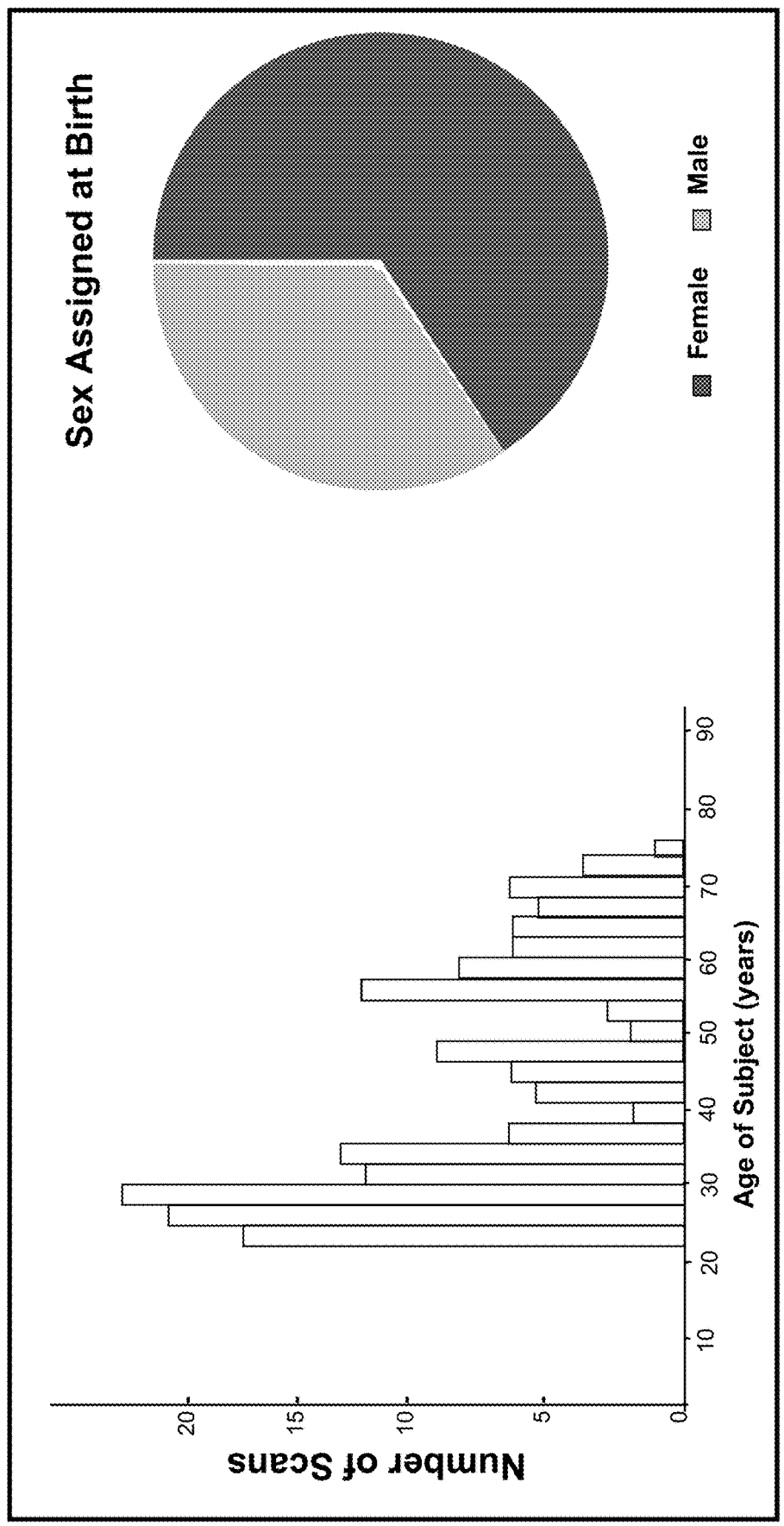
FIGS. 18A and 18B are exemplary charts illustrating the population distribution used for the exemplary dataset according to an exemplary embodiment of the present disclosure.

T1W human brain MRI scans are acquired using an exemplary protocol (see, e.g., References 29-31), before (e.g., Pre) and 4 minutes after (e.g., Post) intravenous bolus injection of Gadodiamide. Within each Pre-Post pair, the two scans share the same intensity scales. Scans can be brain-extracted and spatially co-registered as described previously. (See, e.g., Reference 29-31). Intensity normalization can be performed by mapping the Pre scans to the range of [0, 1] and propagating the scaling to the post scans. CBV, a metabolic mapping utilizing GBCA contrast, can be calculated as the difference between Post and Pre for each pair. FIGS. 15A and 15B demonstrate the pipeline. A deep learning model with a Residual Attention U-Net architecture, as shown in FIG. 16, can be used to predict the GBCA contrast directly from the Pre scans. On the Pre and CBV scans of 600 subjects, a train-validation split can be performed at a ratio of 6:1, while 180 subjects can be left for the test set. Evaluation of the DeepContrast model comes in two aspects. In the first exemplary aspect, it can be used to generate GBCA contrast predictions on the 180-scan test set and the resulting mappings can be quantitatively compared to the ground truth CBV maps. In the second exemplary aspect, the exemplary DeepContrast was evacuated to map the age-related CBV changes over the whole cortical mantle. To achieve this, the DeepContrast model can be applied on a previously unseen dataset that consists of 178 T1 W Pre scans where the subject population is shown in FIGS. 18A and 18B. The T1 W Pre, CBV, and DeepContrast predictions can be individually used to each generate an age-related regression t-map over 72 cortical ROIs defined by FreeSurferII parcellation. The t-map can be constructed by running a single-variable linear regression y-x, where the dependent variable y can be the mean intensity of the ROI in each scan divided by the mean intensity of the top 10% brightest values in the white matter 9 of that scan, while the independent variable x can be the age of the subject. The regression t-value for each ROI can be filled back to its spatial location to form the t-map. Significant negative values in the t-map indicate the brain regions with decline in metabolic activities as humans get older.

Exemplary Animal Subject

Mice used in the exemplary study were divided into two groups: WT mice and mice with GBM. The WT group contained 49 healthy adult C576J/BL male mice scanned at 12-14 months old. The GBM group contained 10 adult C576J/BL male mice that were injected with PDGFB (+/+) PTEN (−/−) p53 (−/−) GBM cells. (See, e.g., Reference 52). 50,000 cells in 1 μL were stereotactically injected into the brain. MRI scans of GBM mice were obtained 10 days after injection.

Exemplary MRI Acquisition and Preprocessing

For each mouse, T2W MRI scans were acquired using the 2D T2-weighted Turbo RARE sequence at 9.4T (e.g., TR/TE=3500/45, RARE factor=8, 76 μm in-plane resolution, 450 μm slice thickness; Bruker Biospec 94/30 USR equipped with CryoProbe).

Figure 11A:
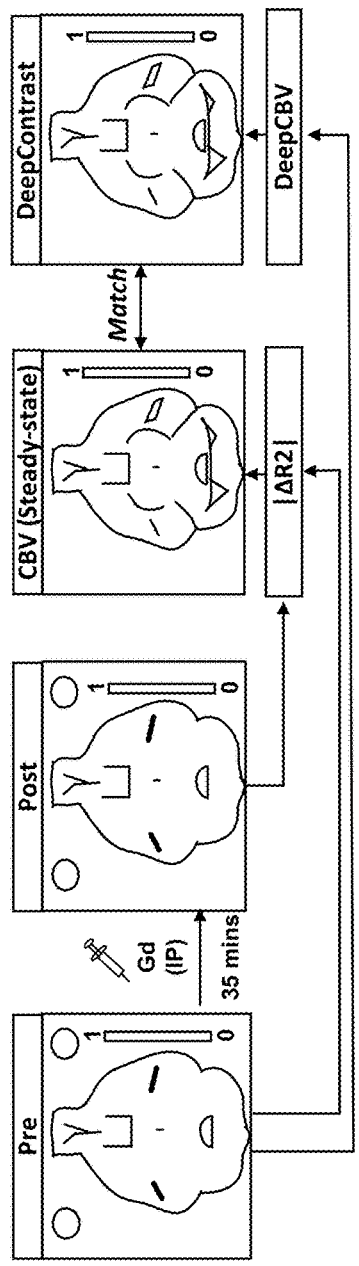
FIG. 11A is a set of exemplary steady-state CBV map derived using the exemplary T2W MRI Pre scans according to an exemplary embodiment of the present disclosure.
Figure 11B:
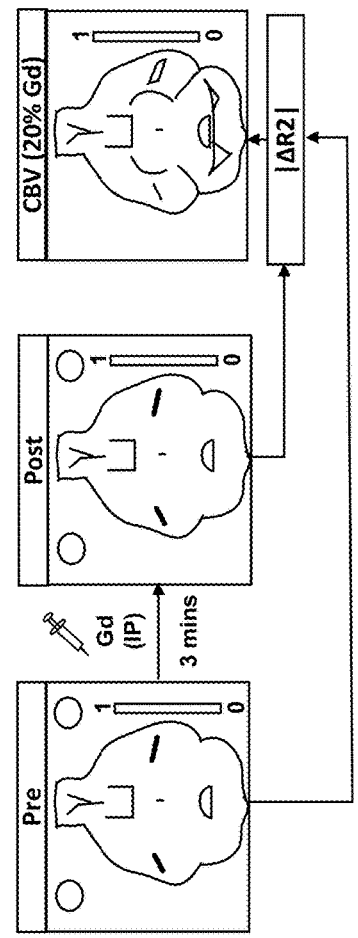
FIG. 11B is a set of exemplary low dose CBV maps according to an exemplary embodiment of the present disclosure.

To derive the steady-state CBV maps, whole brain T2W MRI scans before (e.g., Pre) and 35 minutes after (e.g., Post) IP injection of Gadodiamide at 10 mmol/kg can be acquired with identical scan parameters. (See e.g., FIG. 11A). (See, e.g., Reference 53). As a direct approach to reduce Gd dose, the 20% low-dose CBV maps were derived, as illustrated in FIG. 11B. For scans of tumor subjects, tumor masks can be generated in addition to the brain masks using the Fuzzy-C-Means segmentation. (See, e.g., Reference 54).

Exemplary Deep Learning Model

Exemplary Model Architecture

Figure 12:
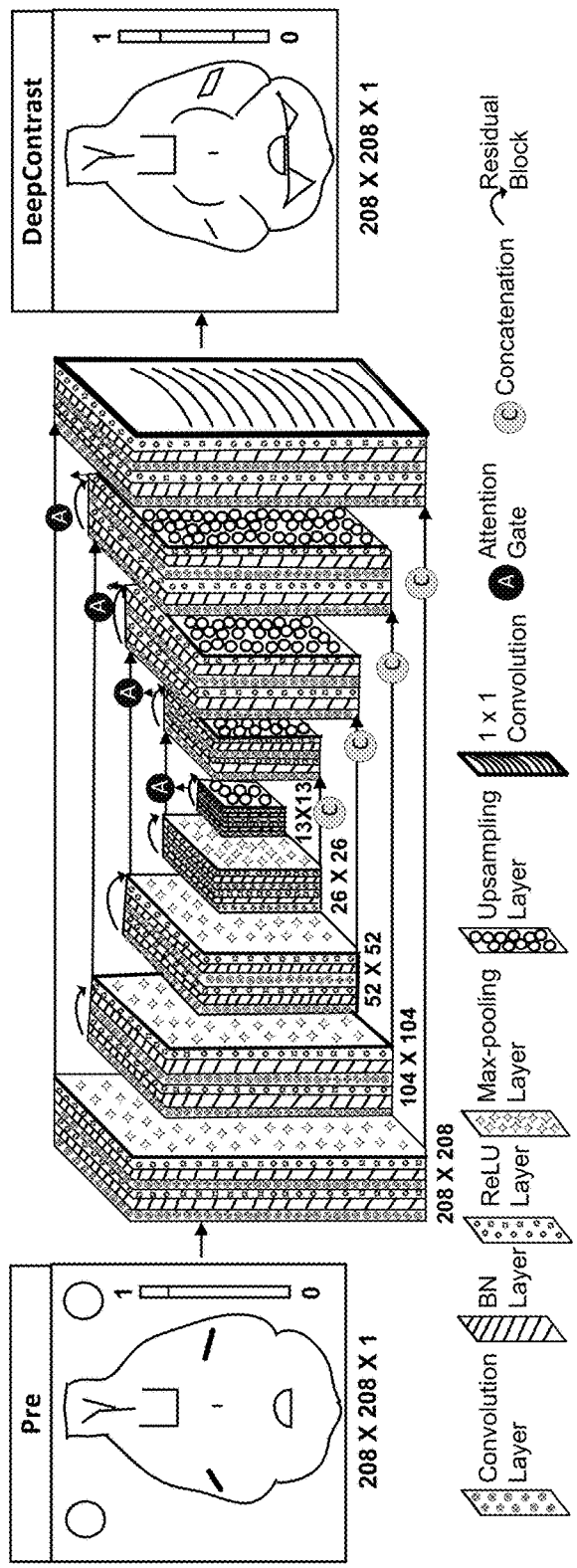
FIG. 12 is an exemplary diagram of the exemplary architecture of the exemplary REDAttU network according to an exemplary embodiment of the present disclosure.

The deep learning architecture utilized in the exemplary study can be the out-stand five-layer ResAttU-Net as illustrated in FIG. 12. This consists of a contraction path that encodes high-resolution data into low-resolution representations and an expansion path that decodes such encoded representations back to high-resolution images. The exemplary deep learning model was implemented using PyTorch framework with CUDA 10.0, 2 NVIDIA RTX 2080-TI GPUs and CentOS 6.

Both the encoder and decoder parts can be based on the U-Net structure (see, e.g., Reference 55) where each stage consists of two series of 3×3 2D convolutions, batch normalization, and ReLU. In the encoder part, each stage can be followed by 2×2 max-pooling for down sampling, while for the decoder part, four 2×2 upsampling layers convert low-resolution representation back to high resolution. Additionally, every stage of the decoder has concatenation from the encoder at the same level to give the model more accurate local information for assembling a precise prediction.

To further refine the exemplary network, as illustrated in FIG. 12, the residual blocks and the attention gates can be incorporated into the U-Net architecture. The residual block can optimize the signal and gradient propagation within a network while preventing overfitting from being a problem. (See, e.g., Reference 56). While the attention gate can significantly suppress feature responses in irrelevant background regions without needing to crop an ROI. (See, e.g., Reference 57).

Exemplary Training the Model

ADAM was used as the optimizer with a learning rate of 10-3 and maximum 200 epochs with early stop. A batch size of 3 and randomize non-overlapping input images were used for training. Scans of 6 standalone mice were used for validation.

Exemplary Applying the Model

The ResAttU-Net was applied to derive the steady-state CBV maps in WT mice directly from their non-contrast pre-scans. In addition to demonstrating the ability to produce CBV in the normal brain tissue, its utility can further be used in the enhancement of pathology visibility and delineation of brain lesions as the exemplary second objective. 49 WT mice can be used in the study, with a randomized 37-6-6 train-validation-test split. 6 GBM mice scans were randomly to the training set and the model was retrained. The performance of DeepContrast on tumor enhancement was tested on 4 GBM mice scans.

Exemplary Evaluation and Statistical Analysis

To evaluate the performance of DeepContrast, a PSNR was used to assess the estimation error at the voxel level. Given the limitation of PSNR on capturing the perceptually relevant differences, the SSIM was determined to evaluate the accuracy of estimating a processed image on the structural level. (See, e.g., Reference 58). In addition, Pearson and Spearman correlation analysis were constructed to assess the linear and monotonic associations between the CBV ground truth and DeepContrast respectively. For the GBM study, besides the voxel level comparison, the Dice similarity coefficient and Hausdorff distance were used to compare the performance of DeepContrast and the CBV ground truth in tumor segmentation.

Exemplary Results

Exemplary Performance of DeepContrast in Normal Brain CBV Mapping

Figure 13A:
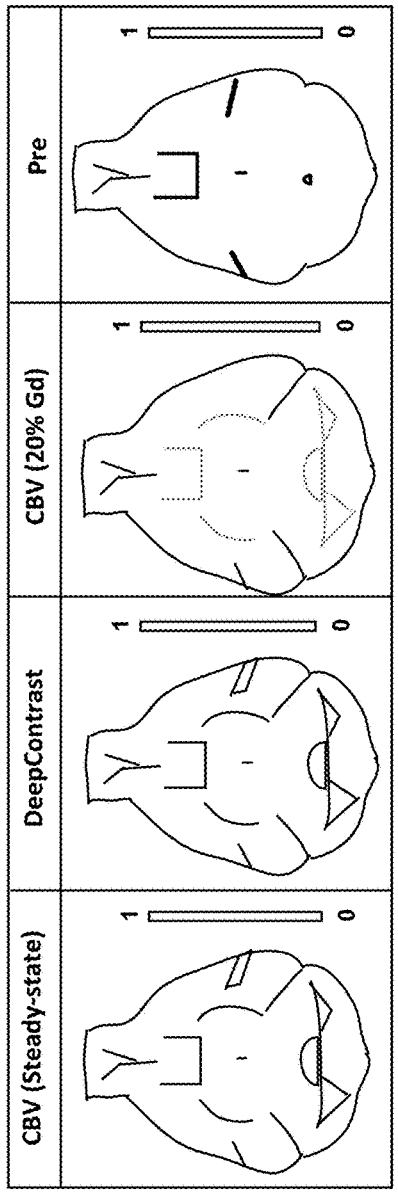
FIG. 13A is a set of exemplary steady-state ground truth maps according to an exemplary embodiment of the present disclosure.
Figure 13B:
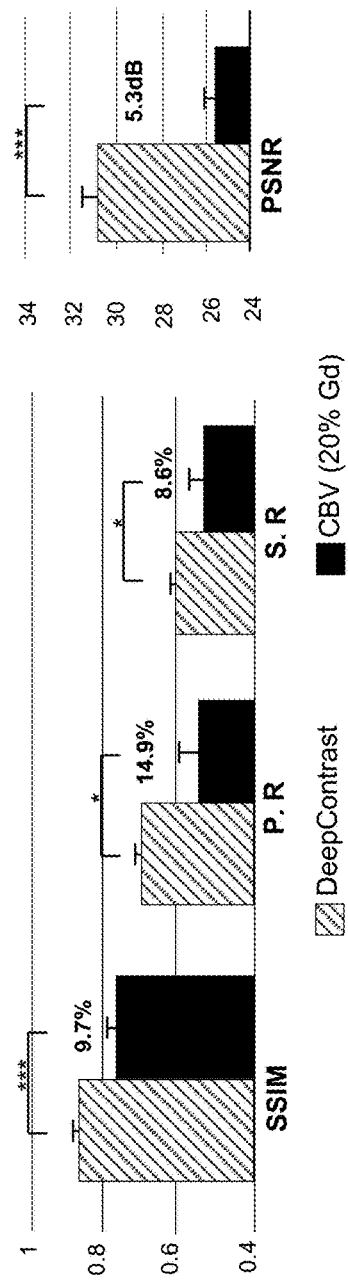
FIG. 13B is a set of exemplary charts illustrating comparisons between the exemplary DeepContrast results and a 20% Gd CBV according to an exemplary embodiment of the present disclosure.

Example of the DeepContrast prediction and the quantitative metrics of the standalone 6 testing subjects are shown in FIGS. 13A and 13B. DeepContrast captured the high contrast and fine details of small vessels with high similarity to the steady-state CBV ground truth in the normal brain tissue. FIG. 13A shows the CBV ground truth, predicted result, 20% low Gd dose CBV and non-contrast Pre-image of the same mouse. The Pre-image alone can provide promising prediction results that show strong enhancement compared to the 20% low-dose CBV that can be consistent with the steady-state CBV maps. FIG. 13B shows the quantitative comparison of the DeepContrast and 20% Gd CBV map. DeepContrast clearly improved the CBV contrast derived from 20% Gd enhancement with a gain of 9.7% SSIM (e.g., p<0.001), an increase of 5.3 dB in PSNR (e.g., p<0.001), an improvement of 14.9% increase of P.R (e.g., Pearson Correlation, p<0.05) and an 8.6% increase in S.R (e.g., Spearman Correlation, p<0.05).

Figures 17A, 17B:
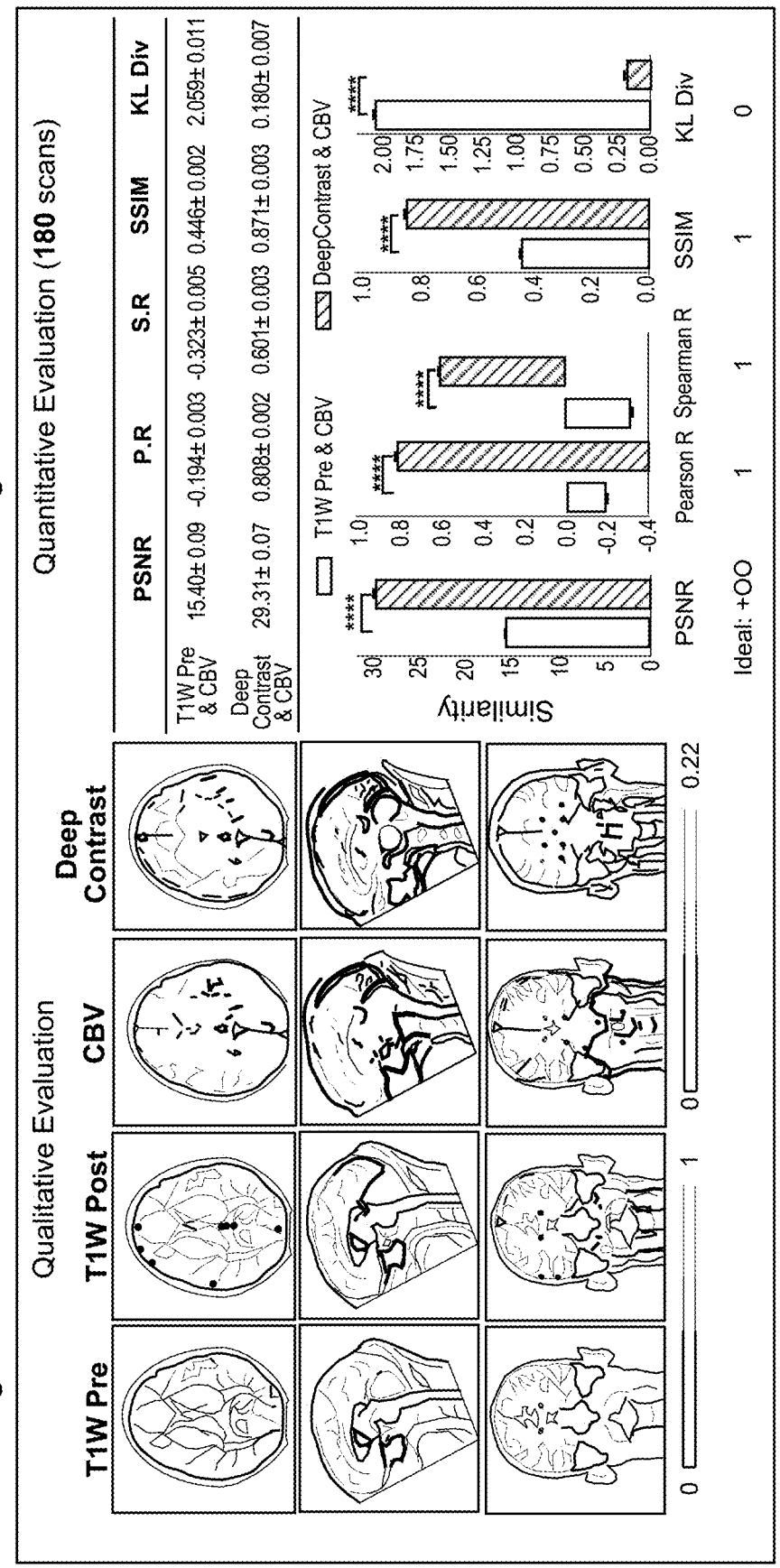
FIG. 17A is a set of exemplary images illustrating a similarity analysis between CBV and the exemplary Deep- Contrast using visual inspections according to an exemplary embodiment of the present disclosure.
FIG. 17B is a set of exemplary charts illustrating a similarity analysis performed on test scans.
Figures 19A, 19B, 19C, 19D:
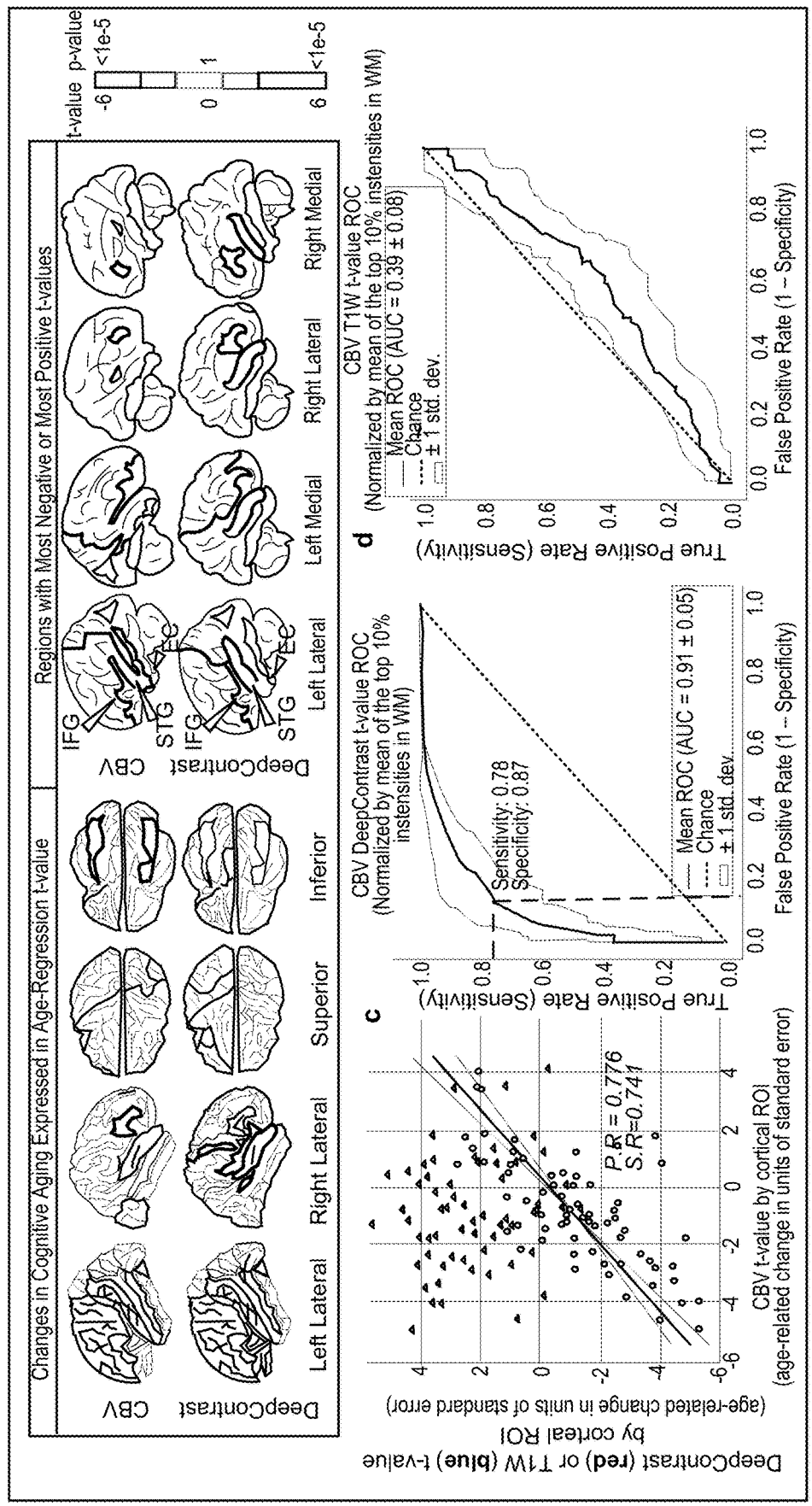
FIG. 19A is a set of exemplary images of 3D renderings of rates of metabolic change over time according to an exemplary embodiment of the present disclosure.
FIG. 19B is an exemplary chart illustrating a correlation analysis among t maps according to an exemplary embodiment of the present disclosure.
FIGS. 19C and 19D are exemplary charts illustrating receiver operating characteristics of the 1000-class classification using normalized CBV t-values as ground truths and normalized t-values from either the exemplary DeepContrast or T1W as the predictor according to an exemplary embodiment of the present disclosure.

In the first exemplary aspect, the quantitative voxel-level analysis (see e.g., FIGS. 17A and 17B) yields a PSNR=29.31, Pearson R=0.808, Spearman R=0.601, SSIM=0.871, and KL divergence=0.180. This assessment demonstrates that even though the structural T1 W Pre scans may not be like the CBV maps, DeepContrast can extract the metabolic information from them and resemble CBV. In the second aspect, DeepContrast can be applied to examine imaging correlates of cognitive aging. FIG. 19A shows that the spatial distribution of age-related metabolism changes seen in DeepContrast predictions can be consistent to those in the CBV ground truth. IFG and superior temporal gyrus ("STG") show the most reliable aging-induced hypometabolism (e.g., indicated by the red arrows), while entorhinal cortex experiences the least metabolic degradation (e.g., indicated by the green arrow). These regions identified agree with existing findings (see, e.g., References 77-79). FIG. 19B breaks down the t-maps into a scatter plot with each point representing a cortical ROI, and it shows significant linear and monotonic correlation between DeepContrast prediction and CBV despite no correlation between T1 W Pre and CBV. FIG. 19C shows an exemplary illustration of an exemplary receiver operator characteristic ("ROC") when treating the t-value concordance as a series of binary classification problems with 1000 different binarizing thresholds. The t-values from the 72 cortical ROIs can be linearly mapped to [0, 1] respectively for CBV, T1 Wand DeepContrast predictions, and can be used to indicate the regional t-value concordances. It can be inferred that the t-values in DeepContrast predictions have significant predictive power on its CBV counterpart, while those in T1W scans do not.

Exemplary Performance of DeepContrast in GBM CBV Enhancement

To experiment and evaluate the utility of the exemplary DeepContrast method in the enhancement of pathology visibility and delineation of brain lesions, the same ResAttU-Net architecture was trained with additional MRI scans of the GBM mouse model.

FIGS. 14A and 14B show exemplary illustrations indicating that the DeepContrast predicted results perform significantly better than the 20% Gd CBV in both visual assessment and the quantitative evaluation. FIG. 14A shows the predicted result of one slice of the same tumor subject. Compared with 20% Gd CBV, DeepContrast generated from the T2W Pre scan shows similar contrast level to the ground truth. The consistency can be observed in the fine structure and significant contrast enhancement in both normal tissue and the tumor region. FIG. 14B is the detailed quantitative metrics evaluation of 4 randomly selected testing tumor subjects. Compared with the 20% Gd CBV, DeepContrast has a 4.8% increase in SSIM (e.g., P<0.05), a 2.0 dB increase in PSNR (e.g., P<0.05), and a 19.6% increase in P.R (e.g., Pearson Correlation, P<0.05) and a 2.6% increase in S.R (e.g., Spearman Correlation, P<0.05). FIGS. 14A-14D show exemplary illustrations that the DeepContrast predicted results perform significantly better than the 20% Gd CBV in both visual assessment and the quantitative evaluation.

FIGS. 14C and 14D show further illustrations that further confirm that the DeepContrast models with the input of Pre only image significantly outperformed the 20% Gd for the tumor region. FIG. 14C shows the 3D rendering results of CBV ground truth vs DeepContrast in the FCM segmented tumor region of a single tumor subject. Compared to low dose CBV, both the two DeepContrast models derived the tumor region more precisely with a similar contrast level to the ground truth.

FIG. 14D shows illustrations of exemplary quantitative comparison between the DeepContrast predictions and the 20% Gd CBV of the tumor region. The DeepContrast performed significantly better than the 20% Gd of the tumor region, with 47.0% Dice coefficient increases (e.g., P<0.05) and 5.5 pixels Hausdorff distance reductions (e.g., P<0.05).

Exemplary Discussion and Conclusions

Findings of Gd retention may necessitate efforts to develop novel approaches to MRI that can decrease or even eliminate Gd exposure. In the past, there have been several attempts to develop non-contrast MRI sequences such as ASL, TOF, and VASO. (See, e.g., Reference 59). While such sequences have been successful and applied clinically, Gd based imaging still offers an unparalleled level of information in comparison. For example, Gd can be widely used for steady-state CBV fMRI imaging to map basal brain metabolism in both mice and humans. (See, e.g., References 45 and 47). CBV has been proven to be tightly coupled to regional metabolism in healthy and diseased brains (see, e.g., References 60 and 61) and can be useful in studying cognitive aging (see, e.g., Reference 60), AD (see, e.g., Reference 61) and tumors. (See, e.g., Reference 62). Gd-enhanced CBV can also be well suited to detect GBM-related regional hyperactive angiogenesis and BBB leakage, which has become a potential imaging biomarker for GBM detection and grading. (See, e.g., References 63-66).

Exemplary results from the exemplary study demonstrate that the GBCA contrast mappings predicted by the exemplary DeepContrast model not only qualitatively and quantitatively resemble the ground truth CBV, but also truly contain equivalent information that can be used to generate insights that concur with existing findings. The exemplary the exemplary model can generate high-quality and clinically relevant contrast mappings in the human brain from nothing more than the T1 W structural MRI scans, the single most prevalent modality in MRI.

Removing the Gd contrast entirely while retaining diagnostic information could have a large impact on both patient well-being and reduction of imaging time and costs. Recently, 3D Bayesian U-Net was applied to a dataset from patients with brain tumors and healthy subjects to predict contrast enhancement from a comprehensive multiparametric MRI protocol including T1w, T2w, T2w fluid-attenuated inversion recovery, diffusion-weighted imaging, and susceptibility-weighted imaging, all acquired without any Gd injections. (See, e.g., Reference 51). This exemplary method was limited in its inability to predict presence of small vessels and an inevitably long scan time likely to exhaust patients due to utilization of 10 multiparametric MRI scans as its input. In view of these limitations, DeepContrast was developed to, e.g., rely primarily, or solely, on information extracted from the most commonly acquired structural MRI scans. Compared to the 3D Bayesian U-Net, the exemplary approach provides several improvements to predicting contrast enhancement. First, it was shown that Gd contrast in brain MRI can be directly derived from a single non-contrast T2W MRI in both normal brain tissue and brain lesion. High PSN, high SSIM and high correlations between the DeepContrast and the Gd-enhanced ground truth suggest that the exemplary proposed method does not cause significant quality degradation. High accuracy of GBM segmentations suggest DeepContrast can detect GBM with performance like full-dose Gd-enhanced scans. Furthermore, the exemplary deep learning method can be based on a hybrid deep residual attention-aware network and can be the first network to use an attention residual mechanism to process brain MRI scans. The basic architecture of the proposed network can be a 2D U-Net that extracts contextual information combining low-level feature maps with high-level ones. Attention modules can be stacked such that the attention-aware features change adaptively in the deeper layers of the network. This can be performed based on residual learning. The exemplary procedure can produce CBV mapping of small vessels with high fidelity.

To improve the robustness and accuracy of the exemplary DeepContrast for GBM enhancement, the current training dataset can be enhanced by adding MRI scans of mice injected with GBM cells at various stages and different locations. Beyond diversifying the dataset, to deal with the intensity difference within and across subjects, recent advancements in intensity standardization/normalization can enhance the estimation of the DeepContrast enhancement when translating the exemplary model to human data. (See, e.g., Reference 67). MSE was chosen as the cost function in the exemplary current model. However, the training strategy can be further improved by adding other evaluation parameters to the loss function.

The exemplary procedure according to exemplary embodiments of the present disclosure can be used to generate Gd contrast in brain MRI directly from T2W MRI scans with complete omission of GBCAs. DeepContrast can be used to provide benefits to patient care and the healthcare system through reduction of Gd exposure, scan time, and cost.

An exemplary deep learning model according to exemplary embodiments of the present disclosure can be used to extract gadolinium-equivalent information from a single and commonly-acquired T1-weighted MRI scan, e.g., by training and optimizing the model using a unique gadolinium MRI dataset. Previous deep learning studies relied on gadolinium datasets generated for radiological purposes, where post-gadolinium scans are rescaled, easing a radiologist's ability to detect and characterize brain lesions. This rescaling, however, dramatically increases intrasubject variability across a dataset. With the exemplary specific interest in mapping functional brain lesions that localize to specific regions of the hippocampal formation, over the last couple of decades gadolinium has been used to generate quantitative, high-resolution, CBV maps. (See, e.g., References 84-86 and 94-978). These quantitative maps do not use any rescaling, and thus, while not the original intent, the reduced intrasubject variability in this large-scale data can be well-suited for deep learning purposes. In parallel to generating a large-scale and quantitative gadolinium dataset in people, a similar MRI dataset was generated in mice. Here again, the original intent was to validate patterns of hippocampal dysfunction observed across disease states, but because in mice studies subjects are siblings with identical genetic backgrounds, this mouse dataset can be notable for even less inter-subject variability than in people.

Thus, e.g., this distinct cross-species and quantitative gadolinium dataset was utilized. Beginning with mice, an exemplary deep learning model was designed, optimized, and trained, and then validated that it can substitute gadolinium. This exemplary procedure was then applied to people, by showing that trained deep learning models can visualize functional lesions that occur in the hippocampal formation in aging, schizophrenia, and Alzheimer's disease, and enhance structural lesion causes by tumors. The deep learning model can be referred to as 'DeepContrast'.

Exemplary Results
Exemplary DeepContrast in the Mouse Brain

The exemplary model was designed, optimized and trained the model on 49 WT mice brain scans (e.g., 37 for training and 6 for validation; see methods), in which quantitative T2-weighted gadolinium-uptake brain maps were previously generated, and then tested on a standalone group of 6 mice. Compared to gadolinium-uptake maps ("Gd-Uptake"), the DeepContrast model was able to derive gadolinium-predicted maps ("Gd-Predicted") that generated contrast-equivalent information across the brain, as indicated by visual inspection and by quantitative voxel-level analyses. (See e.g., FIGS. 21A-21F).

Next, the same network architecture was trained after adding brain MRI scans from 6 mice with GBM into the training set. Again, the DeepContrast model was able to derive gadolinium-predicted maps that generated contrast-equivalent information for enhancing tumor detection, as indicated by visual inspection, quantitative voxel-level analyses, and high-enhancement region ROC analyses. (See e.g., FIGS. 21A-21F).

Exemplary DeepContrast in the Human Brain

Figures 22A, 22B, 22C:
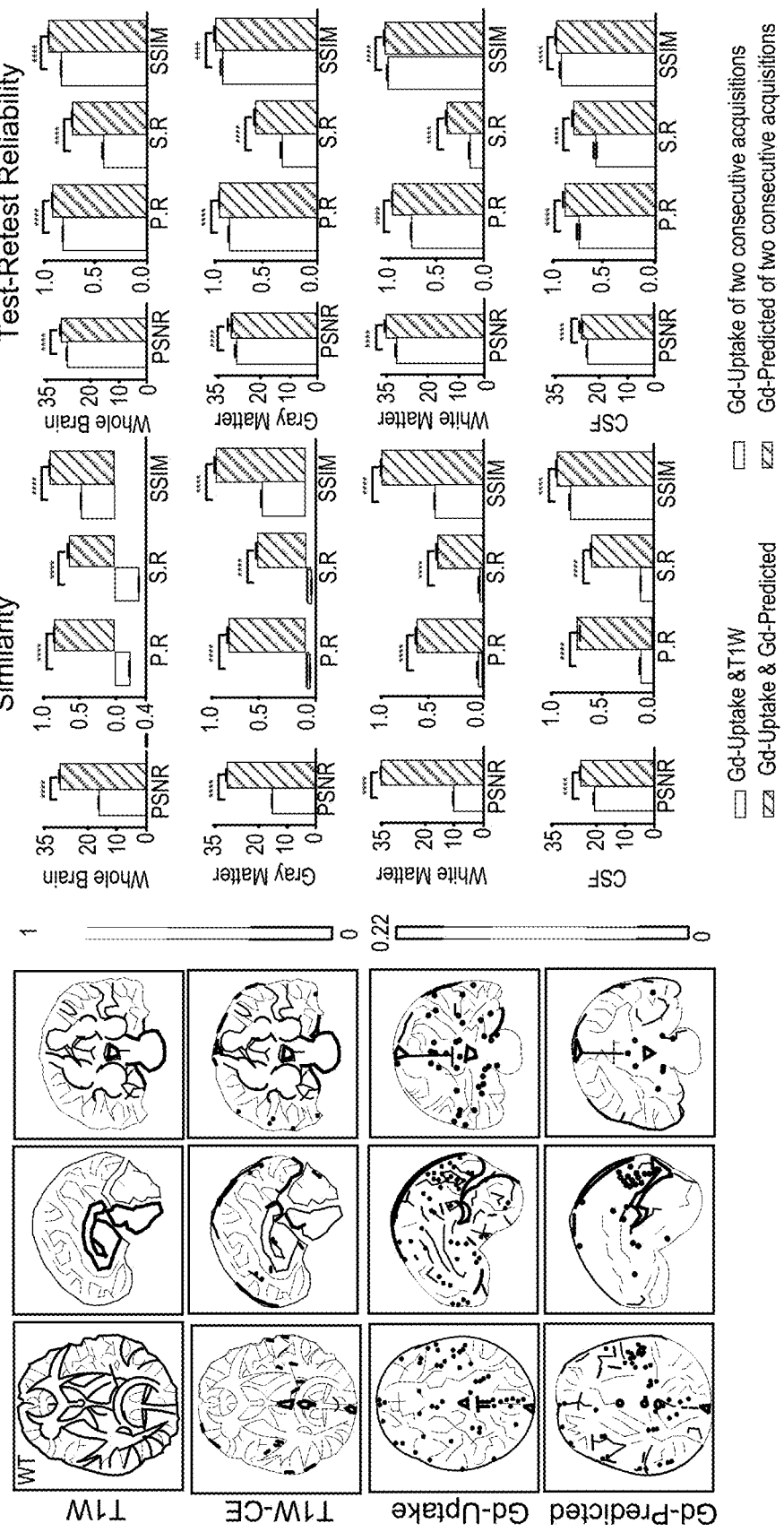
FIG. 22A is a set of further exemplary images of the exemplary DeepContrast prediction according to an exemplary embodiment of the present disclosure.
FIGS. 22B and 22C are sets further exemplary graphs illustrating a comparison between the exemplary Deep Contrast prediction and the ground truth according to an exemplary embodiment of the present disclosure.
Figure 31:
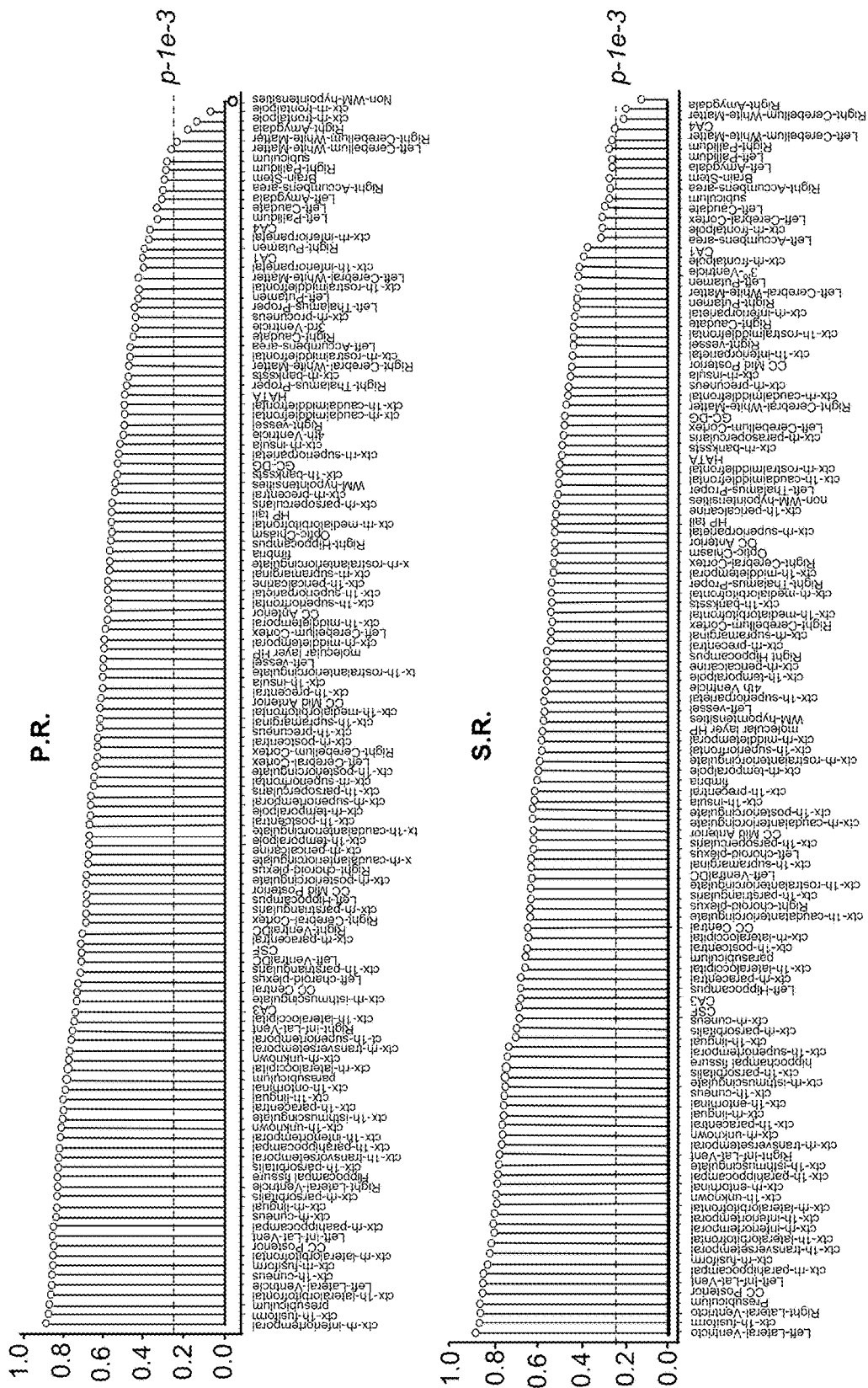
FIG. 31 is a set of exemplary maps illustrating correlation between a gadolinium-uptake and gadolinium-predicted over the entire brain according to an exemplary embodiment of the present disclosure.

After certain exemplary modifications to the network architecture, hyper-parameters, and training strategies, the exemplary DeepContrast model was adapted to be used on a human brain MRI dataset to predict gadolinium contrast from structural T1-weighted non-contrast scans. On the stand-alone test set with 179 scans, the gadolinium-predicted maps resembled the ground truth gadolinium-uptake maps to a great extent, achieving the highest metrics reported by far in the literature. (See e.g., FIGS. 22A and 22B). A follow-up correlation analysis as shown in FIG. 31 demonstrated that the similarity between the predicted contrast and the ground truth can withstand scrutiny at a finer ROI scale.

The reproducibility of the exemplary DeepContrast model was evaluated in test-retest acquisitions. While the experimentally acquired gadolinium-uptake maps of the same subject showed high similarity, the gadolinium-predicted maps demonstrated even lower between-session variation, indicating a significant test-retest reliability. (See e.g., FIG. 22C).

Exemplary DeepContrast Visualizes Functional Lesions

Gadolinium-predicted maps were generated from non-contrast T1-weighted MRI scans with DeepContrast, and subsequently quantified CBV-predicted maps with sub-millimeter in-plane resolution of 0.68×0.68 mm in the coronal planes and slice thickness of 3 mm. Then, voxel-based analyses ("VBA") and region-based studies were performed to localize the regions in such CBV-predicted maps that can be reliably affected by normal aging, by Schizophrenia clinical high-risk ("CHR") and by AD.

Exemplary NormalAging determination. The first study aimed to validate whether DeepContrast can capture the subtle aging effects on basal metabolism across the hippocampal circuit. The D) was found to be the region most reliably affected by aging within the hippocampal formation, as indicated in FIG. 23B. Further investigations demonstrated that the CBV-predicted maps carried similar age-related changes as observed in ground truth CBV maps, both within selected landmark regions known to be targeted by aging (see e.g., FIGS. 32A-32C) and over all cortical ROIs in general. (See e.g., FIGS. 33A-33C).

Exemplary Schizophrenia determination. The second study aimed to validate whether DeepContrast can capture the regional vulnerability in patients who can be clinically high risk for Schizophrenia. CA1 was found to be the region most reliably affected within the hippocampal formation despite that, the cluster-level significance did not reach the threshold of 0.05, as shown in FIG. 23C. Follow-up slice-based analysis in the left and right CA1 regions indicated a significant patient-related increase in five consecutive slices (e.g., thickness=0.68 mm) within the left anterior CA1 region.

Exemplary Alzheimer's Disease determination. The third study aimed to validate whether DeepContrast can capture the regional vulnerability in patients with Alzheimer's Disease dementia. The right transentorhinal cortex was found to be the region most reliably affected in patients within the hippocampal formation, as indicated in FIG. 23D.

Exemplary DeepContrast Enhances Structural Lesions

Figure 24A:
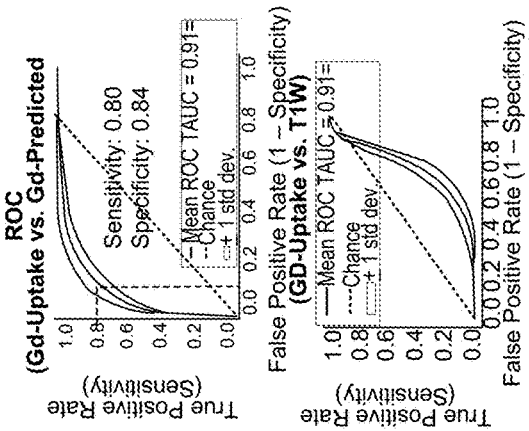
FIG. 24A is a set of exemplary images of predictions using the exemplary Human Tumor Brain Model according to an exemplary embodiment of the present disclosure.
Figure 24C:
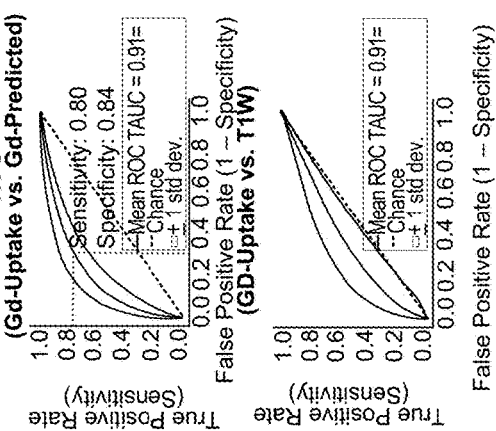
FIG. 24C is a set of exemplary tumor segmentation receiver operating characteristic curves of Gd-Predicted versus T1W according to an exemplary embodiment of the present disclosure.
Figure 24B:
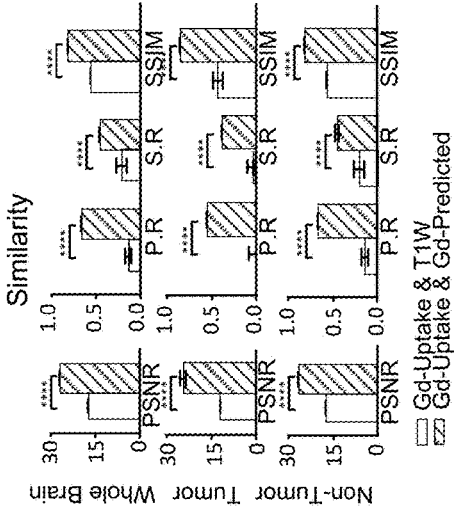
FIG. 24B is a set of exemplary graphs illustrating the similarity between the exemplary Human Tumor Brain Model and the ground truth according to an exemplary embodiment of the present disclosure.

Exemplary Brain Tumor determination. In order to accurately capture the high variance present within brain tumors, the exemplary DeepContrast model was trained with a large-scale brain tumor MRI dataset, which again was able to generate contrast predictions that were similar to the ground truth. (See e.g., FIGS. 24A-24C). While the overall performance over the entire brain region can be inferior to the healthy human brain model, the PSNR can still be quite remarkable. Further, the qualitative enhancement of the tumor region can be clearly seen in the gadolinium-predicted map, both in 2D slices and in 3D volume renderings. Moreover, the high-enhancement regions in the gadolinium-predicted maps had considerable overlap with those in the gadolinium-uptake maps, as shown in the ROC study. (See e.g., FIG. 2C).

Figure 24E:
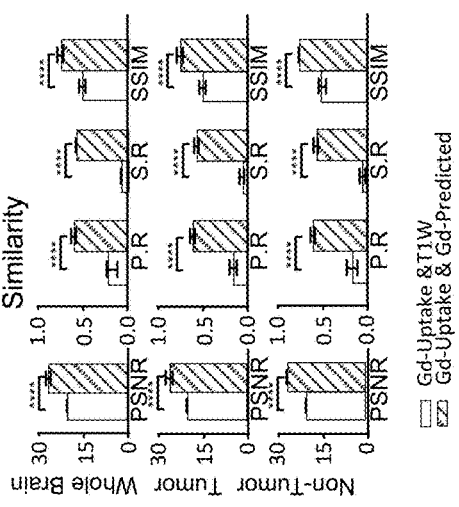
FIG. 24E is a set of exemplary graphs illustrating the similarity between the exemplary breast cancer model and the ground truth according to an exemplary embodiment of the present disclosure.
Figure 24D:
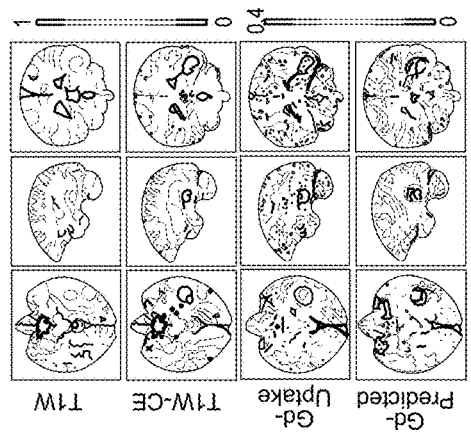
FIG. 24D is a set of exemplary images of predictions using the exemplary breast cancer model according to an exemplary embodiment of the present disclosure.
Figure 24F:
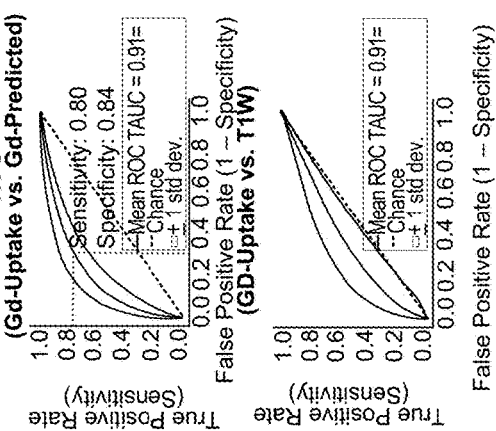
FIG. 24F is a set of exemplary breast cancer tumor segmentation receiver operating characteristic curves of Gd-Predicted versus T1W according to an exemplary embodiment of the present disclosure.

Exemplary Breast Tumor determination. The exemplary DeepContrast model was evaluated on other organs. A study using the Breast-MRI-NACT-Pilot image collection, which contains longitudinal dynamic contrast, enhanced ("DCE") MRI studies on patients undergoing neoadjuvant chemotherapy ("NACT") for invasive breast cancer was conducted. As breast tumors can be hard to distinguish from healthy tissue without the additional contrast provided by GBCAs, the role of DeepContrast can be especially critical in screening for breast cancer. Similar to the case in brain tumors, the qualitative and quantitative evaluation results shown in FIGS. 24D-24F indicated the promising potential of applying DeepContrast to breast tumor enhancement.

Exemplary Discussion

By using a quantitative gadolinium dataset in mice and people, the exemplary hypothesis that deep learning can, for example, generate gadolinium-equivalent information from a single and common MRI scan across an array of lesions was evaluated.

Gadolinium's utility for MRI can be organized around two distinct pathophysiology. The first pathophysiology can be a breakdown of the blood-brain barrier that often accompanies many structural lesions, and in which case gadolinium extravasates into the parenchyma and enhances lesion detection. The second pathophysiology can be alterations in neuronal metabolism, typifying most functional disorders, in which case intravascular gadolinium can be used to quantify regional CBV, a hemodynamic variable tightly coupled to energy metabolism. Individual models were optimized for each of the 5 disorders investigated. Nevertheless, as gadolinium's utility can be reduced to two pathophysiologies.

Gadolinium contrast can be much subtler for functional compared to structural lesions, and the exemplary findings in aging, schizophrenia, and Alzheimer's disease can be considered the strongest validation. Nevertheless, since most of the concerns over gadolinium's safety have emerged when cancer patients can be imaged multiple times over the course of their disease, validating DeepContrast in tumors was equally important.

DeepContrast's utility can be organized according to its two broad applications. The first exemplary application can be for research. There are now over two dozen brain MRI databases, such as ADNI (see e.g., FIG. 35), whose sole purpose can be to advance clinical research. Standard T1-weighted MRI scans can be the most common acquisition across all of these datasets, typically acquired for mapping regional structural differences, such as regional volume or cortical thickness. DeepContrast can be retroactively applied to these datasets, and so investigators can now generate functional maps, significantly expanding pathophysiological insight that can be derived across the range of disorders.

DeepContrast's second application can be provided for patient care. For patient populations with structural lesions, such as cancer patients for example, gadolinium can always be considered the gold standard, particularly during initial evaluation or for surgical planning. For these patients, however, DeepContrast may substitute gadolinium when tracking the course of the disease or treatment response. For patient populations with functional lesions, those with neuropsychiatric and neurodegenerative disorders, a T1-weighted scan can be ordered as part of standard clinical practice, to rule-out structural lesions. For these patients, deriving CBV maps via DeepContrast potentially obviates the need for ordering other more invasive, burdensome, and expensive neuroimaging studies for mapping metabolic dysfunction.

Exemplary Methods

Exemplary Subjects

Healthy Mouse Brain. 49 healthy adult C576J/BL male mice (e.g., 12-14 months old) were used.

Exemplary Mouse GBM 9 adult C576J/BL male mice were included, which were injected with PDGFB~(+/+) PTEN~(-/-) p53~(-/-) glioblastoma cells. (See, e.g., References 98). 50,000 cells in 1 µL solution were stereotactically injected into the brain. MRI scans of GBM mice were obtained 10 days after injection.

Exemplary Healthy Human Brain and Human Aging determination. The healthy human MRI data was aggregated from a collection of previous acquisitions at Columbia University, resulting in 598 subjects (e.g., 16-94 years old) with single acquisitions, and another 11 subjects with baseline and follow-up acquisitions 14 days apart. The aging study consists of 177 subjects (e.g., 20-72 years old) that can be cognitively normal.

Exemplary Human CHR determination. Scans from a previous study that included 92 subjects (e.g., 15-35 years old), among which 74 are schizophrenia clinical high-risk patients, and 18 are normal controls, were collected.

Exemplary Human AD determination. 50 CN and 50 AD subjects were randomly sampled from the Alzheimer's Disease Neuroimaging Institute ("ADNI"), resulting in a 100-subject (e.g., 60-90 years old) dataset.

Exemplary Human GBM determination. 268 subjects (e.g., 36-86 years old) were selected from the original 335 subjects present within the Brain Tumor Segmentation ("BraTS") dataset, based on successful segmentation through the MALPEM segmentation pipeline. (See, e.g., Reference 99).

Exemplary Human Breast Cancer. All 68 subjects from the The Cancer Imaging Archive ("TCIA") Breast MRI NACT Pilot dataset were used.

Exemplary Image Acquisition Protocols

Exemplary Healthy Mouse Brain and Mouse GBM determination. CBV-fMRI was used to image two independent groups of mice, young and old male WT and GBM mice used in healthy mouse brain and mouse GBM studies, with the imaging protocol as previously described. (See, e.g., Reference 100). A Bruker BioSpec 94/30 (e.g., field strength, 9.4 T; bore size, 30 cm) horizontal small animal MRI scanner equipped with CryoProbe and software ParaVision 6.0.1 (e.g., Bruker BioSpin, Billerica, Mass., USA) and a 23-mm 1H circularly polarized transmit/receive capable mouse head volume coil were used for the imaging. Mice were anesthetized using medical air and isoflurane (e.g., 3% volume for induction, 1.1-1.5% for maintenance at 1 liter/min air flow, via a nose cone). A flowing water heating pad was used to maintain the body temperature at around 37° C. Sterile eye lubricant was applied before each scan. T2-weighted images were acquired before and 36 min after intraperitoneal injections of the gadolinium-based contrast agent Gadodiamide (e.g., Omniscan; GE Healthcare, Princeton, N.J., USA) at the dosage of 10 mmol/kg. T2-weighted images were acquired with a Refocused Echoes sequence (e.g., repetition time ("TR")=3,500 ms, effective echo time ("TE")=45 ms, rapid acquisition and RARE factor=8, voxel size=76×76×450 µm).

Exemplary Healthy Human Brain and Human Aging determination. The images were acquired under a steady-state CBV-fMRI protocol as previously described. (See, e.g., Reference 95). A gradient echo T1-weighted scan (e.g., TR=6.7 ms, TE=3.1 ms, FOV=240×240×192 mm, voxel size=0.9×0.9×0.9 mm) was acquired before a pair of unscaled T1-weighted images (e.g., TR=7 ms, TE=3 ms, FOV=240×240×196 mm, voxel size=0.68×0.68×3 mm), all using a Philips Achieva 3.0-T MRI scanner. The image resolution used results from a systematic exploration of the scan protocol's parameters. Scans were acquired before and after a bolus injection of a Gadolinium-based contrast agent (e.g., Omniscan, GE Healthcare).

Exemplary Human CHR determination. The T1-weighted images were acquired using the same scan parameters as mentioned in the studies above (e.g., Philips Achieva 3.0-T MRI scanner, TR=7 ms, TE=3 ms, FOV=240×240×196 mm, voxel size=0.68×0.68×3 mm).

Exemplary Human ADNI determination. The images included in the exemplary studies were acquired using a customized back-to-back 3D magnetization prepared rapid gradient echo (e.g., MP-RAGE) protocol, yielding near-isotropic images (e.g., voxel size around 1×1×1 mm). (See, e.g., Reference 101).

Exemplary Human GBM determination. The images were acquired using different protocols from 19 institutions, the majority of which was acquired with 3D acquisition and voxel spacing of isotropic 1 mm. (See, e.g., Reference 102).

Exemplary Human Breast Cancer TCIA determination. All breast MRI used in this study were acquired on a 1.5-T scanner (e.g., Signa, GE Healthcare, Milwaukee, Wis.) using a bilateral phased array breast coil. The MR imaging protocol included a 3D localizer and a unilateral sagittal DCE acquisition. The DCE acquisition utilized a high spatial resolution, low temporal resolution, T1-weighted, fat-suppressed 3D fast gradient-recalled echo sequence developed for pre-surgical staging (e.g., TR=8, TE=4.2, flip angle=20 degrees; FOV=18-20 cm, acquisition matrix=256×192×60, voxel size=0.7×0.94×2.0 mm). A minimum of three time points were acquired during each contrast-enhanced MRI protocol: a pre-contrast scan (t0), followed by 2 consecutive post-contrast time points: early (t1) and late (t2) phases. All 161 post-contrast scans used in this study were acquired at the earlier time point (t1), which is 2.5 minutes after Gd injection. The gadopentetate dimeglumine contrast agent (e.g., Magnevist, Bayer HealthCare, Berlin, Germany), was injected at a dose of 0.1 mmol/kg of body weight (e.g., injection rate=1.2 mL per second) followed by a 10 mL saline flush, with injection starting coincident with the start of the early t1 phase acquisition. Fat suppression was performed using a frequency-selective inversion recovery preparatory pulse.

Exemplary Preprocessing and Partitioning

Exemplary Healthy Mouse Brain determination. In total, 49 WT mice were used in this study. Whole brain T2W MRI scans before (T2W) and 35 minutes after intraperitoneal injection (T2W-CE) of Gadodiamide at 10 mmol/kg were acquired with identical scan parameters as previously described in CBV-fMRI protocol. The Gd-Uptake ground truth was quantified with the standardized delta-R2, which was derived using the same method as discussed before (see, e.g., Reference 100), followed by a standardization to the dynamic range of [0, 1]. 3D PCNN (see, e.g., Reference 103) with manual correction was used to generate brain masks, which was used as training fields over which the model was optimized and performance metrics were calculated. A train-validation-test ratio at 8:1:1 was applied in the healthy mouse brain model training.

Exemplary Mouse GBM determination. For scans of tumor subjects, the CBV maps and brain masks were derived using the same methods as descripted in the healthy mouse brain study, and tumor masks were generated in addition to the brain masks using the Fuzzy-C-Means segmentation. (See, e.g., Reference 104). 6 GBM subjects were added to the training set while 3 GBM subjects replaced the original testing set of the Healthy Mouse Brain Model.

Exemplary Healthy Human Brain. T1-weighted MRI scans were acquired using the protocols as described previously (see, e.g., References 95 and 96), before (T1W) and 4 minutes after (T1W-CE) intravenous injection of Gadodiamide. During the MRI acquisition for the same session, the receiver gain was kept constant and the offset was set to zero, and as a result, the T1W and T1W-CE scans share the same scaling and zero shifting. Each T1W & T1W-CE pair was spatially aligned when provided. For intensity normalization, each T1W scan was compressed to the dynamic range of [0, 1], and the corresponding T1W-CE scan was scaled accordingly to match the constant scaling. The Gd-Uptake ground truth was quantified with the steady-state MRI method (see, e.g., Reference 95), by subtracting the normalized T1W scans from the respective T1W-CE scans. Brain masks were generated using FSL, which was used as training fields over which the model was optimized and performance metrics were calculated. The train-validation split was completed at a 7:2 ratio, while 179 subjects were left for the test set.

Exemplary Human Aging determination. The 177-subject cohort used for the aging study was a subset of the 179 subjects in the test set of the Healthy Human Brain Model, where 2 subjects were dropped due to low segmentation quality through the FreeSurfer (v6.0.0) Parcellation. (See, e.g., Reference 105). After normalization to the dynamic range of [0, 1], the scans were directly treated as inputs to the model to generate Gd-Uptake estimations.

Exemplary Human CHR determination. The 94-scan cohort for the CHR study was acquired using the same scan parameters as those used to train the DeepContrast Healthy Human Brain Model, which ensures minimal discrepancy in scan appearance. CHR patients present very little structural deformation, which ensures minimal discrepancy in scan anatomy. Therefore, no additional measures need to be taken to deal with appearance or anatomy variances. After normalization to the dynamic range of [0, 1], the scans were directly treated as inputs to the model.

Exemplary Human AD determination. The back-to-back repeated baseline scans for each subject in the AD study cohort were gathered, and the resulting dataset contains 100 scans of normal controls and 100 scans of patients with dementia. An exemplary challenge was that the appearance and anatomy of the scans used in the AD study notably differ from those used to train the DeepContrast Healthy Human Brain Model. They were acquired under the same field strength (i.e., 3T), but the specific scan parameters such as echo time and repetition time can be different between the ADNI protocol and the CBV-fMRI protocol, thus yielding the mismatch in appearance. The subjects in the AD study can be generally older (e.g., 60-90 years old) and half of them suffered from Alzheimer's, thus resulting in the mismatch in anatomy. These issues were approached by first minimizing the between-cohort appearance difference using a dynamic histogram warping ("DHW") procedure (see, e.g., Reference 106) as it was demonstrated to be among the best linear and non-linear intensity matching methods in medical imaging. (See, e.g., Reference 107). For example, the mean normalized-brain-region 2048-bin histogram of each cohort were calculated, a bin-to-bin mapping between the cohorts were derived, and the mapping was applied to each individual scan in the AD study. Secondly, the anatomical difference was minimized by running a diffeomorphic registration prior to applying the DeepContrast model. After these two procedures, the scans were normalized to the dynamic range of [0, 1] and they were provided to the model to generate the gadolinium-predicted maps and subsequently the CBV-predicted maps.

Exemplary Human GBM determination. The data used in the Human GBM study is from an open dataset called BraTS. (See, e.g., References 105-108). The BraTS dataset includes T1W, T1W-CE, and tumor region scans. The T1W and T1W-CE pairs were spatially aligned when provided. Rigid registration was performed to register all scans across subjects to a common template space. T1W scans were normalized using the maximum of the non-tumor region present within each scan. Scaling correction was then used to adjust T1W-CE scans. Specifically, T1W and T1W-CE pairs may need to be in the same scaling system in order to determine Gd-Uptake. This scaling correction can be applied by identifying a region, which remains fairly unchanged after contrast enhancement. White matter has shown to demonstrate this property. (See, e.g., Reference 111). White matter regions were identified using the MALPEM segmentation pipeline (see, e.g., Reference 99) and T1W-CE scans were then scaled using a scaling ratio calculated from the average intensities in the T1W and T1W-CE white matter regions.

Exemplary Human Breast Cancer determination. For each DCE acquisition, the non-contrast (T1W) scan and the scan acquired at the first time point of the DCE protocol (T1W-CE) were included, totaling a number of 161 pairs. T1W and T1W-CE pairs were both normalized using the maximum of the T1W scans before being fed into the DeepContrast model.

Exemplary DeepContrast Implementations

Figure 20:
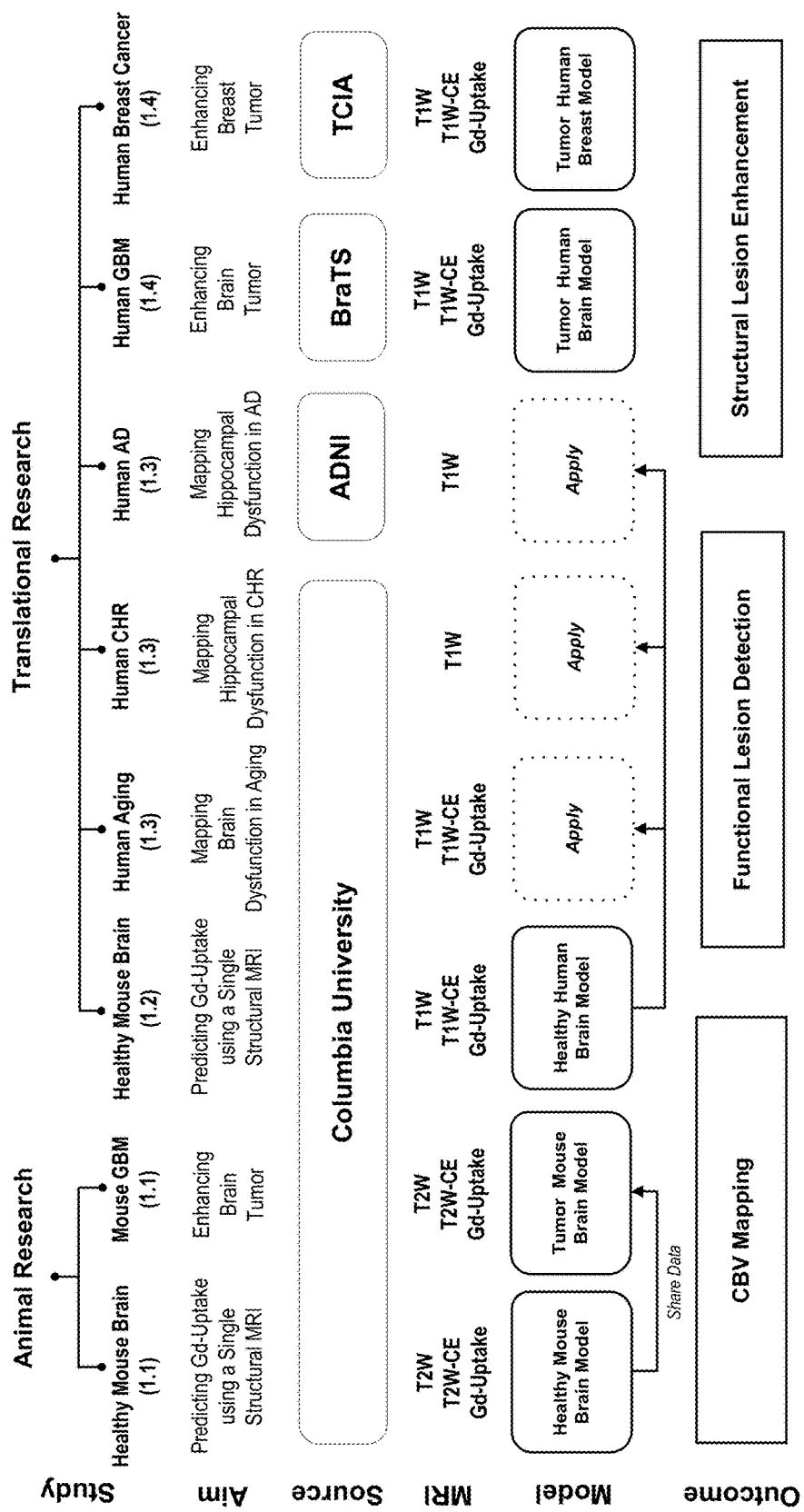
FIG. 20 is an exemplary diagram of various research studies according to an exemplary embodiment of the present disclosure.

All five model variants developed in the exemplary studies, as shown in FIG. 20, share the common residual attention U-Net ("RAU-Net") architecture. (See e.g., FIGS. 26A-26D). Model inputs can be the non-contrast MRI scans, while the outputs can be the corresponding predicted gadolinium contrast. The exemplary inputs and outputs can be in equal dimensions and can be either 2D or 3D depending on the nature of the scan protocols (e.g., 2D slices can be used for 2D MRI scans, whereas 3D volumes can be used for 3D MRI scans).

The RAU-Net can include features from the U-Net architecture (see, e.g., Reference 112), and can include residual blocks (see, e.g., Reference 113) and the attention gates. (See, e.g., References 114 and 115). As an example of a convolutional neural network ("CNN"), the U-Net extracts imaging features by utilizing local convolutions along the entire image or volume. The U-Net consists of several encoding layers across which the image dimension shrinks, whereas the feature dimension increases so that compact high-level abstractions can be generated along the process, and the same number of decoding layers to decipher these abstractions into image space information. The add-on residual blocks simplify the entities to be approximated across each layer and therefore enables training of deeper networks, while the attention gates learn to differentially enhance or suppress specific regions in the feature maps so that the downstream outcomes better suit the desired task.

For example, the encoding and decoding paths consist of the same number of residual convolution blocks that utilize concatenation, attention mechanisms and skip connections such that layers feed not only into the next layer, but also into the layer after the next layer. On the encoding path, each residual block can be followed by a max-pooling layer, and the last feature map feeds into a bottleneck layer with 3×3 convolution and batch normalization, connecting the deepest layer to the decoding path with 4 more blocks alternating one un-pooling layer and one residual block. Skip connections concatenate the output of each dense layer in the encoding path with the respective un-pooled feature map of the same size before feeding it as input to the decoding residual block. The output of the last decoding layer can be the input for a 1×1 convolution layer that produces the final Gd-Predicted map.

Figure 27:
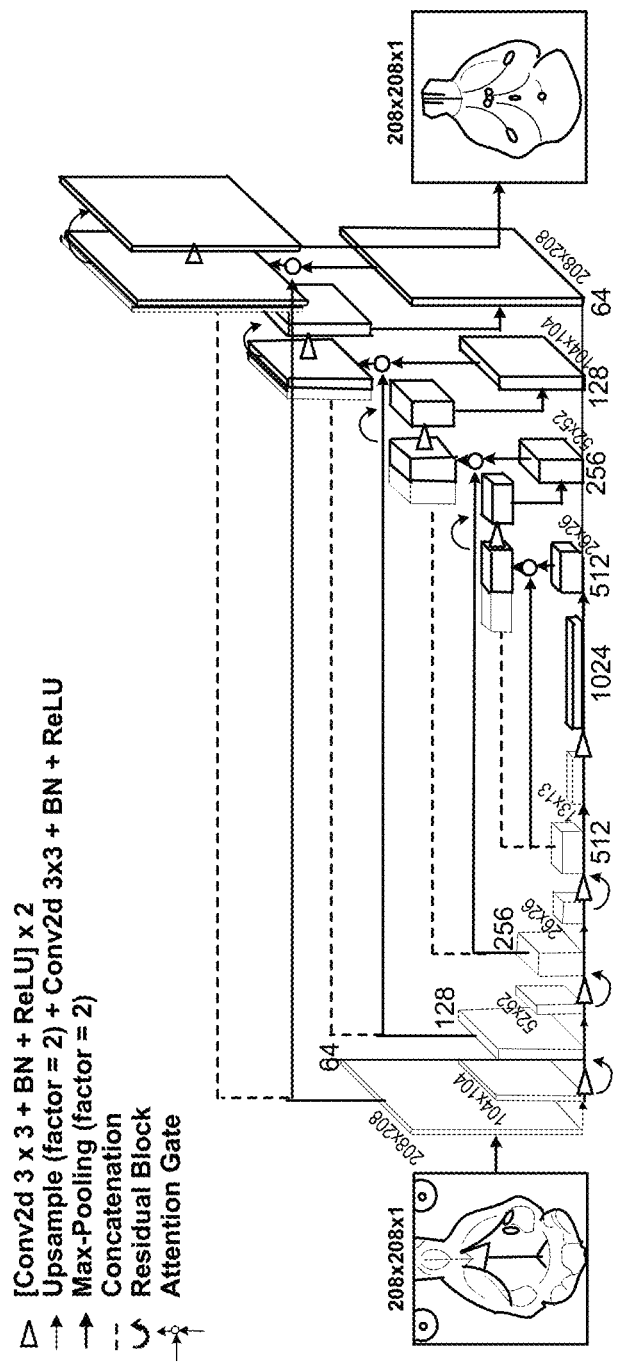
FIG. 27 is an exemplary diagram illustrating a neural network architecture according to an exemplary embodiment of the present disclosure.

Exemplary Healthy and Tumor Mouse Brain Model. The exemplary model used in mouse studies (see e.g., FIG. 27) can be a 2D RAU-Net that consists of 5 encoding and decoding layers. The exemplary model input can be a 2D axial slice of the mouse brain scans. Adam optimizer with a learning rate of 0.001 was used in this study. The exemplary batch size can be 3 and the loss function can be MSE.

Figure 28:
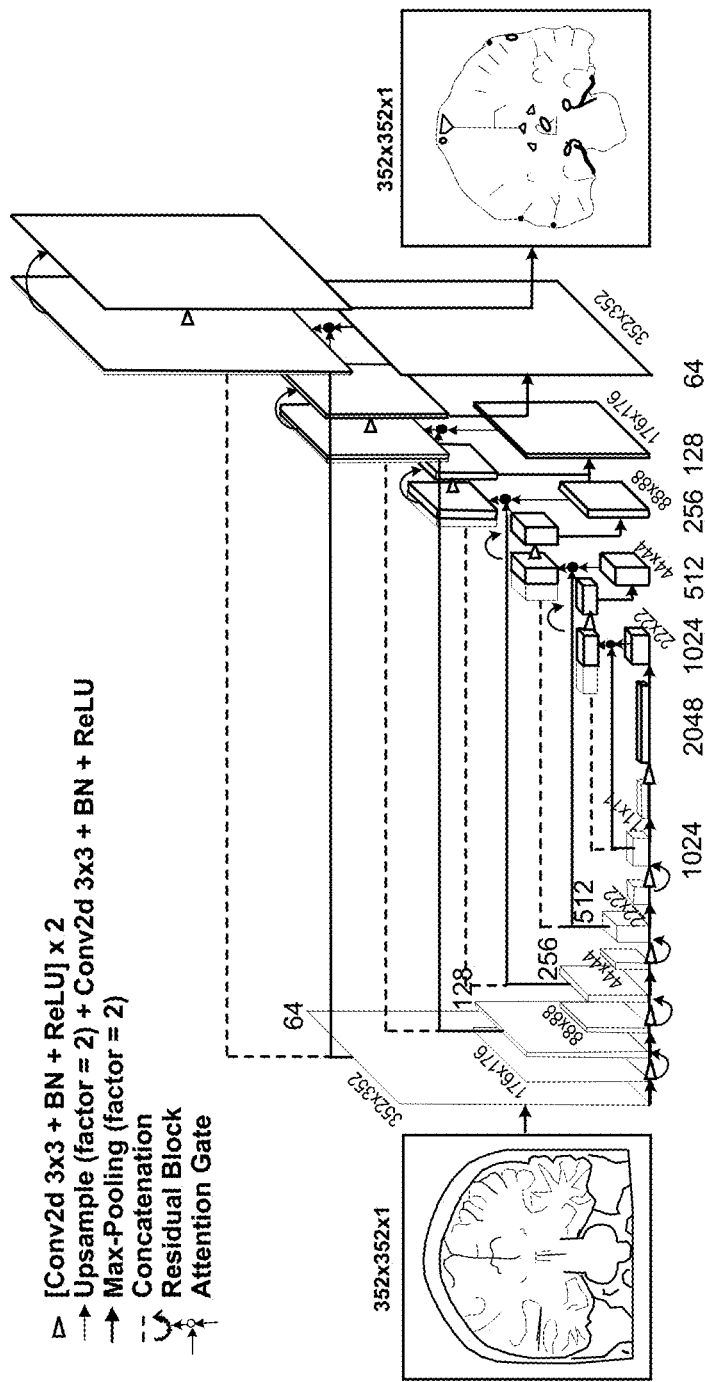
FIG. 28 is an exemplary diagram illustrating a further neural network architecture according to an exemplary embodiment of the present disclosure.

Exemplary Healthy Human Brain Model. The exemplary model used in the healthy human study and further applied to the Aging, CHR and AD studies (see e.g., FIG. 28) can be a 2D RAU-Net that consists of 6 encoding and decoding layers. The exemplary model input can be a 2D coronal slice of the human brain scans. SGD optimizer with an adaptive learning rate handle with 0.1 initial learning rate was used in this study. The exemplary batch size can be 4 and a robust adaptive loss function (see, e.g., Reference 116) was utilized. The robust adaptive loss function can be a generalization of the Cauchy/Lorentzian, Geman-McClure, Welsch/Leclerc, generalized Charbonnier, Charbonnier/pseudo-Huber/L1-L2, and L2 loss functions. By introducing robustness as a continuous parameter, the robust adaptive loss function facilitates procedures built around robust loss minimization to be generalized, which improves performance on basic vision tasks like calculating the intensity mapping function in the exemplary case.

Figure 29:
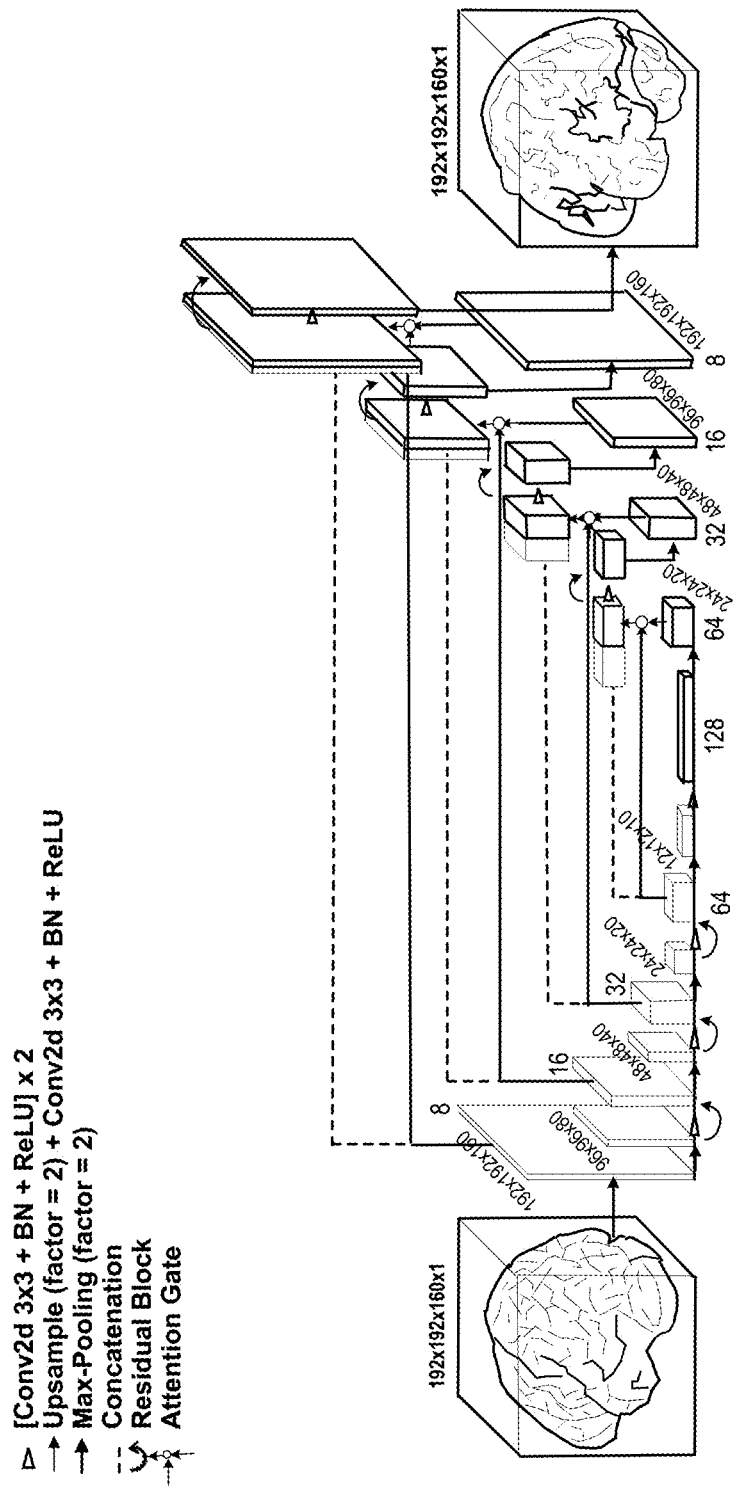
FIG. 29 is an exemplary diagram illustrating an even further neural network architecture according to an exemplary embodiment of the present disclosure.

Exemplary Tumor Human Brain Model. The exemplary model used in the human tumor brain study (see e.g., FIG. 29) can be a 3D RAU-Net that consists of 5 encoding and decoding layers. The exemplary model input can be a 3D human brain volume. SGD optimizer with an adaptive learning rate handle with 0.001 initial learning rate was used in this study. The exemplary batch size can be 1 and the robust adaptive loss function (see, e.g., Reference 116) was utilized.

Figure 30:
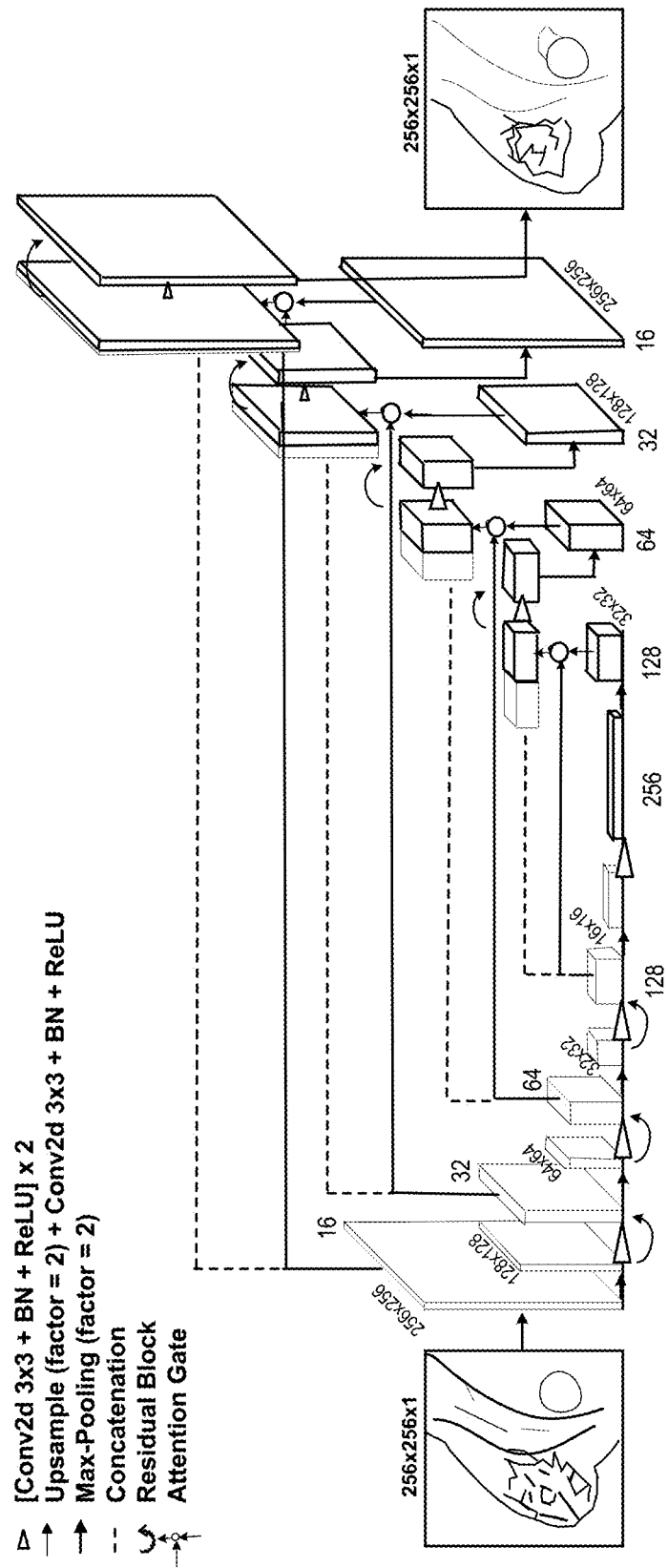
FIG. 30 is an exemplary diagram illustrating a further neural network architecture according to an exemplary embodiment of the present disclosure.

Exemplary Tumor Human Breast Model. The exemplary model used in the tumor human breast study (see e.g., FIG. 30) can be a 2D RAU-Net that consists of 6 encoding and decoding layers. The exemplary model input can be a 2D sagittal slice of the human breast scans. SGD optimizer with an adaptive learning rate handle with 0.001 initial learning rate was used in this study. The exemplary batch size can be 4 and a robust adaptive loss function (see, e.g., Reference 110) was utilized.

Exemplary Statistical Methods

Estimation-GT similarity assessments (e.g., applicable to Healthy Mouse Brain, Healthy Human Brain, Mouse GBM, Human GBM, Human Breast Cancer). PSNR, SSIM, P.R and S.R were used to quantify the performance of all the DeepContrast models. PSNR, Pearson correlation coefficient, and Spearman correlation coefficient were evaluated within the brain region, and SSIM was calculated in the minimum bounding box around the brain.

Exemplary Tumor segmentation performance assessments (e.g., applicable to Mouse GBM, Human GBM, Human Breast Cancer). In addition to the basic similarity assessments, Dice coefficient and Hausdorff distance were used in the evaluation metrics for tumor studies to evaluate the tumor segmentation similarity based on the Gd-Predicted map and its ground truth Gd-Uptake. For the generation of the ROC curve, the ground truth Gd-uptake images were binarized. This was performed using an Otsu filter (see, e.g., Reference 117) which automatically selected the threshold value dividing the voxels into 2 classes. The area under the ROC curve ("AUC") was then created by comparing the continuous prediction to the binarized ground truth using Scikit-learn. (See, e.g., Reference 118).

Exemplary Voxel-based analysis for regional vulnerability localization: Human Aging. Voxel-based analysis (see e.g., FIG. 23B) was performed by first transforming the non-contrast images using a diffeomorphic registration procedure (see, e.g., Reference 119) with nearest-neighbor interpolation to an unbiased brain template created from the 177-scan population. (See, e.g., Reference 119). The gadolinium-predicted map was generated by the Healthy Human Brain model using the native-space non-contrast T1W scans as the input and was subsequently used to quantify CBV-predicted maps by normalizing them by their respective mean value among the top 10% brightest voxels within the brain region. These CBV-predicted maps were then transformed into that template using the identical transformation parameters calculated from the registration process, and subsequently smoothed using a 3 mm-diameter spherical kernel. Transformed CBV-predicted maps were analyzed with a general linear model implemented in SPM12. (See, e.g., Reference 120). Data were analyzed with a multiple regression model, including sex as a covariate and age as the regressor. Age-related differences were contrasted using Student's t test. FreeSurfer regional segmentations were then performed on the unbiased template image, and the hippocampal formation mask can be generated by binarizing and combining the labels corresponding to the hippocampus and entorhinal cortex ("EC"). (See, e.g., Reference 105). The age-related regression t-map was then projected onto the MNI-152 brain template (see, e.g., References 121-123) using diffeomorphic transformation with nearest-neighbor interpolation. The result was thresholded at $p<0.005$ and corrected for multiple comparisons at the cluster level within the hippocampal formation using a Monte-Carlo simulation implemented in AFNI-3dClustSim (see, e.g., References 124-126) run for 10,000 iterations to yield a corrected $p<0.05$. The final corrected age-related regression t-map was then overlaid onto the MNI-152 template in cross-section using 3DSlicer (see, e.g., Reference 127), and also displayed as composite-with-shading volume rendering over semi-transparent models of the hippocampal formation.

Exemplary ROI-based analysis: DG in Human Aging. The 177 native-space CBV-predicted scans were used to conduct the DG ROI analysis. A multiple linear regression with sex as a covariate and age as the regressor was conducted over the bilateral DG, as defined by FreeSurfer parcellation. A scatter plot was drawn (see e.g., FIG. 23E) with each point representing the DG-mean CBV-predicted value after removal of sex effect for one subject.

Exemplary Whole Brain Aging Analysis. The exemplary gadolinium-predicted map was generated in the native space of each subject and was afterwards used for CBV quantification together with the experimentally acquired ground truth Gd-Uptake using the same whole brain top 10% mean normalization. Similarly, the T1W scans were normalized to generate a comparable counterpart. The CBV (e.g., quantified from Gd-Uptake), CBV-Predicted (e.g., quantified from Gd-Predicted), and normalized T1W scans were used for age-related regression in the multiple brain regions. Multiple linear regressions with sex as a covariate and age as the regressor were conducted using the mean CBV/CBV-Predicted/T1W values extracted from the region across 177 subjects, over selected landmarks (see e.g., FIGS. 32A-32D) and over all 72 cortical ROIs. (See e.g., FIGS. 33A-33C). The ROIs were given by FreeSurfer parcellation over the T1W scans in the native space in order to minimize segmentation errors.

Exemplary Voxel-based analysis for regional vulnerability localization: Human CHR. Voxel-based analysis (see e.g., FIG. 23C) was performed by first transforming the non-contrast images using a diffeomorphic registration procedure (see, e.g., Reference 119) with nearest-neighbor interpolation to an unbiased brain template created from the 94-scan population. (See, e.g., Reference 119). The gadolinium-predicted map was generated by the Healthy Human Brain model using the native-space non-contrast T1W scans as the input, and was subsequently used to quantify CBV-predicted maps by normalizing them by their respective mean value among the top 10% brightest voxels within the brain region. These exemplary CBV-predicted maps were then transformed into that template using the identical transformation parameters calculated from the registration process, and subsequently smoothed using a 3 mm-diameter spherical kernel. Transformed CBV-predicted maps were analyzed with a general linear model implemented in SPM12. Data were analyzed with a two-sample t-test after controlling for global variables. CHR-related differences were contrasted using Student's t test. FreeSurfer regional segmentations were then performed on the unbiased template image, and the hippocampal formation mask was generated by binarizing and combining the labels corresponding to the hippocampus and EC. The CHR-related regression t-map was then projected onto the MNI-152 brain template using diffeomorphic transformation with nearest-neighbor interpolation. The exemplary result was thresholded at $p<0.005$ while multiple comparisons at the cluster level of the two clusters (e.g., $p=0.3$) does not reach $p<0.05$. The final corrected CHR-related regression t-map was then overlaid onto the MNI-152 template in cross-section using 3DSlicer, and also displayed as composite-with-shading volume rendering over semi-transparent models of the hippocampal formation.

Exemplary ROI-based analysis: Left anterior CA1 in Human CHR. The 94 template-space CBV-predicted scans were used to conduct the left anterior CA1 ROI analysis. A two-sample t-test was conducted over the left anterior CA1. A box plot overlaid with individual data points was drawn (see e.g., FIG. 23F) to indicate the group-wise difference between the normal controls and the CHR patients.

Exemplary Slice-based analysis for regional vulnerability localization: Human CHR. Slice-based analysis (see e.g., FIG. 34A-34C) was performed by first transforming the non-contrast images using a diffeomorphic registration procedure with nearest-neighbor interpolation to an unbiased brain template created from the 94-scan population. The gadolinium-predicted map was generated by the Healthy Human Brain model using the native-space non-contrast T1W scans as the input and was subsequently used to quantify CBV-predicted maps by normalizing them by their respective mean value among the top 10% brightest voxels within the brain region. These CBV-predicted maps were then transformed into that template using the identical transformation parameters calculated from the registration process, and subsequently smoothed using a 3 mm-diameter spherical kernel. Next the unbiased template as well as these CBV-predicted scans to an isotropic resolution (e.g., voxel size=0.68×0.68×0.68 mm) were sampled using cubic spline interpolation. The hippocampal subfields of the template were parcellated using FreeSurfer, and further cut the left and right CA1 subregions in the hippocampus into slices along the long axes of these structures. The slice-mean CBV-Predicted values were computed for each slice, followed by a 3-slice sliding window averaging to smooth the results. Two-sample t-tests were performed over the smoothed slice-mean CBV-Predicted values to generate the slice-based analysis results.

Exemplary Voxel-based analysis for regional vulnerability localization: Human AD. Voxel-based analysis (see e.g., FIG. 23D) was performed by first transforming the non-contrast images using a diffeomorphic registration procedure with nearest-neighbor interpolation to an unbiased brain template created from the 200-scan (e.g., 100 subjects each with 2 back-to-back repeated scans) population. These non-contrast scans were run through the DeepContrast Healthy Human Brain Model to generate CBV-predicted maps, which were subsequently smoothed using a 3 mm-diameter spherical kernel. Unlike in the aging study, the application of DeepContrast can be performed after the registration process to help eliminate major anatomical variances, since the deformations present in the diseased population have not been previously observed by the model trained on healthy data. Gd-Predicted scans, the direct output of the model, can be used to quantify CBV-predicted maps using the same method as described in the aging study above. These exemplary CBV-predicted maps, already co-registered upon creation, were analyzed with a general linear model implemented in SPM12. Data were analyzed with a multiple regression model, including age, sex and subject identity as covariates and diagnostic class (e.g., cognitive normal vs. dementia) as the regressor. AD-related differences were contrasted using Student's t test. FreeSurfer regional segmentations were then performed on the unbiased template image, and the hippocampal formation mask was generated by binarizing and combining the labels corresponding to the hippocampus and EC, while an extended hippocampal formation mask was additionally generated to also include the parahippocampal cortex. The AD-related regression t-map was then projected onto the MNI-152 brain template using diffeomorphic transformation with nearest-neighbor interpolation. The result was thresholded at $p<0.005$ and corrected for multiple comparisons at the cluster level within the extended hippocampal formation using a Monte-Carlo simulation implemented in AFNI-3dClustSim run for 10,000 iterations to yield a corrected $p<0.05$. The final exemplary corrected AD-related regression t-map was then overlaid onto the MNI-152 template in cross-section using 3DSlicer, and also displayed as composite-with-shading volume rendering over semi-transparent models of the hippocampal formation.

Exemplary ROI-based analysis: Right TEC in Human AD. The exemplary 200 template-space CBV-predicted scans were used to conduct the right transentorhinal cortex ("TEC") ROI analysis. A two-sample t-test was conducted over the right TEC, at the boundary between the right EC and the right parahippocampal cortex ("PHC"). The region was defined as the intersection between the EC-PHC region and a sphere centered at the middle of the EC-PHC intersection and spanning a diameter of the extent of the EC-PHC intersection. A box plot overlaid with individual data points was drawn (see e.g., FIG. 23G) to indicate the group-wise difference between the normal controls and the AD patients.

FIG. 36 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 805. Such processing/computing arrangement 3605 can be, for example entirely or a part of, or include, but not limited to, a computer/processor 3610 that can include, for example one or more microprocessors, and use instructions stored on a computer-accessible medium (e.g., RAM, ROM, hard drive, or other storage device).

As shown in FIG. 36, for example a computer-accessible medium 3615 (e.g., as described herein above, a storage device such as a hard disk, floppy disk, memory stick, CD-ROM, RAM, ROM, etc., or a collection thereof) can be provided (e.g., in communication with the processing arrangement 3605). The computer-accessible medium 3615 can contain executable instructions 3620 thereon. In addition or alternatively, a storage arrangement 3625 can be provided separately from the computer-accessible medium 3615, which can provide the instructions to the processing arrangement 3605 so as to configure the processing arrangement to execute certain exemplary procedures, processes, and methods, as described herein above, for example.

Further, the exemplary processing arrangement 3605 can be provided with or include an input/output ports 3635, which can include, for example a wired network, a wireless network, the internet, an intranet, a data collection probe, a sensor, etc. As shown in FIG. 36, the exemplary processing arrangement 3605 can be in communication with an exemplary display arrangement 3630, which, according to certain exemplary embodiments of the present disclosure, can be a touch-screen configured for inputting information to the processing arrangement in addition to outputting information from the processing arrangement, for example. Further, the exemplary display arrangement 3630 and/or a storage arrangement 3625 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties.
1. Lohrke, Frenzel et al. 2016.
2. Smith, Steven et al. 2019.
3. Fornell 2018.
4. Frenzel, Lengsfeld et al. 2008.
5. Abujudeh, Kaewlai et al. 2009.
6. Lu, Golay et al. 2003.
7. Marino, Helbich et al. 2018.
8. Moreno, Hua et al. 2006.
9. Bakshi, Thompson et al. 2008.
10. Brickman, Khan et al. 2014.
11. Khan, Liu et al. 2014.
12. Neska-Matuszewska, Bladowska et al. 2018.
13. Saade, Bou-Fakhredin et al. 2018.
14. Kaplan and Zhu 2018.
15. Shan, Padole et al. 2019.
16. Gong, Pauly et al. 2018.
17. Chou, Wu et al. 2011.
18. Dubey and Mushrif 2016.
19. Myronenko 2019.
20. Hore and Ziou 2010.
21. Rockafellar and J-B Wets 2004.
22. Feng, Hamberger et al. 2018.
23. Raichle 1983.
24. Belliveau, Kennedy et al. 1991.
25. Jagust 2013.
26. Uh, Lewis-Amezcua et al. 2010.
27. J Covarrubias, Rosen et al. 2004.
28. Small, Schobel et al. 2011.
29. Takano, Yamashita et al. 2010.
30. Noell, Ritz et al. 2012.
31. Maia, Malheiros et al. 2005.
32. Server, Graff et al. 2011.
33. Law, Yang et al. 2003.
34. Law, Yang et al. 2004.
35. Zhang, Liu et al. 2017.
36. Neska-Matuszewska, Bladowska et al. 2018.
37. Voulodimos, Doulamis et al. 2018.
38. Jiang, Wang et al. 2019.
39. Sorensen 1948.
40. Belliveau et al. 1991.
41. Schobel, Chaudhury et al. 2013.
42. Desikan et al., 2006.
43. B. Fischl et al., 2004.
44. Iglesias et al., 2015.
44. S. A. Small, S. A. Schobel, R. B. Buxton, M. P. Witter, and C. A. Barnes, "A pathophysiological framework of hippocampal dysfunction in ageing and disease", Nat Rev Neurosci, vol. 12, no. 10, pp. 585-601, 2011, doi: 10.1038/nrn3085.
45. U. A. Khan et al., "Molecular drivers and cortical spread of lateral entorhinal cortex dysfunction in preclinical Alzheimer's disease", Nat Neurosci, vol. 17, no. 2, pp. 304-311, 2014, doi: 10.1038/nn.3606.
46. S. A. Schobel et al., "Imaging patients with psychosis and a mouse model establishes a spreading pattern of hippocampal dysfunction and implicates glutamate as a driver", Neuron, vol. 78, n. 1, pp. 81-93, 2013, doi: 10.1016/j.neuron.2013.02.011.
47. A. M. Brickman et al., "Enhancing dentate gyrus function with dietary flavanols improves cognition in older 48. T. E. Smith, A. Steven, and B. A. Bagert, "Gadolinium Deposition in Neurology Clinical Practice", Ochsner J, vol. 19, no. 1, pp. 17-25, Spring 2019, doi: 10.31486/toj.18.0111.
49. FDA. "FDA Drug Safety Communication: FDA warns that gadolinium-based contrast agents (GBCAs) are retained in the body; requires new class warnings."
50. E. Gong, J. M. Pauly, M. Wintermark, and G. Zaharchuk, "Deep learning enables reduced gadolinium dose for contrast-enhanced brain MRI" Journal of Magnetic Resonance Imaging, vol. 48, no. 2, pp. 330-340, 2018/08/01 2018, doi: 10.1002/jmri.25970.
51. J. Kleesiek et al., "Can Virtual Contrast Enhancement in Brain MRI Replace Gadolinium?: A Feasibility Study" Investigative Radiology, vol. 54, no. 10, pp. 653-660, 2019, doi: 10.1097/rli.0000000000000583.
52. L. Lei et al., "Glioblastoma models reveal the connection between adult glial progenitors and the proneural phenotype", PLoS One, vol. 6, no. 5, pp. e20041-e20041, 2011, doi: 10.1371/journal.pone.0020041.
53. H. Moreno, F. Hua, T. Brown, and S. Small, "Longitudinal mapping of mouse cerebral blood volume with MRI" NMR in Biomedicine, vol. 19, no. 5, pp. 535-543, 2006/08/01 2006, doi: 10.1002/nbm.1022.
54. Y. Dubey and M. Mushrif, "FCM Clustering Algorithms for Segmentation of Brain MR Images" Advances in Fuzzy Systems, vol. 2016, pp. 1-14, 03/15 2016, doi: 10.1155/2016/3406406.
55. O. Ronneberger, P. Fischer, and T. Brox, "U-Net: Convolutional Networks for Biomedical Image Segmentation" in Medical Image Computing and Computer-Assisted Intervention—MICCAI 2015, Cham, N. Navab, J. Hornegger, W. M. Wells, and A. F. Frangi, Eds., 2015// 2015: Springer International Publishing.
56. K. He, X. Zhang, S. Ren, and J. Sun, "Deep Residual Learning for Image Recognition" in 2016 IEEE Conference on Computer Vision and Pattern Recognition (CVPR), 27-30 Jun. 2016 2016, pp. 770-778, doi: 10.1109/CVPR.2016.90.
57. O. Oktay et al., "Attention U-Net: Learning Where to Look for the Pancreas" arXiv e-prints.
58. A. Hore and D. Ziou, "Image Quality Metrics: PSNR vs. SSIM" in 2010 20th International Conference on Pattern Recognition, 23-26 Aug. 2010 2010, pp. 2366-2369, doi: 10.1109/ICPR.2010.579.
59. J. Lohrke et al., "25 Years of Contrast-Enhanced MRI: Developments, Current Challenges and Future Perspectives" Advances in Therapy, vol. 33, no. 1, pp. 1-28, 2016/01/01 2016, doi: 10.1007/s12325-015-0275-4.
60. W. Jagust, "Vulnerable neural systems and the borderland of brain aging and neurodegeneration", Neuron, vol. 77, no. 2, pp. 219-234, 2013, doi: 10.1016/j.neuron.2013.01.002.
61. J. Uh et al., "Cerebral blood volume in Alzheimer's disease and correlation with tissue structural integrity", Neurobiol Aging, vol. 31, no. 12, pp. 2038-2046, 2010, doi: 10.1016/j.neurobiolaging.2008.12.010.
62. D. J Covarrubias, B. Rosen, and M. Lev, "Dynamic Magnetic Resonance Perfusion Imaging of Brain Tumors" The oncologist, vol. 9, pp. 528-37, 02/01 2004, doi: 10.1634/theoncologist.9-5-528.
63. M. Neska-Matuszewska, J. Bladowska, M. Sgsiadek, and A. Zimny, "Differentiation of glioblastoma multiforme, metastases and primary central nervous system lymphomas using multiparametric perfusion and diffusion MR imaging of a tumor core and a peritumoral zone-Searching for a practical approach", PLoS One, vol. 13, no. 1, pp. e0191341-e0191341, 2018, doi: 10.1371/journal.pone.0191341.
64. J. Zhang et al., "Clinical Applications of Contrast-Enhanced Perfusion MRI Techniques in Gliomas: Recent Advances and Current Challenges", Contrast Media Mol Imaging, vol. 2017, pp. 7064120-7064120, 2017, doi: 10.1155/2017/7064120.
65. M. Law et al., "Comparison of Cerebral Blood Volume and Vascular Permeability from Dynamic Susceptibility Contrast-Enhanced Perfusion MR Imaging with Glioma Grade" American Journal of Neuroradiology, vol. 25, no. 5, p. 746, 2004.
66. M. Law et al., "Glioma Grading: Sensitivity, Specificity, and Predictive Values of Perfusion MR Imaging and Proton MR Spectroscopic Imaging Compared with Conventional MR Imaging" American Journal of Neuroradiology, vol. 24, no. 10, p. 1989, 2003.
67. A. Simko, T. Lofstedt, A. Garpebring, T. Nyholm, and J. Jonsson, A Generalized Network for MRI Intensity Normalization. 2019.
68. T. E. Smith, A. Steven, and B. A. Bagert, Gadolinium Deposition in Neurology Clinical Practice. Ochsner J, val. 19, no. 1, pp. 17-25, Spring 2019, doi: 10.31486/toj.18.0111.
69. FDA, FDA Drug Safety Communication: FDA warns that gadolinium-based contrast agents (GBCAs) are retained in the body; requires new class warnings.
70. E. Gong, J. M. Pauly, M. Wintermark, and G. Zaharchuk, Deep learning enables reduced gadolinium dose for contrast-enhanced brain MRI. Journal of Magnetic Resonance Imaging, val. 48, no. 2, pp. 330-340, 2018/08/01 2018, doi: 10.1002/jmri.25970.
71. J. Kleesiek et al. Can Virtual Contrast Enhancement in Brain MRI Replace Gadolinium?: A Feasibility Study. Investigative Radiology, val. 54, no. 10, pp. 653-660, 2019, doi: 10.1 097/rli.0000000000000583.
72. A. M. Brickman, U. A. Khan, F. A. Provenzano, L. K. Yeung, W. Suzuki, H. Schroeter, M. Wall, R. P. Sloan, S. A. Small, Enhancing dentate gyrus function with dietary flavanols improves cognition in older adults. Nature Neuroscience, val. 17, no. 12, pp. 1798, 2014, doi: 10.1038/nn.3850.
73. U. A. Khan, L. Liu, F. A. Provenzano, D. E. Berman, C. P. Profaci, R. Sloan, R. Mayeux, K. E. Duff, and S. A. Small, Molecular drivers and cortical spread of lateral entorhinal cortex dysfunction in preclinical Alzheimer's disease. Nature neuroscience, vol. 17, no. 2, pp. 304, 2014, doi: 10.1038/nn.3606.
74. F. A. Provenzano, J. Guo, M. M. Wall, X. Feng, H. C. Sigmon, G. Brucato, M. B. First, D. L. Rothman, R. R. Girgis, J. A. Lieberman, and S. A. Small, Hippocampal Pathology in Clinical High-Risk Patients and the Onset of Schizophrenia. Biological Psychiatry. 2019, doi: 10.1016/j.biopsych.2019.09.022.
75. B. Fischl. FreeSurfer. Neuroimage, vol. 62, no. 2, pp. 774-781, 2012, doi: 10.1016/j.neuroimage.2012.01.021.
76. X. Feng, M. J. Hamberger, H. C. Sigmon, J. Guo, S. A. Small, and F. A. Provenzano. Temporal lobe epilepsy lateralization using retrospective cerebral blood volume MRI. NeuroImage: Clinical, val. 19, pp. 911-917, 2018, doi: 10.1016/j.nicl.2018.05.012.
77. S. M. McGinnis, M. Brickhouse, B. Pascual, and B. C. Dickerson. Age-Related Changes in the Thickness of Cortical Zones in Humans. Brain topography, vol. 24, no. 3-4, pp. 279, 2011 30, doi: 10.1007/s10548-011-0198-6.

78. J. L. Price, A. I. Ko, M. J. Wade, S. K. Tsou, D. W. McKeel, and J. C. Morris, Neuron number in the entorhinal cortex and CA1 in preclinical Alzheimer disease. Archives of neurology, val. 58, no. 9, pp. 1395-1402, 2001, doi: 10.1001/archneur.58.9.1395.
79. A. Bakkour, J. C. Morris, D. A. Walk, and B. C. Dickerson. The effects of aging and Alzheimer's disease on cerebral cortical anatomy: specificity and differential relationships with cognition. Neuroimage, val. 76, pp. 332-344, 2013, doi: 10.1016/j.neuroimage.2013.02.059.
80. Lohrke, J. et al. 25 Years of Contrast-Enhanced MRI: Developments, Current Challenges and Future Perspectives. *Adv. Ther.* 33, 1-28 (2016).
81. Borges, A. R., Lopez-Larrubia, P., Marques, J. B. & Cerdan, S. G. MR Imaging Features of High-Grade Gliomas in Murine Models: How They Compare with Human Disease, Reflect Tumor Biology, and Play a Role in Preclinical Trials. *Am. J Neuroradiol.* 33, 24-36 (2012).
82. Shen, Q. & Duong, T. Magnetic resonance imaging of cerebral blood flow in animal stroke models. *Brain Circ. Mumbai* 2, (2016).
83. Belliveau, J. W. et al. Functional mapping of the human visual cortex by magnetic resonance imaging. *Science* 254, 716-719 (1991).
84. Schobel, S. A. et al. Imaging Patients with Psychosis and a Mouse Model Establishes a Spreading Pattern of Hippocampal Dysfunction and Implicates Glutamate as a Driver. *Neuron* 78, 81-93 (2013).
85. Khan, U. A. et al. Molecular drivers and cortical spread of lateral entorhinal cortex dysfunction in preclinical Alzheimer's disease. *Nat. Neurosci. N. Y.* 17, 304-11 (2014).
86. Lewandowski, N. M. et al. Regional vulnerability in Huntington's disease: fMRI-guided molecular analysis in patients and a mouse model of disease. *Neurobiol. Dis.* 52, 84-93 (2013).
87. Quattrocchi, C. C. & van der Molen, A. J. Gadolinium Retention in the Body and Brain: Is It Time for an International Joint Research Effort? *Radiology* 282, 12-16 (2016).
88. Ramalho, M., Ramalho, J., Burke, L. M. & Semelka, R. C. Gadolinium Retention and Toxicity—An Update. *Adv. Chronic Kidney Dis.* 24, 138-146 (2017).
89. Guo, B. J., Yang, Z. L. & Zhang, L. J. Gadolinium Deposition in Brain: Current Scientific Evidence and Future Perspectives. *Front. Mol. Neurosci.* 11, (2018).
90. Dillman, J. R. & Davenport, M. S. Gadolinium retention—5 years later . . . . *Pediatr. Radiol.* 50, 166-167 (2020).
91. Gong, E., Pauly, J. M., Wintermark, M. & Zaharchuk, G. Deep learning enables reduced gadolinium dose for contrast-enhanced brain MRI. *J. Magn. Reson. Imaging* 48, 330-340 (2018).
92. Kleesiek, J. et al. Can Virtual Contrast Enhancement in Brain MRI Replace Gadolinium?: A Feasibility Study. *Invest. Radiol.* 54, 653-660 (2019).
93. (ISMRM 2019) Contrast-free MRI Contrast Enhancement with Deep Attention Generative Adversarial Network. http://archive.ismrm.org/2019/1091.html.
94. Small, S. A., Schobel, S. A., Buxton, R. B., Witter, M. P. & Barnes, C. A. A pathophysiological framework of hippocampal dysfunction in ageing and disease. *Nat. Rev. Neurosci.* 12, 585-601 (2011).
95. Brickman, A. M. et al. Enhancing dentate gyrus function with dietary flavanols improves cognition in older adults. *Nat. Neurosci.* 17, 1798-1803 (2014).
96. Provenzano, F. A. et al. Hippocampal Pathology in Clinical High-Risk Patients and the Onset of Schizophrenia. *Biol. Psychiatry* 87, 234-242 (2020).
97. Pavlopoulos, E. et al. Molecular mechanism for age-related memory loss: the histone-binding protein RbAp48. *Sci. Transl. Med* 5, 200ra115 (2013).
98. Lei, L. et al. Glioblastoma Models Reveal the Connection between Adult Glial Progenitors and the Proneural Phenotype. *PLOS ONE* 6, e20041 (2011).
99. Ledig, C. et al. Robust whole-brain segmentation: Application to traumatic brain injury. *Med Image Anal.* 21, 40-58 (2015).
100. Moreno, H., Hua, F., Brown, T. & Small, S. Longitudinal mapping of mouse cerebral blood volume with MRI. *NMR Biomed* 19, 535-543 (2006).
101. Petersen, R. C. et al. Alzheimer's Disease Neuroimaging Initiative (ADNI). *Neurology* 74, 201-209 (2010).
102. Menze, B. H. et al. The Multimodal Brain Tumor Image Segmentation Benchmark (BRATS). *IEEE Trans. Med Imaging* 34, 1993-2024 (2015).
103. Chou, N., Wu, J., Bingren, J. B., Qiu, A. & Chuang, K. Robust Automatic Rodent Brain Extraction Using 3-D Pulse-Coupled Neural Networks (PCNN). *IEEE Trans. Image Process.* 20, 2554-2564 (2011).
104. Bezdek, J. C., Ehrlich, R. & Full, W. FCM: The fuzzy c-means clustering algorithm. *Comput. Geosci.* 10, 191-203 (1984).
105. Fischl, B. FreeSurfer. *NeuroImage* 62, 774-781 (2012).
106. Cox, I. J., Roy, S. & Hingorani, S. L. Dynamic histogram warping of image pairs for constant image brightness. in *Proceedings., International Conference on Image Processing* vol. 2 366-369 vol. 2 (1995).
107. Wagenknecht, G., Kaiser, H.-J., Sabri, O. & Buell, U. Dynamic programming algorithm for contrast correction in medical images. in *Nonlinear Image Processing XI* vol. 3961 216-226 (International Society for Optics and Photonics, 2000).
108. Bakas, S. et al. Advancing The Cancer Genome Atlas glioma MRI collections with expert segmentation labels and radiomic features. *Sci. Data* 4, 170117 (2017).
109. Bakas, S. et al. Segmentation Labels for the Pre-operative Scans of the TCGA-GBM collection. (2017) doi:10.7937/K9/TCIA.2017.KLXWJJ1Q.
110. Clark, K. et al. The Cancer Imaging Archive (TCIA): Maintaining and Operating a Public Information Repository. *J. Digit. Imaging* 26, 1045-1057 (2013).
111. Feng, X. et al. Temporal lobe epilepsy lateralization using retrospective cerebral blood volume MRI. *NeuroImage Clin.* 19, 911-917 (2018).
112. Ronneberger, O., Fischer, P. & Brox, T. U-Net: Convolutional Networks for Biomedical Image Segmentation. *ArXiv150504597 Cs* (2015).
113. He, K., Zhang, X., Ren, S. & Sun, J. Deep Residual Learning for Image Recognition. *ArXiv151203385 Cs* (2015).
114. Vaswani, A. et al. Attention Is All You Need. *ArXiv170603762 Cs* (2017).
115. Oktay, O. et al. Attention U-Net: Learning Where to Look for the Pancreas. (2018).
116. Barron, J. T. A General and Adaptive Robust Loss Function. in 4331-4339 (2019).
117. Otsu, N. A Threshold Selection Method from Gray-Level Histograms. *IEEE Trans. Syst. Man Cybern.* 9, 62-66 (1979).
118. Pedregosa, F. et al. Scikit-learn: Machine Learning in Python. *Mach. Learn. PYTHON* 6.

119. Avants, B. B., Tustison, N. & Johnson, H. Advanced Normalization Tools (ANTS). 41.
120. SPM—Statistical Parametric Mapping. https://www-.fil.ion.ucl.ac.uk/spm/.
121. Fonov, V. et al. Unbiased average age-appropriate atlases for pediatric studies. *NeuroImage* 54, 313-327 (2011).
122. Fonov, V., Evans, A., McKinstry, R., Almli, C. & Collins, D. Unbiased nonlinear average age-appropriate brain templates from birth to adulthood. *NeuroImage* 47, S102 (2009).
123. Collins, D. L., Zijdenbos, A. P., Baare, W. F. C. & Evans, A. C. ANIMAL+INSECT: Improved Cortical Structure Segmentation. in *Information Processing in Medical Imaging* (eds. Kuba, A., Šáamal, M. & Todd-Pokropek, A.) 210-223 (Springer, 1999). doi:10.1007/3-540-48714-X_16.
124. Cox, R. W. AFNI: software for analysis and visualization of functional magnetic resonance neuroimages. *Comput. Biomed. Res. Int. J.* 29, 162-173 (1996).
125. Forman, S. D. et al. Improved assessment of significant activation in functional magnetic resonance imaging (fMRI): use of a cluster-size threshold. *Magn. Reson. Med.* 33, 636-647 (1995).
126. Cox, R. W., Chen, G., Glen, D. R., Reynolds, R. C. & Taylor, P. A. FMRI Clustering in AFNI: False-Positive Rates Redux. *Brain Connect.* 7, 152-171 (2017).
127. Fedorov, A. et al. 3D Slicer as an Image Computing Platform for the Quantitative Imaging Network. *Magn. Reson. Imaging* 30, 1323-1341 (2012).

What is claimed is:

1. A non-transitory computer-accessible medium having stored thereon computer-executable instructions for detecting at least one structural disorder of at least one patient, wherein, when a computing arrangement executes the instructions, the computing arrangement is configured to perform procedures comprising:
   receiving magnetic resonance imaging (MRI) information of:
   a. only one gadolinium (Gd)-free pre-contrast T1W structural MRI scan of at least one portion of the at least one patient, or
   b. only gadolinium (Gd)-free pre-contrast T1W structural MRI scans of at least one portion of the at least one patient;
   generating at least one Gd enhanced map of the at least one portion based on the MRI information using at least one machine learning procedure, wherein the at least one machine learning procedure includes at least one attention unit; and
   detecting the at least one structural disorder of the at least one patient based on a Gd contrast of the at least one Gd enhanced map.

2. The computer-accessible medium of claim 1, wherein the at least one Gd enhanced map is a full dosage Gd enhanced map.

3. The computer-accessible medium of claim 1, wherein the at least one machine learning procedure is a convolutional neural network.

4. The computer-accessible medium of claim 1, wherein the computer arrangement is further configured to generate the Gd contrast in the at least one Gd enhanced map using a T2-weighted MRI image of the at least one portion.

5. The computer-accessible medium of claim 1, wherein the at least one machine learning procedure includes at least one residual unit.

6. The computer-accessible medium of claim 5, wherein the at least one machine learning procedure includes at least five layers.

7. The computer-accessible medium of claim 6, wherein the at least one machine learning procedure includes at least one contraction path configured to encode at least one high resolution image into at least one low resolution representation.

8. The computer-accessible medium of claim 7, wherein the at least one machine learning procedure includes at least one expansion path configured to decode the at least one low resolution representation into at least one further high-resolution image.

9. The computer-accessible medium of claim 1, wherein the at least one machine learning procedure includes at least five encoding layers and at least five decoding layers, and wherein each of the at least five encoding layers and each of the at least five decoding layers include two series of 3.times.3 two-dimensional convolutions.

10. The computer-accessible medium of claim 1, wherein the at least one machine learning procedure includes at least five encoding layers and at least five decoding layers, and wherein (i) each of the at least five encoding layers is followed by a 2×2 max-pooling layer, and (ii) each of the at least five decoding layers is followed by at least one 2×2 upsampling layers.

11. The computer-accessible medium of claim 1, wherein the at least one machine learning procedure includes max-pooling and upsampling.

12. The computer-accessible medium of claim 11, wherein the computer arrangement is further configured to perform the max-pooling and the upsampling using a factor of 2.

13. The computer-accessible medium of claim 12, wherein the at least one machine learning procedure includes at least one batch normalization layer and at least one rectified linear unit layer.

14. The computer-accessible medium of claim 1, wherein the at least one portion is at least one section of a brain of the at least one patient.

15. The computer-accessible medium of claim 1, wherein the at least one structural disorder includes at least one of stroke, tumor, trauma, infection, Multiple sclerosis or other inflammatory disease.

16. The computer-accessible medium of claim 15, wherein the at least one tumor is glioma or breast cancer.

17. The computer-accessible medium of claim 1, wherein the MRI information excludes data for a contrast-agent scan.

18. The computer-accessible medium of claim 1, wherein the at least one Gd enhanced map is generated without information associated with data for a contrast-agent scan.

19. A non-transitory computer-accessible medium having stored thereon computer-executable instructions for detecting at least one structural disorder of at least one patient, wherein, when a computing arrangement executes the instructions, the computing arrangement is configured to perform procedures comprising:
   receiving magnetic resonance imaging (MRI) information of:
   a. only one gadolinium (Gd)-free pre-contrast T1W structural MRI scan of at least one portion of the at least one patient, or
   b. only gadolinium (Gd)-free pre-contrast T1W structural MRI scans of at least one portion of the at least one patient;

generating at least one Gd enhanced map of the at least one portion based on the MRI information using at least one machine learning procedure; and detecting the at least one structural disorder of the at least one patient based on a Gd contrast of the at least one Gd enhanced map, wherein the at least one machine learning procedure includes at least five encoding layers and at least five decoding layers.

20. The computer-accessible medium of claim 19, wherein each of the at least five encoding layers and each of the at least five decoding layers includes a residual connection.

21. A method for detecting at least one structural disorder of at least one patient, comprising:

receiving magnetic resonance imaging (MRI) information of:

a. only one gadolinium (Gd)-free pre-contrast T1W structural MRI scan of at least one portion of the at least one patient, or b. only gadolinium (Gd)-free pre-contrast T1W structural MRI scans of at least one portion of the at least one patient;

using a computer hardware arrangement, generating at least one Gd enhanced map of the at least one portion based on the MRI information using at least one machine learning procedure, wherein the at least one machine learning procedure includes at least one attention unit; and using the computer hardware arrangement, detecting the at least one structural disorder of the at least one patient based on a Gd contrast of the at least one Gd enhanced map.

22. A system for detecting at least one structural disorder of at least one patient, comprising:

a computer hardware arrangement configured to:

receive magnetic resonance imaging (MRI) information of:

a. only one gadolinium (Gd)-free pre-contrast T1W structural MRI scan of at least one portion of the at least one patient, or b. only gadolinium (Gd)-free pre-contrast T1W structural MRI scans of at least one portion of the at least one patient, generate at least one Gd enhanced map of the at least one portion based on the MRI information using at least one machine learning procedure, wherein the at least one machine learning procedure includes at least one attention unit, and detect the at least one structural disorder of the at least one patient based on a Gd contrast of the at least one Gd enhanced map.

* * * * *